United States Patent
Forrest et al.

(10) Patent No.: US 12,295,970 B2
(45) Date of Patent: May 13, 2025

(54) IMIDAZOQUINOLINE COMPOUNDS AND PRODRUGS THEREOF

(71) Applicants: UNIVERSITY OF KANSAS, Lawrence, KS (US); HYLAPHARM, LLC, Lawrence, KS (US)

(72) Inventors: Laird Forrest, Lawrence, KS (US); Daniel Aires, Mission Hills, KS (US); Ryan Moulder, Lawrence, KS (US); Ruolin Lu, Lawrence, KS (US); Jordan Hunt, Lawrence, KS (US); Peter Kleindl, Lawrence, KS (US); Ti Zhang, Lawrence, KS (US); Chad Groer, Lawrence, KS (US); Shuang Cai, Lawrence, KS (US)

(73) Assignees: UNIVERSITY OF KANSAS, Lawrence, KS (US); HYLAPHARM, LLC, Lawrence, KS (US)

( * ) Notice: Subject to any disclaimer, the term of this patent is extended or adjusted under 35 U.S.C. 154(b) by 501 days.

(21) Appl. No.: 17/598,160

(22) PCT Filed: Apr. 16, 2020

(86) PCT No.: PCT/US2020/028468
§ 371 (c)(1),
(2) Date: Sep. 24, 2021

(87) PCT Pub. No.: WO2020/214783
PCT Pub. Date: Oct. 22, 2020

(65) Prior Publication Data
US 2022/0177472 A1 Jun. 9, 2022

Related U.S. Application Data

(60) Provisional application No. 62/835,408, filed on Apr. 17, 2019.

(51) Int. Cl.
| | | |
|---|---|---|
| A61K 33/243 | (2019.01) | |
| A61K 45/06 | (2006.01) | |
| A61K 47/36 | (2006.01) | |
| A61K 47/61 | (2017.01) | |
| A61P 29/00 | (2006.01) | |
| A61P 35/00 | (2006.01) | |
| C07D 471/04 | (2006.01) | |
| C07F 15/00 | (2006.01) | |

(52) U.S. Cl.
CPC ............ *A61K 33/243* (2019.01); *A61K 45/06* (2013.01); *A61K 47/36* (2013.01); *A61K 47/61* (2017.08); *A61P 29/00* (2018.01); *A61P 35/00* (2018.01); *C07D 471/04* (2013.01); *C07F 15/0093* (2013.01)

(58) Field of Classification Search
CPC ........ A61K 47/36; A61P 35/00; C07D 471/04
See application file for complete search history.

(56) References Cited

U.S. PATENT DOCUMENTS

| 4,698,348 A | 10/1987 | Gerster | |
|---|---|---|---|
| 7,884,207 B2 | 2/2011 | Stoermer et al. | |
| 2004/0122231 A1* | 6/2004 | Gerster | C07D 471/04 546/82 |
| 2009/0099161 A1* | 4/2009 | Rice | A61P 31/12 514/228.5 |
| 2014/0274988 A1 | 9/2014 | Lippard et al. | |

OTHER PUBLICATIONS

Larson, P. et al. "Design and Synthesis of N1-Modified Imidazoquinoline Agonists for Selective Activation of Toll-like Receptors 7 and 8" ACS Med. Chem. Lett. 2017, 8, 1148-1152 (Year: 2017).*
Zhang, H. "Specifically Increased Paclitaxel Release in Tumor and Synergetic Therapy by a Hyaluronic Acid-Tocopherol Nanomicelle" et al. ACS Appl. Mater. Interfaces 2017, 9, 20385-20398 (Year: 2017).*
Notice of Allowance on U.S. Appl. No. 16/850,748 DTD May 13, 2022 (8 pages).
Gerster, et al., "Synthesis and Structure—Activity-Relationships of 1H-Imidazo(4,5-c]quinolines That Induce Interferon Production," Journal of Medicinal Chemistry, 2005, vol. 28, No. 2, pp. 3481-3491.
International Search Report and Written Opinion in International Patent Application No. PCT/US2020/028468 dated Sep. 4, 2020, 9 pages.
Larson, et al., "Design and Synthesis of N1-Modified Imidazoquinoline Agonists for Selective Activation of Toll-Like Receptors 7 and 8," ACS Medicinal Chemistry Letters, 2017, vol. 8, pp. 1148-1152.
Non-Final Office Action on U.S. Appl. No. 16/850,748 DTD Jan. 21, 2022 (8 pages).

* cited by examiner

*Primary Examiner* — Andrew S Rosenthal
(74) *Attorney, Agent, or Firm* — Foley & Lardner LLP

(57) ABSTRACT

The present technology is directed to TLR7 and TLR8 agonist compounds, compositions, and methods of using the same for the treatment of cancers and as vaccine adjuvants.

29 Claims, 20 Drawing Sheets

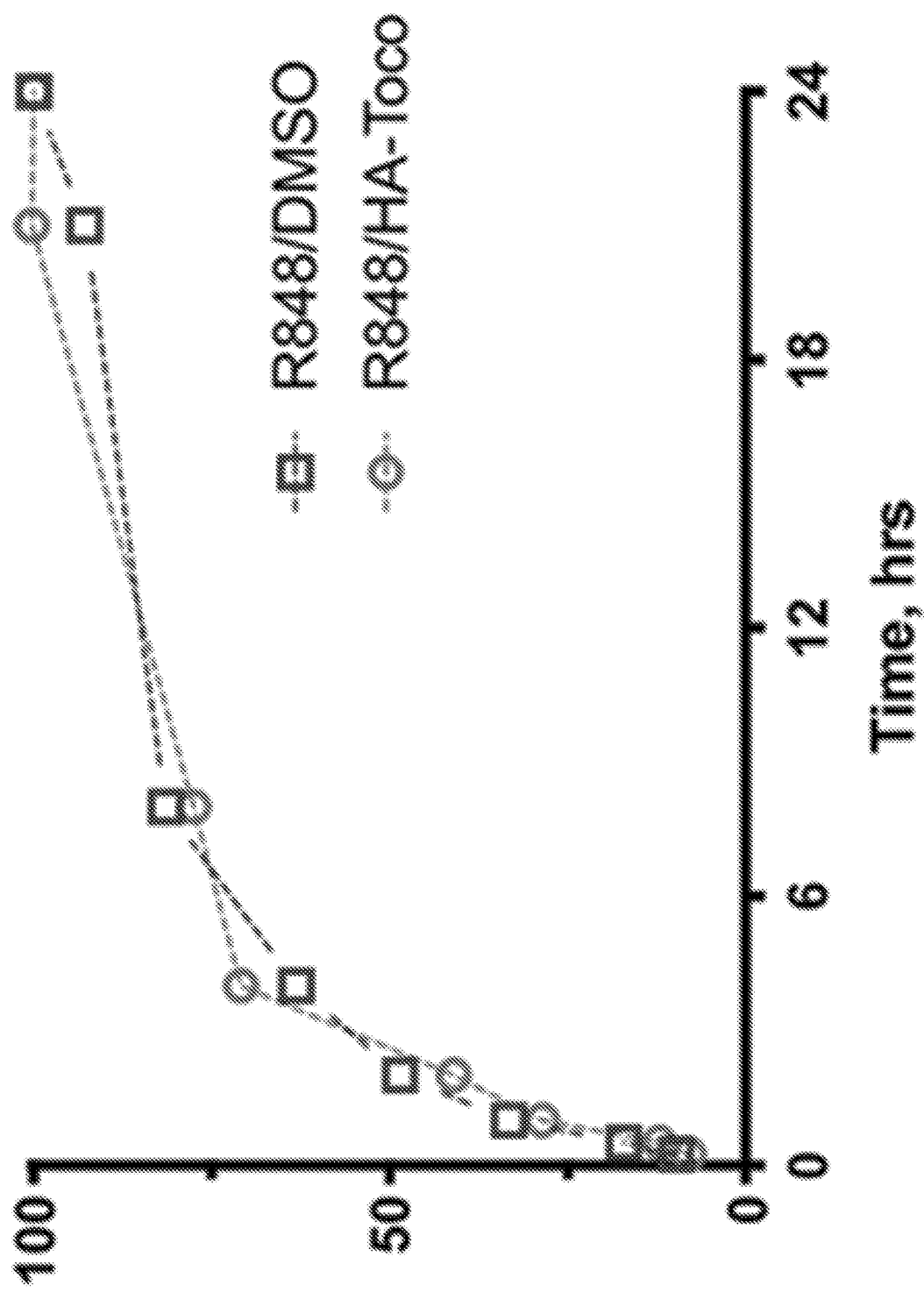

FIG. 12A
FIG. 12B
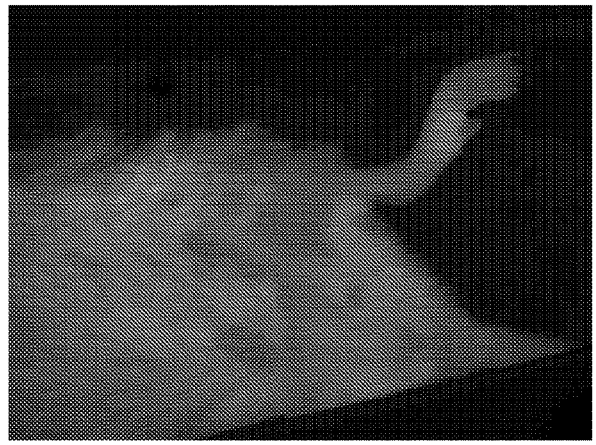
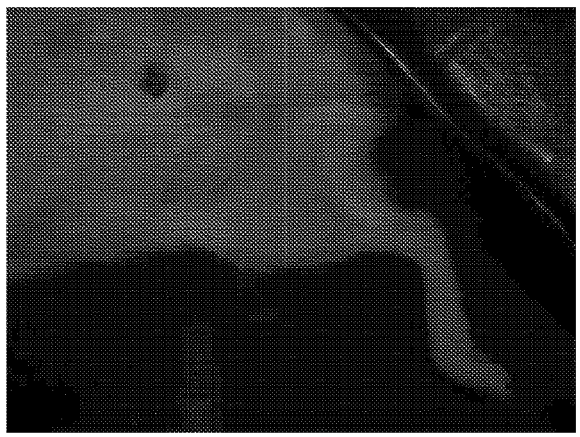
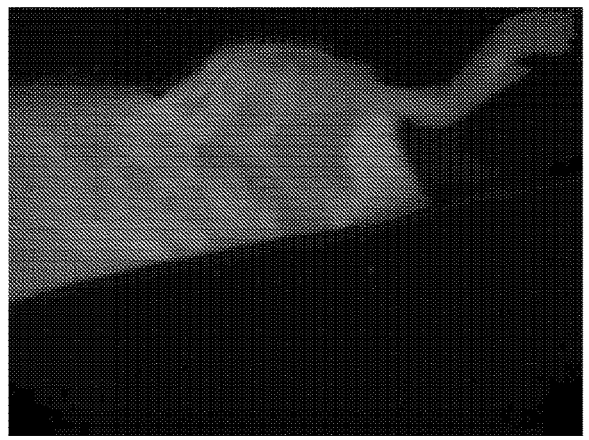
FIG. 12C
FIG. 12D

IMIDAZOQUINOLINE COMPOUNDS AND PRODRUGS THEREOF

CROSS-REFERENCE TO RELATED APPLICATIONS

This application is a U.S. National Phase Application under 35 U.S.C. 371 of International Application No. PCT/US2020/028468, filed Apr. 16, 2020, which claims the benefit of and priority to U.S. Provisional Application 62/835,408, filed Apr. 17, 2019, the entire contents of each of which are incorporated herein by reference.

U.S. GOVERNMENT RIGHTS

This invention was made with government support under CA173292 awarded by the National Institutes of Health. The government has certain rights in the invention.

FIELD

The present technology is directed to compounds, compositions, and methods related to treating tumors and to vaccine adjuvants.

SUMMARY

In an aspect, a compound according to Formula I is provided

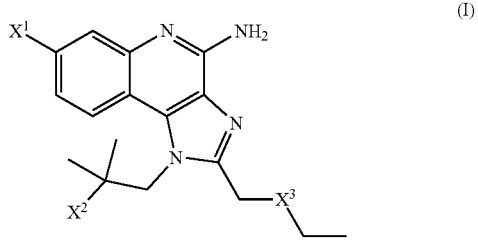

or a pharmaceutically acceptable salt thereof (a "compound of the present technology"), where $X^1$ is H, halo, hydroxy, amino, cyano, trifluoromethyl, thiol, alkylthio, sulfoxide, sulfone, nitro, pentafluorosulfanyl, carboxylate, amide, ester, $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, aryloyloxy,

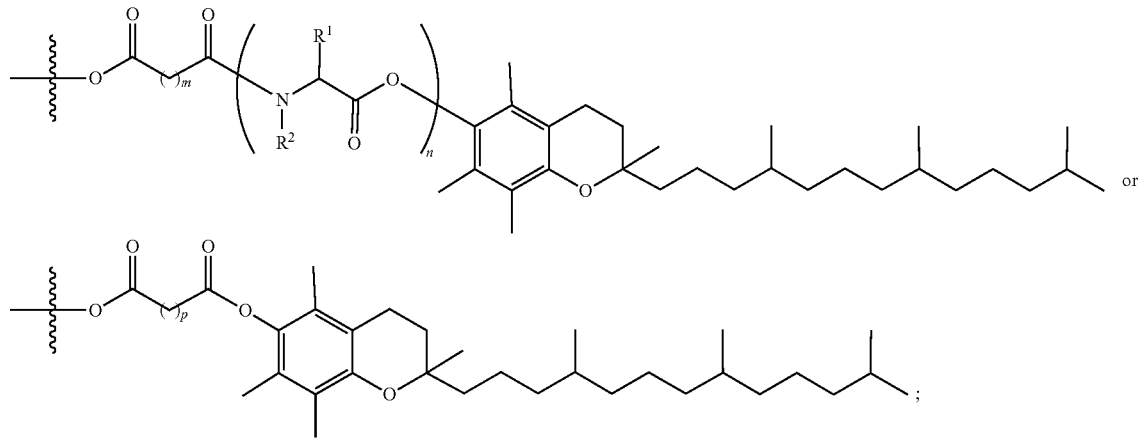

$X^2$ is H, hydroxyl,

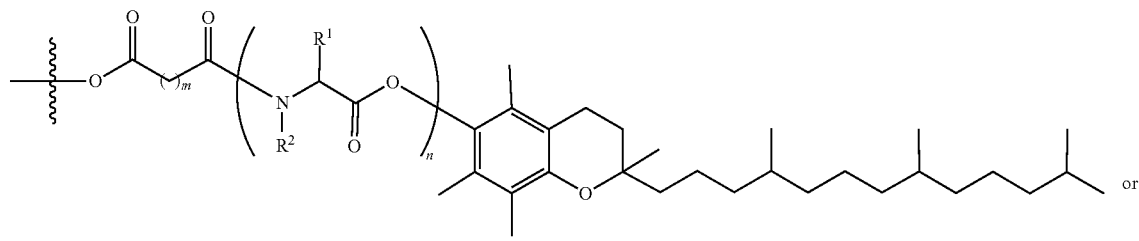

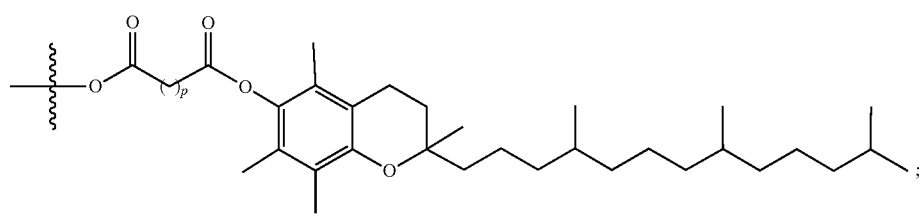

m is 1, 2, 3, 4, 5, 6, 7, or 8; n is 1, 2, or 3; p is 1, 2, 3, 4, 5, 6, 7, or 8; and $X^3$ is $CH_2$ or O; provided that at least one of $X^1$ and $X^2$ is not

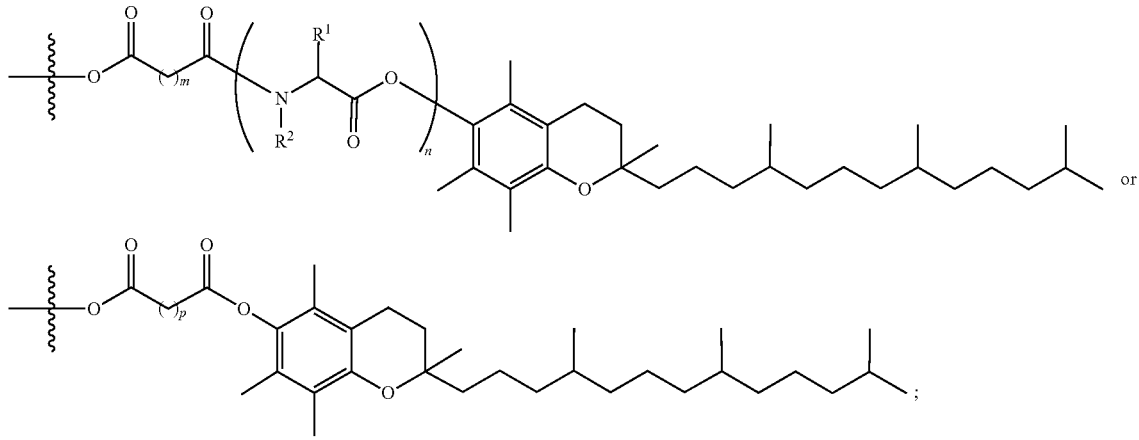

and wherein the compound of Formula I is not

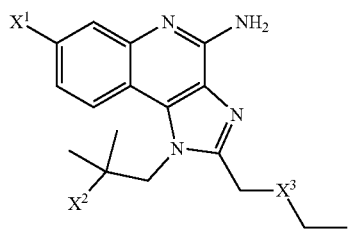

(I)

In a related aspect, a composition is provided that includes a compound of any embodiment disclosed herein of the present technology, a pharmaceutically acceptable carrier, and optionally a hyaluronan-tocopherol conjugate.

In another related aspect, a pharmaceutical composition is provided, the pharmaceutical composition including an effective amount of a compound of any embodiment herein for treating cancer, a tumor, superficial basal cell carcinoma, actinic keratosis, cutaneous T-cell lymphoma, and/or melanoma.

In an aspect a method of treating superficial basal cell carcinoma, actinic keratosis, cutaneous T-cell lymphoma, or melanoma in a subject is provided, where the method includes administering to the subject an effective amount of a compound of any embodiment disclosed herein or administering an effective amount of a composition of any embodiment disclosed herein, wherein the effective amount is an amount effective to treat superficial basal cell carcinoma, actinic keratosis, cutaneous T-cell lymphoma, or melanoma.

In an aspect, a method of slowing or reversing growth of a tumor in a subject is provided, where the method includes administering to the subject an effective amount of a compound of any embodiment disclosed herein or administering an effective amount of a composition of any embodiment disclosed herein, wherein the effective amount is an amount effective to slow or reverse growth of the tumor.

In an aspect, a method of vaccinating a subject is provided, where the method includes administering a vaccine for a disease and administering a vaccine adjuvant, where the vaccine adjuvant includes a compound of any embodiment disclosed herein or a composition of any embodiment disclosed herein.

DESCRIPTION OF THE DRAWINGS

FIG. 3B: IL-12; FIG. 3C: IL-6; and FIG. 3D: IL-10) as measured by ELISA upon treatment of canine peripheral blood mononuclear cells (PBMCs) in culture with compounds of the present technology.

FIGS. 4A-4C show cumulative release profiles of unformulated R848 (resiquimod, 2) dissolved in DMSO, and R848/HA-Toco in PBS (FIG. 4A), pH 7.4. Values are average; unformulated R848-Toco and R848-Toco/HA-Toco in PBS (FIG. 4B), pH 7.4 and unformulated R848-Toco and R848-Toco/HA-Toco in 0.5% Tween 80/PBS (FIG. 4C), pH 7.4. Estimated half-life: R848 (both conditions): 2.5 h; R848-Toco/DMSO: 0.5-2 h; R848-Toco/HA-Toco: 35-40 h. Half-life was estimated based on logarithm-transformed first order model.

FIG. 11 shows remission of a mast cell tumor of a 13-year old Italian Greyhound after two injections.

FIG. 12 shows fluorescence of mouse hind leg injected with Coversin-Alexafluor647 conjugate (Cov647) at 0 hours (FIG. 12A) and 24 hours (FIG. 12C) post injection and injections of Cov647+HA-Toco (33kHAt10) at 0 hours (FIG. 12B) and 24 hours (FIG. 12D) post injection.

DETAILED DESCRIPTION

Figure 1:
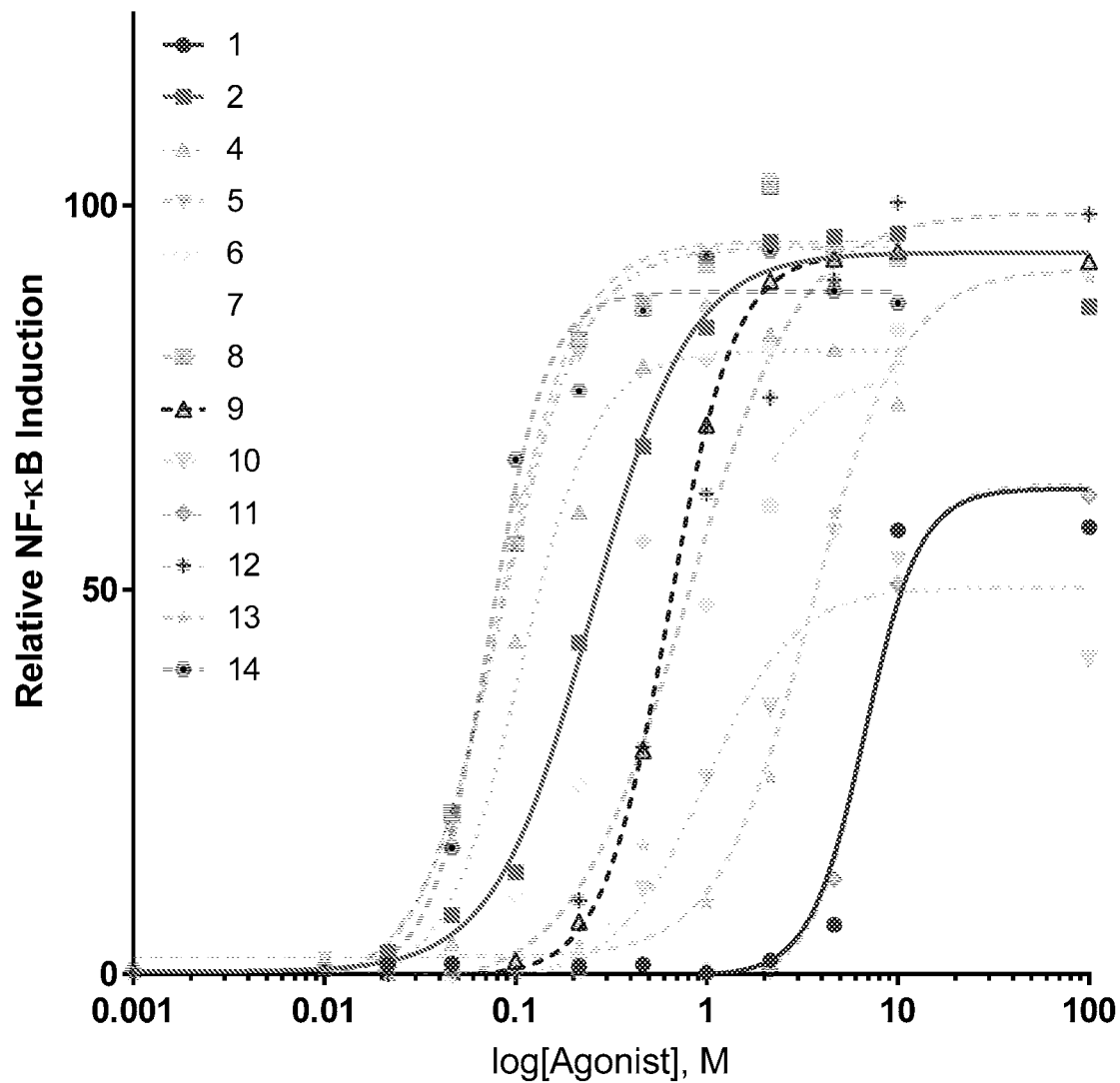
FIG. 1 shows a dose response curve of TLR7 activation for compounds of the present technology.

In various aspects, the present technology provides compounds and methods for agonizing a TLR7 and/or TLR8 receptor ("TLR7 and/or TLR8" abbreviated herein as "TLR7/8"). The compounds provided herein can be formulated into pharmaceutical compositions and medicaments that are useful in the disclosed methods. Also provided is the use of the compounds in preparing pharmaceutical formulations and medicaments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 wt. %" would be understood to mean "9 wt. % to 11 wt. %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups may be substituted or unsubstituted. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, and —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Aryl groups may be substituted or unsubstituted. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). Representative substituted aryl groups may be mono-substituted (e.g., tolyl) or substituted more than once. For example, mono-substituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. Heterocyclyl groups may be substituted or unsubstituted. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. The phrase includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolykazaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be monosubstituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Alkoxy groups may be substituted or unsubstituted. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while "sulfides" include —SR$^{80}$ groups, "sulfoxides" include —S(O)R$^{81}$ groups, "sulfones" include —SO$_2$R$^{82}$ groups, and "sulfonyls" include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$. A "hydroxyalkyl" group is a hydroxyl-substituted alkyl group, such as HO—CH$_2$—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The term "pentafluorosulfanyl" refers to —SF$_5$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

As understood by one of ordinary skill in the art, "molecular weight" (also known as "relative molar mass") is a dimensionless quantity but is converted to molar mass by multiplying by 1 gram/mole or by multiplying by 1 Da—for example, a compound with a weight-average molecular weight of 5,000 has a weight-average molar mass of 5,000 g/mol and a weight-average molar mass of 5,000 Da.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism, and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms. The phrase "and/or" as used in this paragraph and the present disclosure will be understood to mean any one of the recited members individually or a combination of any two or more thereof—for example, "A, B, and/or C" would mean "A, B, C, A and B, A and C, or B and C."

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

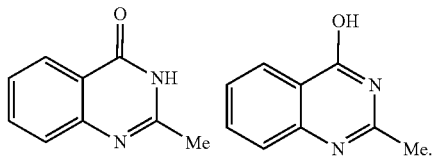

As another example, guanidines may exhibit the following isomeric forms in protic organic solution, also referred to as tautomers of each other:

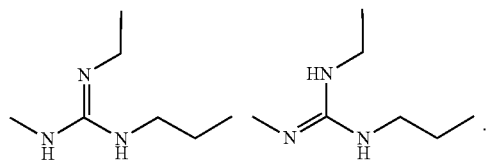

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided subsequent to the Examples section. The disclosures of these publications, patents and published patent specifications are hereby incorporated by reference into the present disclosure to more fully describe the present technology.

The Present Technology

The present technology provides TLR7 and TLR8 agonist compounds, compositions, and methods of using the same for the treatment of cancers and as vaccine adjuvants. Small molecule agonists of TLR7 and/or TLR8 ("TLR7 and/or TLR8" abbreviated herein as "TLR7/8"), such as imidazoquinolines, are validated agonists for the treatment of cancer and for use in vaccine adjuvants.

The drug imiquimod acts upon TLR7. TLR7 has been shown to play a significant role in the pathogenesis of autoimmune disorders. Due to their ability to induce robust production of anti-cancer cytokines such as interleukin-12, TLR7 agonists are also potential tools for cancer immunotherapy. TLR8 agonists (e.g. VTX-2337) have also undergone clinical trials as immune stimulants in combination therapy for some cancers Applicant has discovered compounds demonstrating increased potency and modulated cytokine profiles as compared to known TLR7/8 agonists. For example, compounds of the present technology include agonists up to 4-fold and 2-fold more active than resiquimod for TLR8 and/or TLR7, respectively, and up to 100-fold more active than FDA-approved imiquimod for TLR7.

Thus, in an aspect, a compound according to Formula I is provided

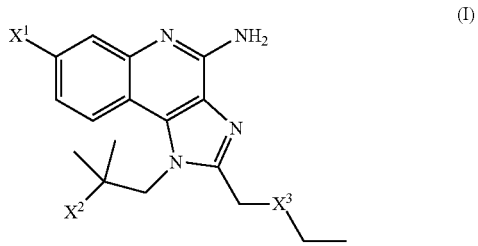

or a pharmaceutically acceptable salt thereof (a "compound of the present technology"), where $X^1$ is H, halo, hydroxy, amino, cyano, trifluoromethyl, thiol, alkylthio, sulfoxide, sulfone, nitro, pentafluorosulfanyl, carboxylate, amide, ester, $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, aryloyloxy,

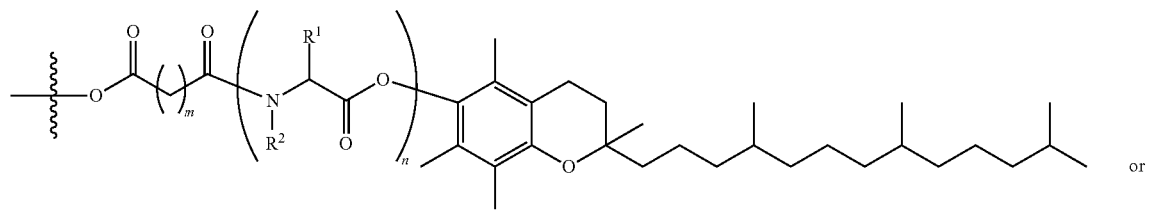 or

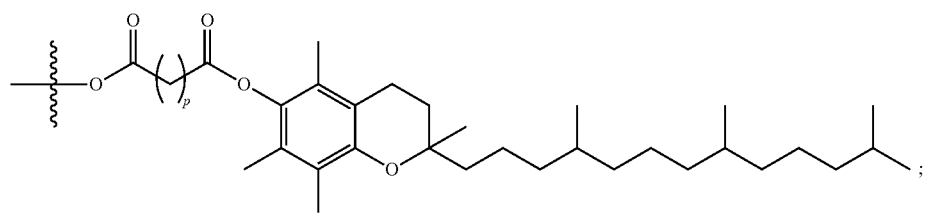;

$X^2$ is H, hydroxyl,

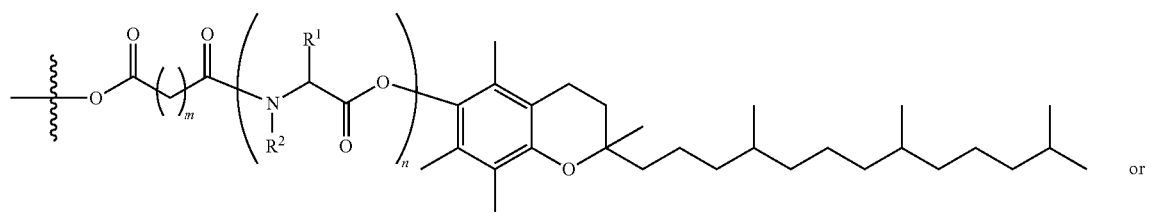 or

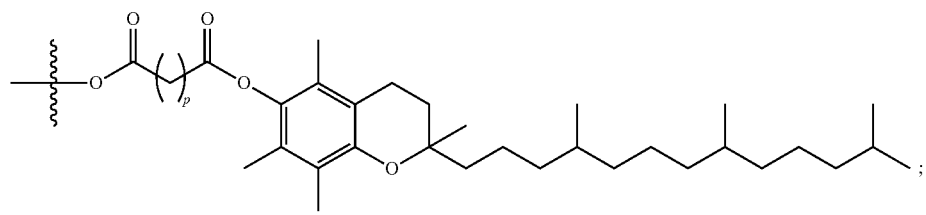;

m is 1, 2, 3, 4, 5, 6, 7, or 8; n is 1, 2, or 3; p is 1, 2, 3, 4, 5, 6, 7, or 8; and
$X^3$ is $CH_2$ or O; provided that at least one of $X^1$ and $X^2$ is not

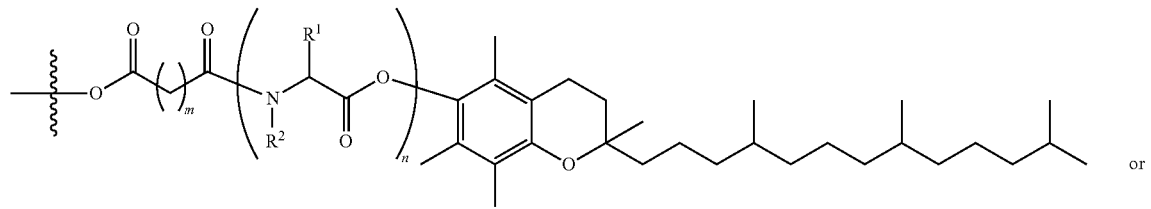 or

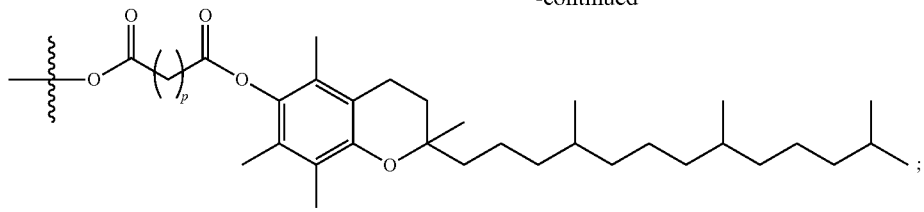
and
wherein the compound of Formula I is not
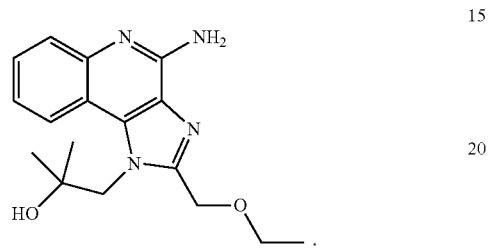
In any embodiment herein, $X^1$ may be H, halo, hydroxy, amino, cyano, thiol, alkylthio, $C_1$-$C_6$ alkyl, $C_1$-$C_6$ alkoxy, aryloxy, $C_1$-$C_8$ alkanoyloxy, aryloyloxy,
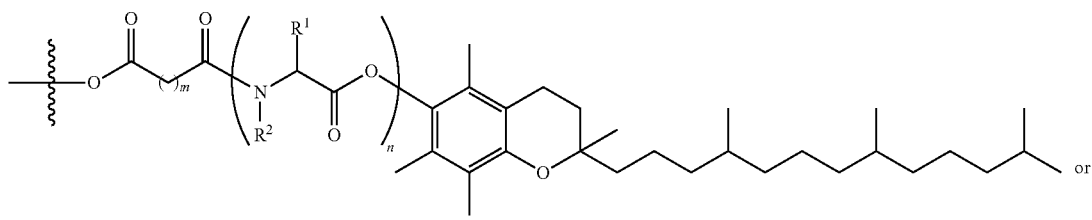
or
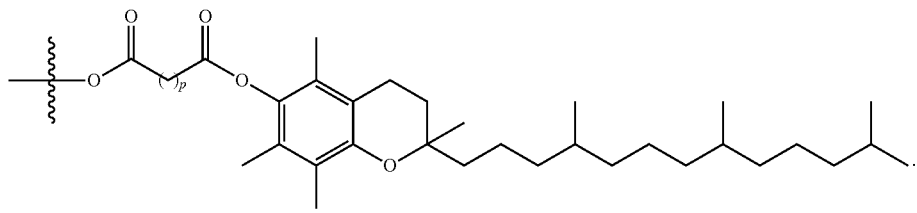
In any embodiment herein, $X^1$ may be H, fluoro, chloro, hydroxy, cyano, $C_1$-$C_6$ alkyl, $C_1$-$C_6$ alkoxy,
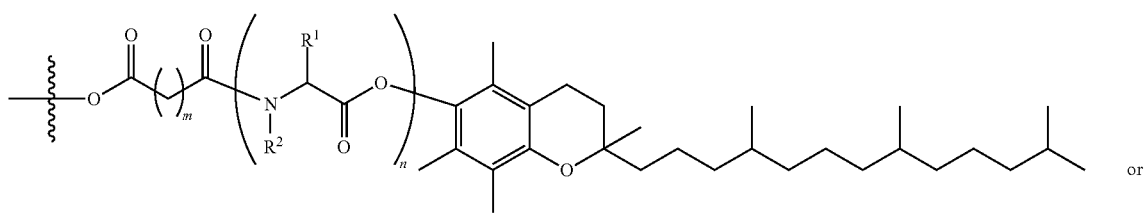
or

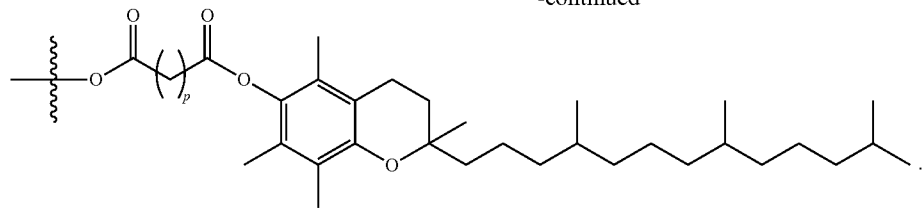

In any embodiment herein, $X^1$ may be H, halo, hydroxy, amino, cyano, thiol, alkylthio, $C_1$-$C_6$ alkyl, $C_1$-$C_6$ alkoxy, aryloxy, $C_1$-$C_8$ alkanoyloxy, or aryloyloxy. In any embodiment herein, $X^1$ may be H, fluoro, chloro, hydroxy, cyano, $C_1$-$C_6$ alkyl, or $C_1$-$C_6$ alkoxy.

In any embodiment herein, it may be one of $X^1$ and $X^2$ is

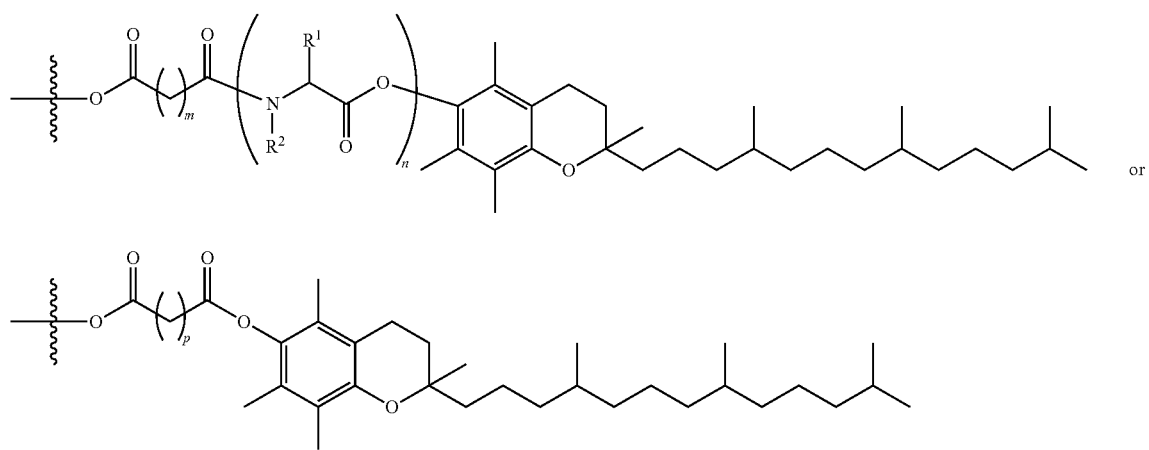

or and the other one of $X^1$ and $X^2$ is not. Thus, in any embodiment herein, it may be one of $X^1$ and $X^2$ is

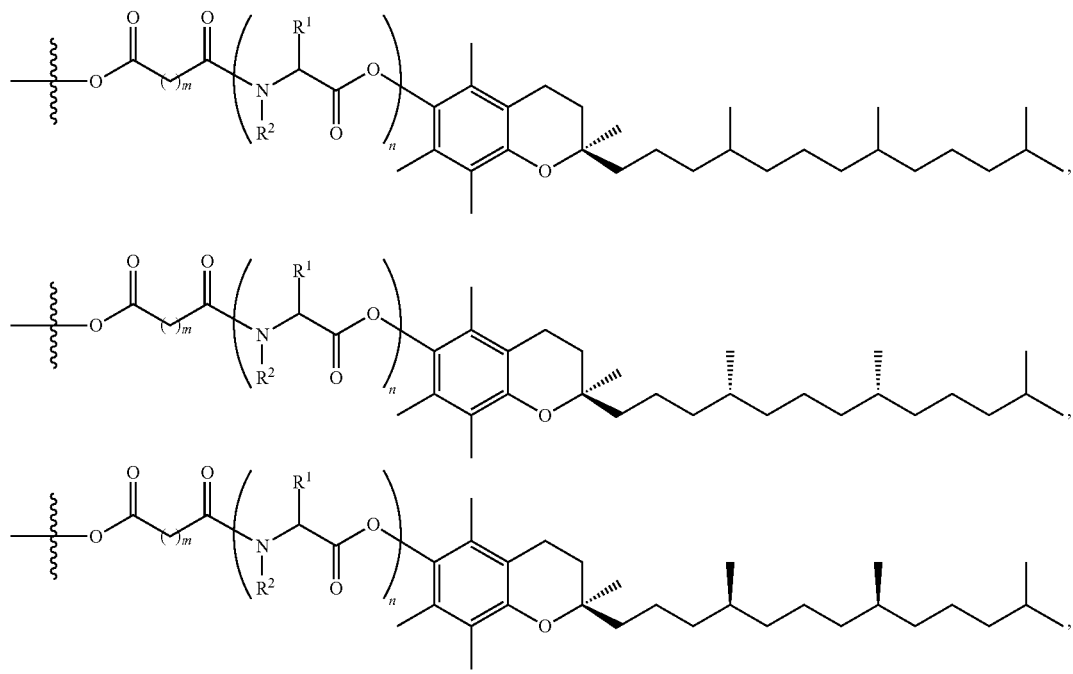

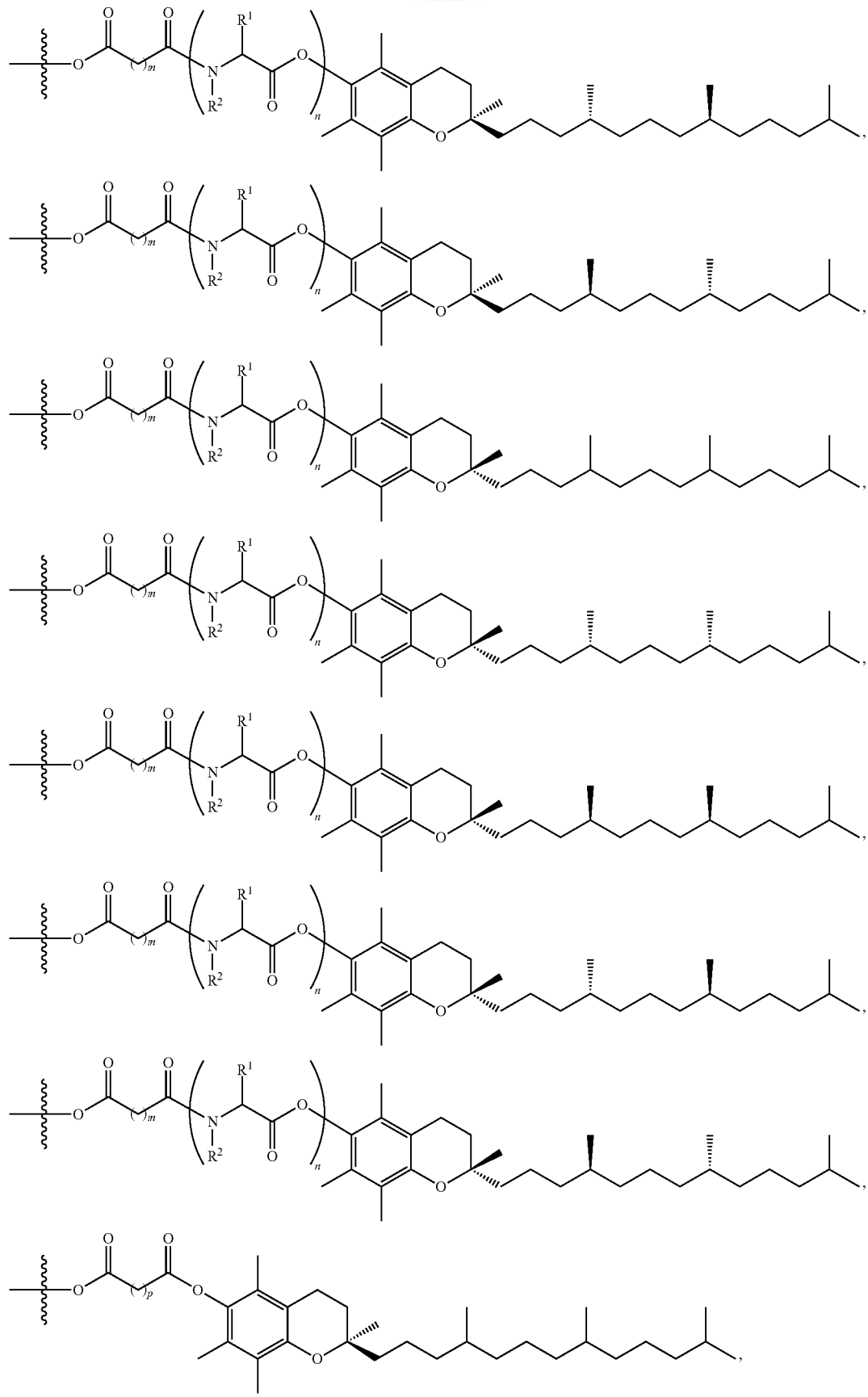

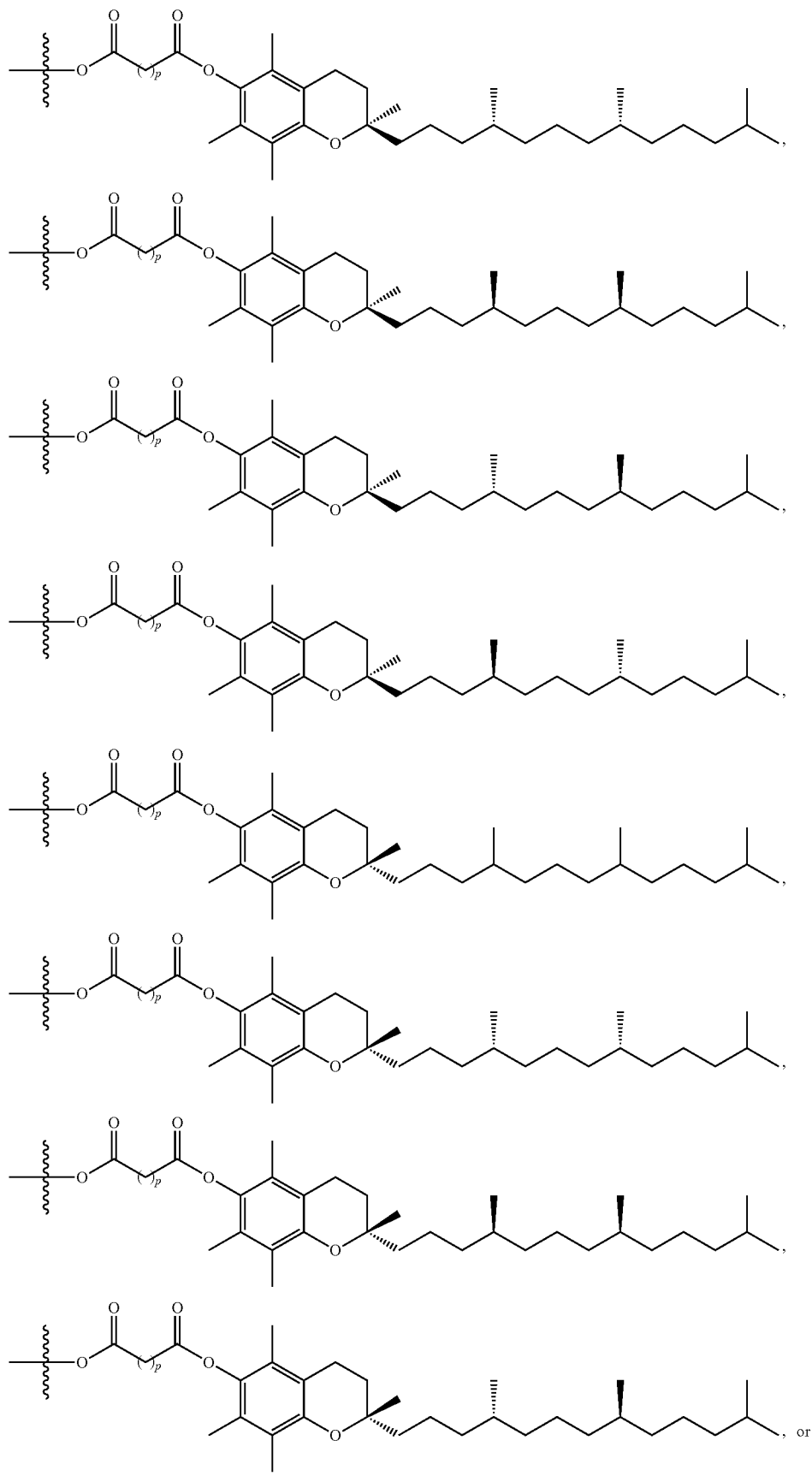

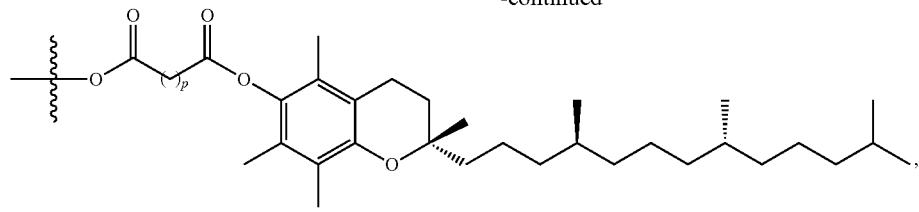
and the other one of $X^1$ and $X^2$ is not.
In any embodiment herein, it may be one of $X^1$ and $X^2$ is
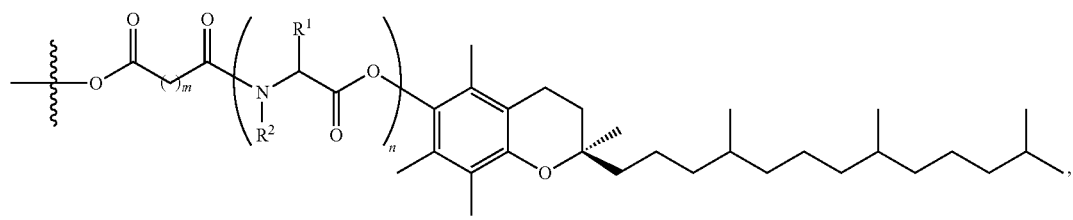
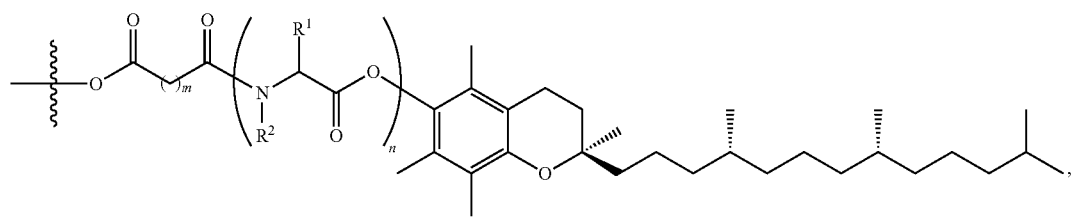
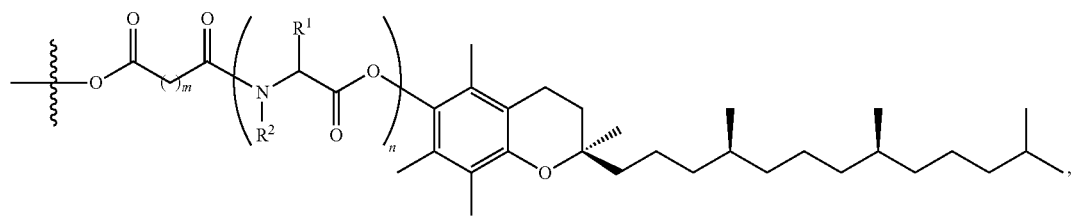
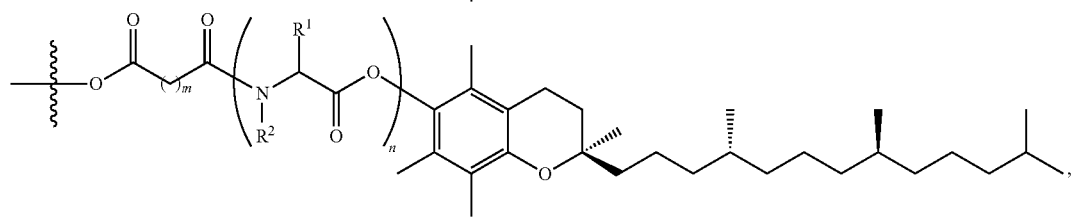
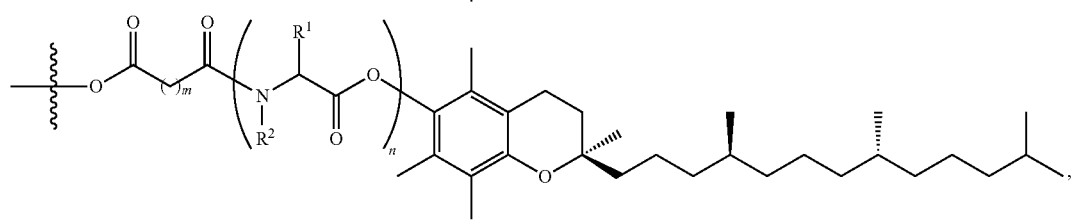
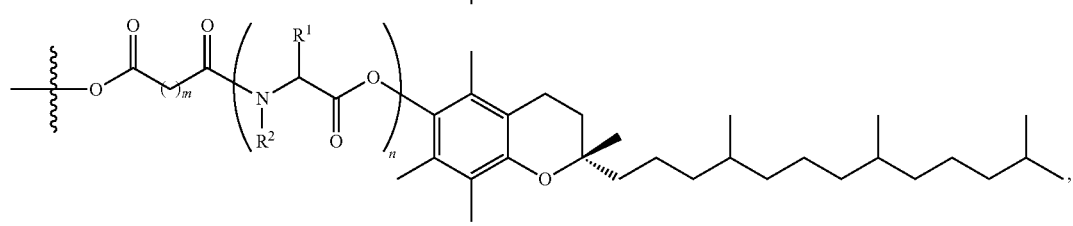

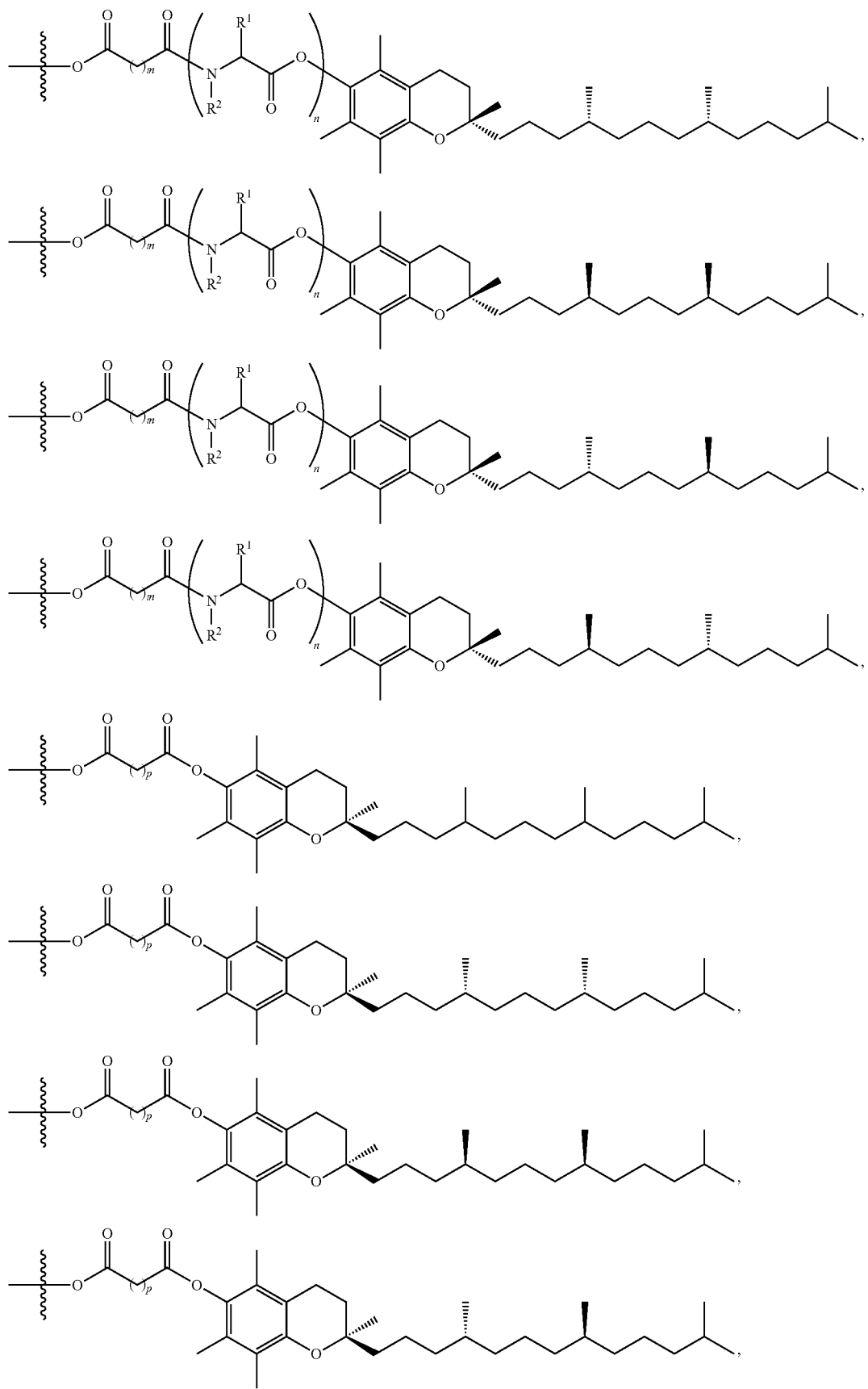

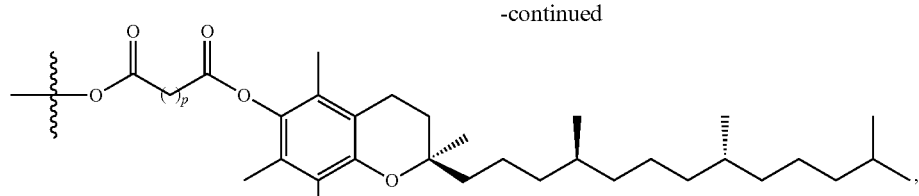
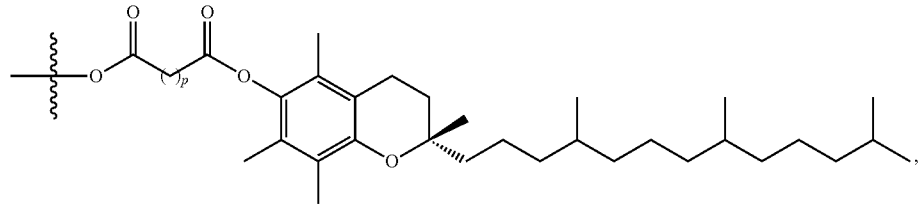
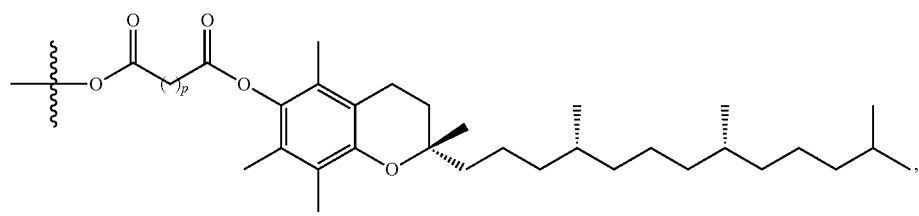
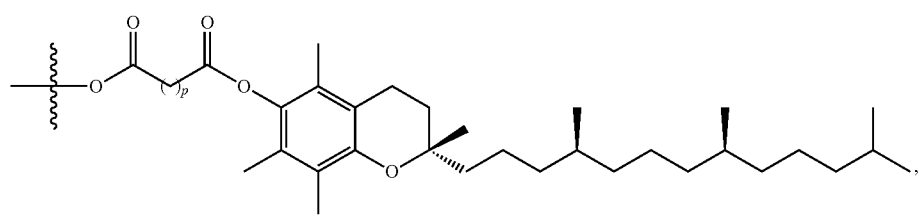
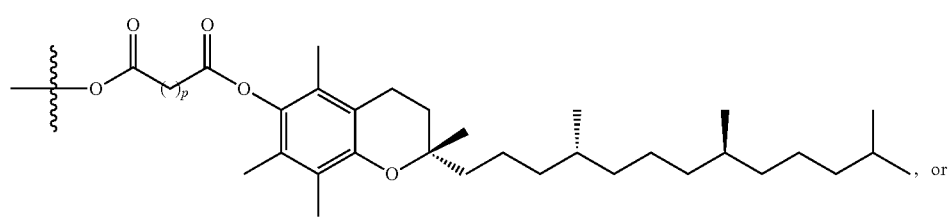, or
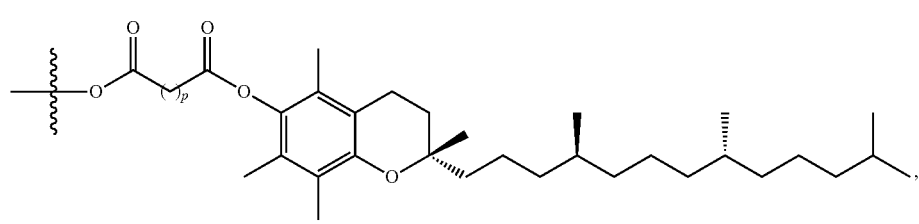
and the other one of $X^1$ and $X^2$ is not.
In any embodiment herein, it may be one of $X^1$ and $X^2$ is
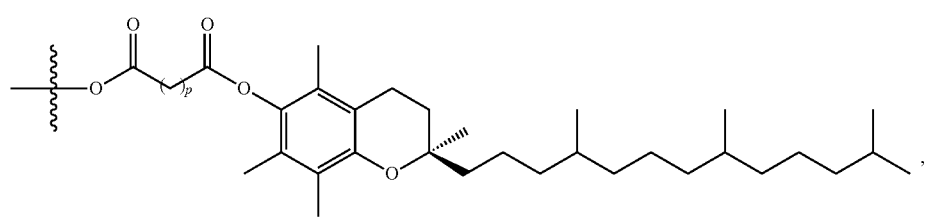

-continued
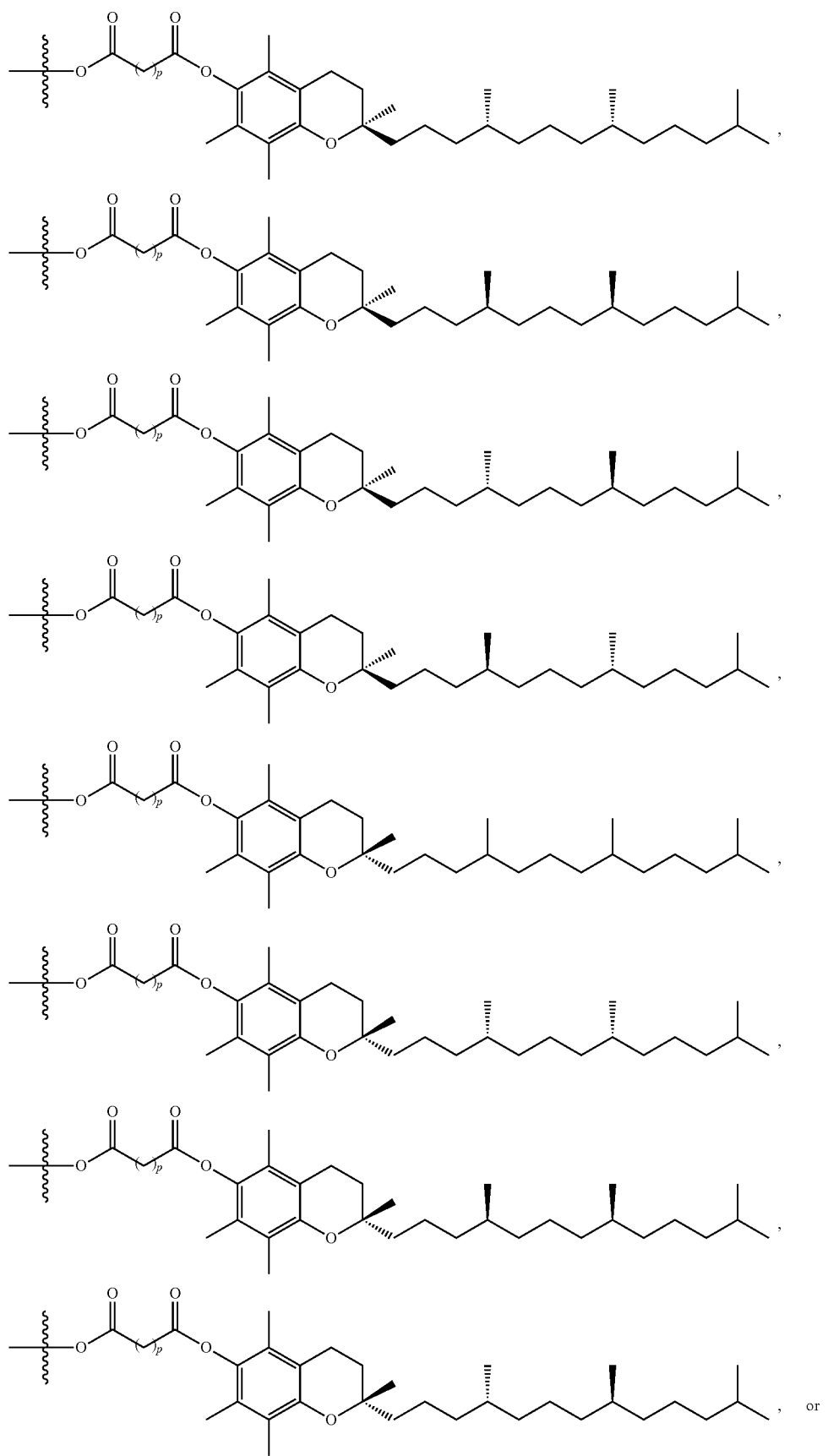

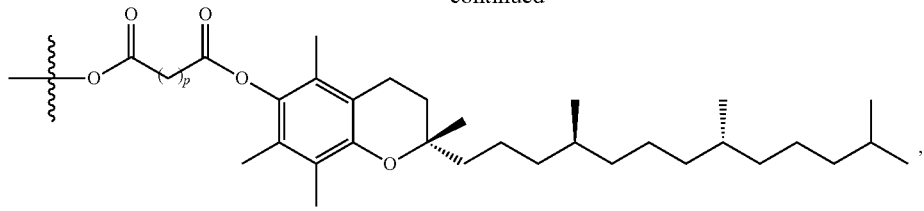

and the other one of $X^1$ and $X^2$ is not.

In any embodiment herein, the compound may be

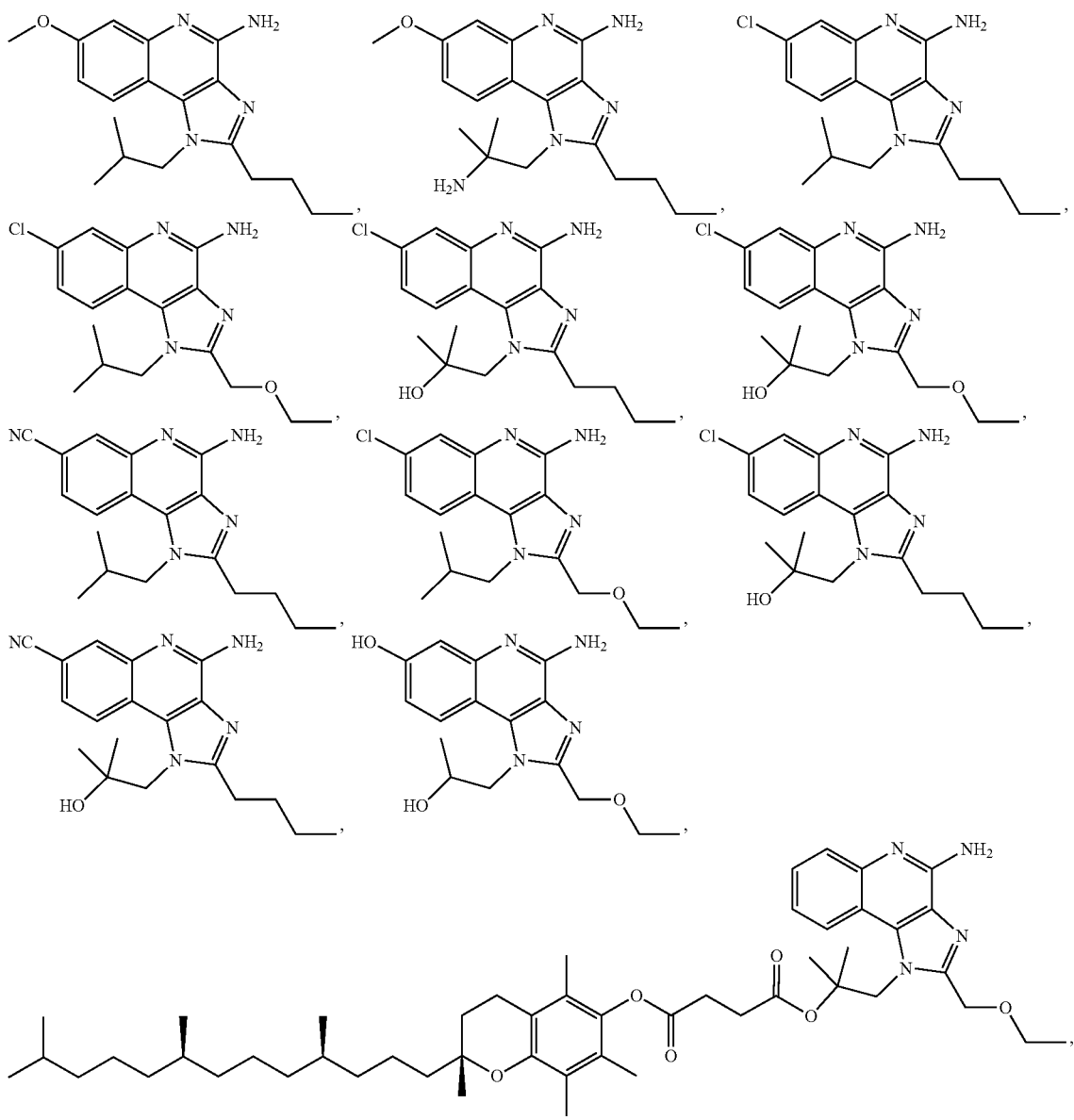

or a pharmaceutically acceptable salt thereof.

In a related aspect, compositions are provided that include a compound of any embodiment disclosed herein and a hyaluronan-tocopherol conjugate. In any embodiment herein, a mass ratio of the compound to the hyaluronan-tocopherol conjugate may be from about 1:15 to about 15:1—thus, the mass ratio may be about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, or any range including and/or in between any two of these values. For example, in any embodiment herein it may be that the mass ratio of the compound (of any embodiment herein) to the hyaluronan-tocopherol conjugate is from about 1:10 to about 5:1, from about 1:5 to about 1:1, or from about 1:3 to about 1:1. In any embodiment herein, it may be that the mass ratio of the compound (of any embodiment herein) to the hyaluronan-tocopherol conjugate is about 1:2.

Hyaluronan (also called hyaluronic acid) is an anionic, nonsulfated glycosaminoglycan distributed widely throughout connective, epithelial, and neural tissues. Hyaluronan has the structure:

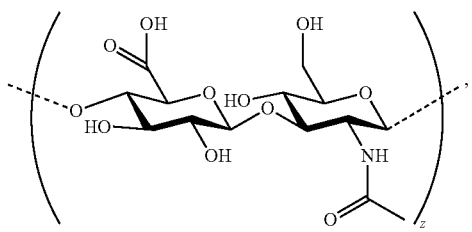

wherein z may be from 1 to 20,000. In any embodiment herein, it may be that the hyaluronan-tocopherol conjugate comprises hyaluronan conjugated to one or more tocopherols by way of one or more of the hyaluronan carboxylate moieties.

Hyaluronan may be isolated from natural sources or synthetically prepared. Isolation of hyaluronan from natural sources is known to those having ordinary skill in the art, for example, as described in Giji, et al., *Adv Food Nutr Res.* 2014; 72:61-77; Ignatova et al., *Pharmaceutical Chemistry Journal* volume 24, pages 211-216 (1990); and Murado, et al., *Food and Bioproducts Processing* Volume 90, Issue 3, July 2012, Pages 491-498; the entire disclosures of which are hereby incorporated by reference. Alternatively, hyaluronan may synthesized as described in Dinkelaar et al., *J. Org. Chem.* 2009, 74, 11, 4208-4216 or Lu et al., *J. Org. Chem.* 2009, 74, 20, 7608-7617; the entire disclosures of which are hereby incorporated by reference.

In any embodiment herein, the hyaluronan of the hyaluronan-tocopherol conjugate may have a weight-average molecular weight (as determined by viscosity, light scattering, gel chromatography, and/or any other suitable method) of about 5,000 to about 2,000,000. Thus, in any embodiment herein, the hyaluronan of the hyaluronan-tocopherol conjugate may have a weight-average molecular weight of about 5,000, about 6,000, about 7,000, about 8,000, about 9,000, about 10,000, about 20,000, about 30,000, about 40,000, about 50,000, about 60,000, about 70,000, about 80,000, about 90,000, about 100,000, about 200,000, about 300,000, about 400,000, about 500,000, about 600,000, about 700,000, about 800,000, about 900,000, about 1,000,000, about 1,500,000, about 2,000,000, or any range including and/or in between any two of these values. For example, in any embodiment herein the hyaluronan of the hyaluronan-tocopherol conjugate may have a weight-average molecular weight of about 5,000 to about 40,000, about 6,000 to about 70,000, about 7,000 to about 150,000, about 8,000 to about 600,000, or about 10,000 to about 2,000,000. One of ordinary skill in the art would understand that particular preparation and measurement methods of a particular hyaluronan may change the weight-average molecular weight, and that the weight-average molecular weight may change as a result of the particular preparation of hyaluronan-tocopherol conjugate and/or preparation of formulations. One of ordinary skill in the art would understand how to account for such changes by suitable modifications of the methods. One of ordinary skill in the art would further understand that a particular hyaluronan may be partially oxidized, partially deacetylated, and/or partially depolymerized.

In any embodiment herein, it may be that the hyaluronan of the hyaluronan-tocopherol conjugate includes hyaluronan that is substituted about 0.1% to about 20% on a molar basis with the tocopherol. Thus, the hyaluronan may be substituted (on a molar basis) with the tocopherol at about 0.1%, about 1%, about 3%, about 4%, about 6%, about 8%, about 10%, about 15%, about 20%, or any range including and/or in between any two of these values. For example, the hyaluronan may be substituted (on a molar basis) with the tocopherol at about 1% to about 10%, at about 6%, or at about 7%.

In any embodiment herein, it may be that the hyaluronan of the hyaluronan-tocopherol conjugate includes hyaluronan that is substituted with the tocopherol at about 0.5 weight % ("wt. %") to about 25 wt. % (based on weight of the hyaluronan moiety in the hyaluronan-tocopherol conjugate)—thus, the hyaluronan may be substituted with the tocopherol at about 0.5 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 15 wt. %, about 20 wt. %, about 25 wt. %, or any range including and/or in between any two of these values. For example, may be substituted with the tocopherol at about 0.5 wt. % to about 5 wt. %, about 1 wt. % to about 10 wt. %, or about 2 wt. % to about 25 wt. %.

In any embodiment herein including a hyaluronan-tocopherol conjugate, it may be that one or more tocopherol is conjugated to hyaluronan by way of the free phenol of the tocopherol. Tocopherols are naturally occurring compounds, which include vitamin E. Food sources with the highest concentrations of vitamin E are vegetable oils, followed by nuts and seeds. Purified tocopherols are available to those having ordinary skill in the art from a variety of commercial sources (Millipore Sigma, BASF). In any embodiment herein including a hyaluronan-tocopherol conjugate, the tocopherol may be a methylated phenol of one or more of the following structures:

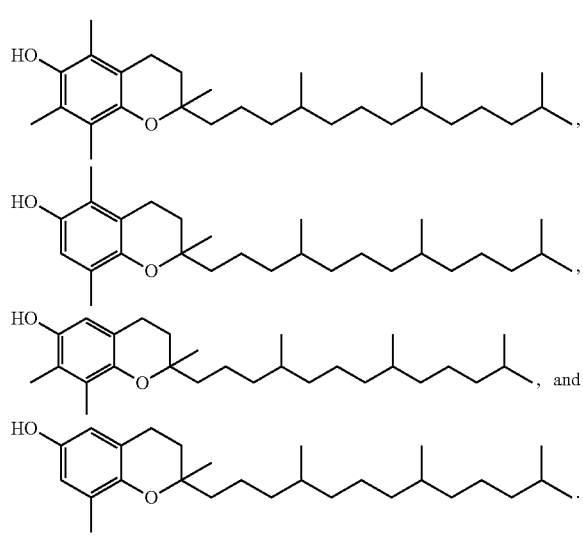

In any embodiment herein, it may be that the hyaluronan-tocopherol conjugate is of Formula II:

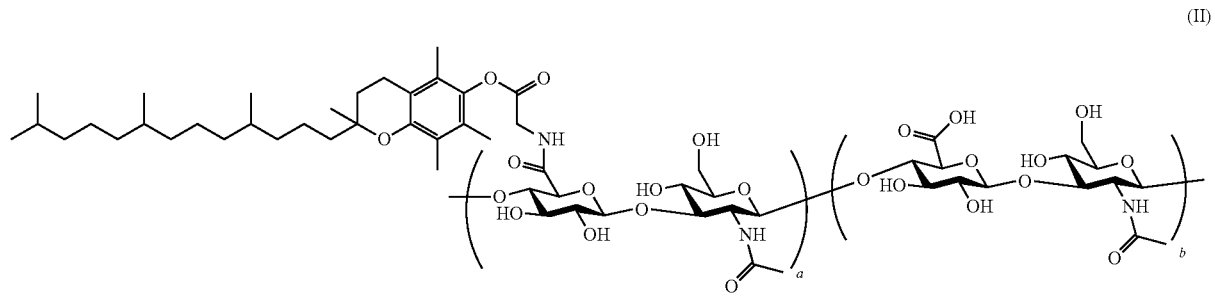

(II)

or a pharmaceutically acceptable salt thereof, wherein a is from 1 to 800 is and b is from 18 to 2540. In any embodiment herein, it may be that the hyaluronan-tocopherol conjugate of Formula II is of Formula IIa:

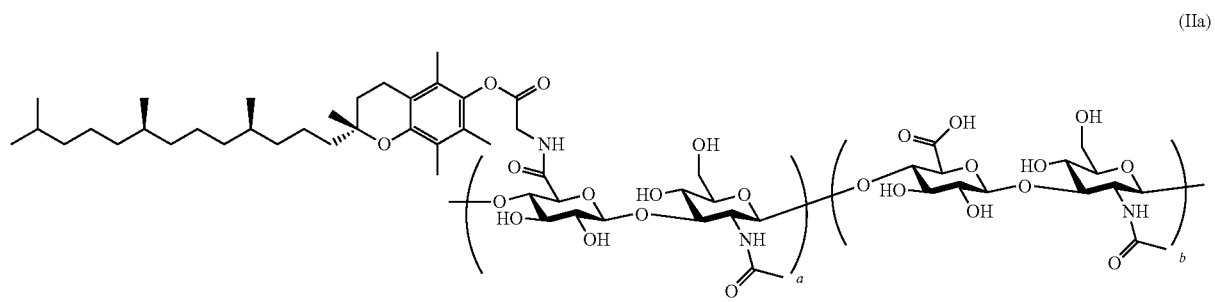

(IIa)

or a pharmaceutically acceptable salt thereof, where a and b are as described for Formula II.

In any embodiment herein, it may be that the hyaluronan-tocopherol conjugate is of Formula III:

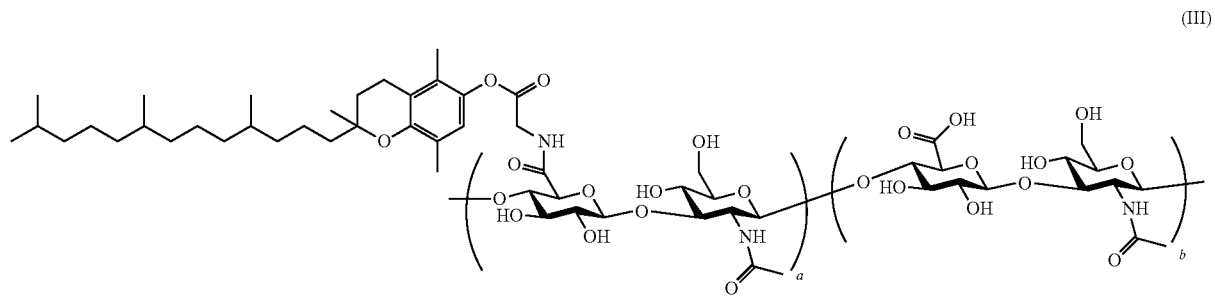

(III)

or a pharmaceutically acceptable salt thereof, wherein a is from 1 to 800 is and b is from 18 to 2540.

In any embodiment herein, it may be that the hyaluronan-tocopherol conjugate is of Formula IV:

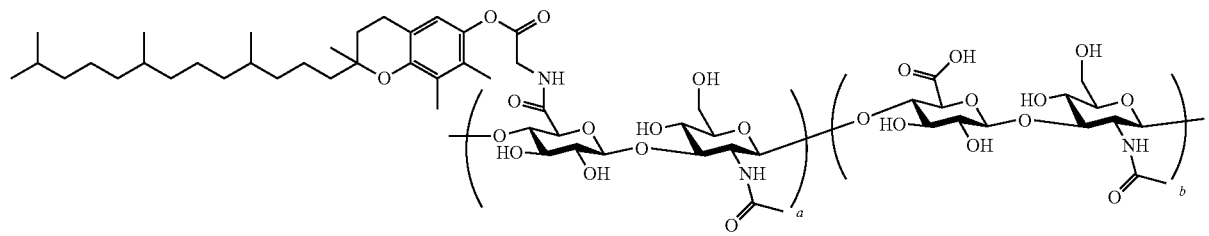

(IV)

or a pharmaceutically acceptable salt thereof, wherein a is from 1 to 800 is and b is from 18 to 2540.

In any embodiment herein, it may be that the hyaluronan-tocopherol conjugate is of Formula V:

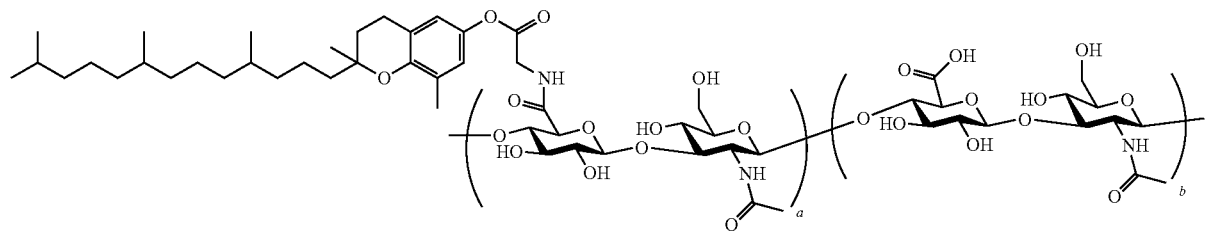

(V)

or a pharmaceutically acceptable salt thereof, wherein a is from 1 to 800 is and b is from 18 to 2540.

In an aspect, a composition is provided that includes a compound of any embodiment disclosed herein, a pharmaceutically acceptable carrier or one or more excipients, fillers or agents (collectively referred to hereafter as "pharmaceutically acceptable carrier" unless otherwise indicated and/or specified), and optionally a hyaluronan-tocopherol conjugate of any embodiment disclosed herein. In a related aspect, a medicament for vaccination or treating a tumor is provided that includes a compound of any embodiment disclosed herein and optionally a hyaluronan-tocopherol conjugate of any embodiment disclosed herein. In a related aspect, a pharmaceutical composition is provided that includes (i) an effective amount of a compound of any embodiment disclosed herein, (ii) a pharmaceutically acceptable carrier, and optionally (iii) a hyaluronan-tocopherol conjugate of any embodiment disclosed herein. For ease of reference, the compositions, medicaments, and pharmaceutical compositions of the present technology may collectively be referred to herein as "compositions." In further related aspects, the present technology provides methods including a compound of any aspect or embodiment disclosed herein, the hyaluronan-tocopherol conjugate of any aspect or embodiment disclosed herein, and/or a composition of any embodiment disclosed herein as well as uses thereof.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, reduction of a tumor mass. In any aspect or embodiment disclosed herein (collectively referred to herein as "any embodiment herein," "any embodiment disclosed herein," or the like) of the compositions, pharmaceutical compositions, and methods including compounds of the present technology, the effective amount may be an amount effective in treating a cancer, treating a tumor, and/or shrinking a tumor. The cancer may be (and the tumor may be of a cancer such as) squamous cell carcinoma, soft tissue sarcoma, oral melanoma, acute lymphoblastic leukemia (ALL), acute myeloid leukemia (AML), adrenocortical carcinoma, AIDS-related cancers, Kaposi sarcoma (soft tissue sarcoma), AIDS-related lymphoma (lymphoma), anal cancer, appendix cancer, gastrointestinal carcinoid tumors, astrocytomas, atypical teratoid/rhabdoid tumor, basal cell carcinoma of the skin, bile duct cancer, bladder cancer, bone cancer (includes Ewing Sarcoma and Osteosarcoma and Malignant Fibrous Histiocytoma), brain tumors, breast cancer, bronchial tumors (lung cancer), Burkitt lymphoma, carcinoid tumor (gastrointestinal), carcinoma of unknown primary, cardiac (heart) tumors, childhood brain cancer, germ cell tumor, primary CNS lymphoma, cervical cancer, cholangiocarcinoma, chordoma, chronic lymphocytic leukemia (CLL), chronic myelogenous leukemia (CIVIL), chronic myeloproliferative neoplasms, colorectal cancer, craniopharyngioma, cutaneous T-cell lymphoma, ductal carcinoma in situ (DCIS), embryonal tumors, medulloblastoma, endometrial cancer (uterine cancer), ependymoma, esophageal cancer, esthesioneuroblastoma (head and neck cancer), extracranial germ cell tumor, eye cancer, retinoblastoma, fallopian tube cancer, fibrous histiocytoma of bone, osteosarcoma, gallbladder cancer, gastric (stomach) cancer, gastrointestinal stromal tumors (GIST) (soft tissue sarcoma), germ cell tumors, childhood central nervous system germ cell tumors (brain cancer), childhood extracranial germ cell tumors, extragonadal germ cell tumors, ovarian germ cell tumors, testicular cancer, gestational trophoblastic disease, hairy cell leukemia, head and neck cancer, heart tumors, hepatocellular (liver) cancer, histiocytosis, Hodgkin lymphoma, intraocular melanoma, islet cell tumors, pancreatic neuroendocrine tumors, kidney (renal cell) cancer, Langerhans cell histiocytosis, laryngeal cancer (head and neck cancer), leukemia, lip and oral cavity cancer (head and neck cancer), liver cancer, lung cancer, lymphoma, male breast cancer, malignant fibrous histiocytoma of bone and osteosarcoma, melanoma, Merkel cell carcinoma (skin cancer), mesothelioma, metastatic cancer, metastatic squamous neck cancer with occult primary (head and neck cancer), midline tract carcinoma with nut gene changes, mouth cancer (head and neck cancer), multiple endocrine neoplasia syndromes, multiple myeloma/plasma cell neoplasms, mycosis fungoides (lymphoma), myelodysplastic syndromes, myelogenous leukemia, myeloid leukemia, myeloproliferative neoplasms, nasal cavity and paranasal sinus cancer (head and neck cancer), nasopharyngeal cancer (head and neck cancer), neuroblastoma, non-Hodgkin lymphoma, non-small cell lung cancer, oral cancer, osteosarcoma and malignant fibrous histiocytoma of bone, ovarian cancer, pancreatic cancer, pancreatic neuroendocrine tumors (islet cell tumors), papillomatosis (childhood laryngeal), paraganglioma, paranasal sinus and nasal cavity cancer (head and neck cancer), parathyroid cancer, penile cancer, pharyngeal cancer (head and neck cancer), pheochromocytoma, pituitary tumor, plasma cell neoplasm/multiple myeloma, pleuropulmonary blastoma (lung cancer), pregnancy and breast cancer, primary central nervous system (CNS) lymphoma, primary peritoneal cancer, prostate cancer, rectal cancer, recurrent cancer, renal cell (kidney) cancer, rhabdomyosarcoma, salivary gland cancer (head and neck cancer), sarcoma, childhood rhabdomyosarcoma, childhood vascular tumors, Ewing sarcoma (bone cancer), Kaposi sarcoma, osteosarcoma (bone cancer), Sézary syndrome (lymphoma), skin cancer, small cell lung cancer, small intestine cancer, squamous cell carcinoma of the skin, squamous neck cancer with occult primary, metastatic (head and neck cancer), stomach (gastric) cancer, T-cell lymphoma, throat cancer (head and neck cancer), oropharyngeal cancer, hypopharyngeal cancer, thymoma and thymic carcinoma, thyroid cancer, tracheobronchial tumors (lung cancer), transitional cell cancer of the renal pelvis and ureter (kidney (renal cell) cancer), urethral cancer, uterine cancer, uterine sarcoma, vaginal cancer, vascular tumors, vulvar cancer, and/or Wilms tumor and other childhood kidney tumors. By way of example, the effective amount of any embodiment herein including a compound of the present technology may be from about 0.01 µg to about 200 mg of the compound (such as from about 0.1 µg to about 50 mg of the compound or about 10 µg to about 20 mg of the compound). The methods and uses according to the present technology may include an effective amount of a compound of any embodiment disclosed herein. In any aspect or embodiment disclosed herein, the effective amount may be determined in relation to a subject. As used herein, a "subject" or "patient" is a mammal, such as a cat, dog, rodent or primate. Typically the subject is a human, and, preferably, a human suffering from or suspected of suffering from pain. The term "subject" and "patient" can be used interchangeably.

Thus, the instant present technology provides pharmaceutical compositions and medicaments including a compound of any embodiment disclosed herein (or a composition of any embodiment disclosed herein) and a pharmaceutically acceptable carrier. The compositions may be used in the methods and treatments described herein. The pharmaceutical composition may be packaged in unit dosage form. The unit dosage form is effective in treating a tumor by reducing a tumor and/or effective as a vaccine adjuvant when administered to a subject in need thereof. Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1\times10^{-4}$ g/kg to 1 g/kg, preferably, $1\times10^{-3}$ g/kg to 1.0 g/kg. Dosage of a compound of the present technology may also vary from 0.01 mg/kg to 100 mg/kg or, preferably, from 0.1 mg/kg to 10 mg/kg. Suitable unit dosage forms, include, but are not limited to parenteral solutions, oral solutions, powders, tablets, pills, gelcaps, capsules, lozenges, suppositories, patches, nasal sprays, injectables, implantable sustained-release formulations, mucoadherent films, topical varnishes, lipid complexes, liquids, etc.

The pharmaceutical compositions and medicaments may be prepared by mixing one or more compounds and/or compositions of the present technology with pharmaceutically acceptable carriers, excipients, binders, diluents or the like. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remington's Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until, for example, there is a reduction in the mass of a tumor in a subject. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the cancer associated with the tumor, and the pharmacological activity of the compound being used. The determination of optimum dosages for a particular patient is well known to those skilled in the art.

Various assays and model systems can be readily employed to determine the therapeutic effectiveness of the treatment according to the present technology. Effectiveness of the compositions (as well as determination of effective amounts) and methods of the present technology may also be demonstrated by a decrease in the mass of a tumor or slowing the growth of a tumor or, for a vaccine adjuvant, generation of specific antibodies (e.g., generation of IgG specific for epitopes found in significant amounts on a cancer and/or tumor, but where such epitopes are absent or less prevalent in non-cancerous tissues). Effectiveness of a vaccine adjuvant may be shown by, e.g., increased levels of CD8 positive T-cells, a decrease in the amount of T regulatory cells, and/or an increase in natural killer cells. By way of another example, effectiveness of a vaccine adjuvant may be shown by an increase in macrophage cells or dendritic cells with an inflammatory profile, for example increased levels of IL12 and/or Interferon gamma. By way of a further example, effectiveness of a vaccine adjuvant may be shown by increased levels of inflammatory cytokines in the tumor, such as TNF alpha and/or IL6.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The compounds of the present technology can also be administered to a patient along with other conventional therapeutic agents that may be useful in the treatment of tumors or in vaccination. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also include administering, either sequentially or in combination with one or more compounds of the present technology, a conventional therapeutic agent in an amount that can potentially or synergistically be effective for the treatment of tumors or in vaccination.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1 \times 10^{-4}$ g/kg to 1 g/kg, preferably, $1 \times 10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In another aspect, the present technology provides methods of identifying a target of interest including contacting the target of interest with a detectable or imaging effective quantity of a labeled compound of the present technology. A detectable or imaging effective quantity is a quantity of a labeled compound of the present technology necessary to be detected by the detection method chosen. For example, a detectable quantity can be an administered amount sufficient to enable detection of binding of the labeled compound to a target of interest including, but not limited to, a TLR7 and/or TLR8. Suitable labels are known by those skilled in the art and can include, for example, radioisotopes, radionuclides, isotopes, fluorescent groups, biotin (in conjunction with streptavidin complexation), and chemiluminescent groups. Upon binding of the labeled compound to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

As indicated previously in this disclosure, in an aspect a method of treating superficial basal cell carcinoma, actinic keratosis, cutaneous T-cell lymphoma, or melanoma in a subject is provided, where the method includes administering to the subject an effective amount of a compound of any embodiment disclosed herein or administering an effective amount of a composition of any embodiment disclosed herein, wherein the effective amount is an amount effective to treat superficial basal cell carcinoma, actinic keratosis, cutaneous T-cell lymphoma, or melanoma. In any embodiment herein of the method, the administering may include oral administration or topical administration.

In an aspect, a method of treating cancer in a subject is provided, where the method includes administering to the subject an effective amount of a compound of any embodiment disclosed herein or administering an effective amount of a composition of any embodiment disclosed herein, wherein the effective amount is an amount effective to treat the cancer. The cancer may be squamous cell carcinoma, soft tissue sarcoma, oral melanoma, acute lymphoblastic leukemia (ALL), acute myeloid leukemia (AML), adrenocortical carcinoma, AIDS-related cancers, Kaposi sarcoma (soft tissue sarcoma), AIDS-related lymphoma (lymphoma), anal cancer, appendix cancer, gastrointestinal carcinoid tumors, astrocytomas, atypical teratoid/rhabdoid tumor, basal cell carcinoma of the skin, bile duct cancer, bladder cancer, bone cancer (includes Ewing Sarcoma and Osteosarcoma and Malignant Fibrous Histiocytoma), brain tumors, breast cancer, bronchial tumors (lung cancer), Burkitt lymphoma, carcinoid tumor (gastrointestinal), carcinoma of unknown primary, cardiac (heart) tumors, childhood brain cancer, germ cell tumor, primary CNS lymphoma, cervical cancer, cholangiocarcinoma, chordoma, chronic lymphocytic leukemia (CLL), chronic myelogenous leukemia (CIVIL), chronic myeloproliferative neoplasms, colorectal cancer, craniopharyngioma, cutaneous T-cell lymphoma, ductal carcinoma in situ (DCIS), embryonal tumors, medulloblastoma, endometrial cancer (uterine cancer), ependymoma, esophageal cancer, esthesioneuroblastoma (head and neck cancer), extracranial germ cell tumor, eye cancer, retinoblastoma, fallopian tube cancer, fibrous histiocytoma of bone, osteosarcoma, gallbladder cancer, gastric (stomach) cancer, gastrointestinal stromal tumors (GIST) (soft tissue sarcoma), germ cell tumors, childhood central nervous system germ cell tumors (brain cancer), childhood extracranial germ cell tumors, extragonadal germ cell tumors, ovarian germ cell tumors, testicular cancer, gestational trophoblastic disease, hairy cell leukemia, head and neck cancer, heart tumors, hepatocellular (liver) cancer, histiocytosis, Hodgkin lymphoma, intraocular melanoma, islet cell tumors, pancreatic neuroendocrine tumors, kidney (renal cell) cancer, Langerhans cell histiocytosis, laryngeal cancer (head and neck cancer), leukemia, lip and oral cavity cancer (head and neck cancer), liver cancer, lung cancer, lymphoma, male breast cancer, malignant fibrous histiocytoma of bone and osteosarcoma, melanoma, Merkel cell carcinoma (skin cancer), mesothelioma, metastatic cancer, metastatic squamous neck cancer with occult primary (head and neck cancer), midline tract carcinoma with nut gene changes, mouth cancer (head and neck cancer), multiple endocrine neoplasia syndromes, multiple myeloma/plasma cell neoplasms, mycosis fungoides (lymphoma), myelodysplastic syndromes, myelogenous leukemia, myeloid leukemia, myeloproliferative neoplasms, nasal cavity and paranasal sinus cancer (head and neck cancer), nasopharyngeal cancer (head and neck cancer), neuroblastoma, non-Hodgkin lymphoma, non-small cell lung cancer, oral cancer, osteosarcoma and malignant fibrous histiocytoma of bone, ovarian cancer, pancreatic cancer, pancreatic neuroendocrine tumors (islet cell tumors), papillomatosis (childhood laryngeal), paraganglioma, paranasal sinus and nasal cavity cancer (head and neck cancer), parathyroid cancer, penile cancer, pharyngeal cancer (head and neck cancer), pheochromocytoma, pituitary tumor, plasma cell neoplasm/multiple myeloma, pleuropulmonary blastoma (lung cancer), pregnancy and breast cancer, primary central nervous system (CNS) lymphoma, primary peritoneal cancer, prostate cancer, rectal cancer, recurrent cancer, renal cell (kidney) cancer, rhabdomyosarcoma, salivary gland cancer (head and neck cancer), sarcoma, childhood rhabdomyosarcoma, childhood vascular tumors, Ewing sarcoma (bone cancer), Kaposi sarcoma, osteosarcoma (bone cancer), Sézary syndrome (lymphoma), skin cancer, small cell lung cancer, small intestine cancer, squamous cell carcinoma of the skin, squamous neck cancer with occult primary, metastatic (head and neck cancer), stomach (gastric) cancer, T-cell lymphoma, throat cancer (head and neck cancer), oropharyngeal cancer, hypopharyngeal cancer, thymoma and thymic carcinoma, thyroid cancer, tracheobronchial tumors (lung cancer), transitional cell cancer of the renal pelvis and ureter (kidney (renal cell) cancer), urethral cancer, uterine cancer, uterine sarcoma, vaginal cancer, vascular tumors, vulvar cancer, and/or Wilms tumor and other childhood kidney tumors.

In any embodiment herein, the administering may further include administration of a chemotherapeutic agent such as an alkylating agent; a nitrosourea; an antimetabolite; an anthracycline; a topoisomerase II inhibitor; a mitotic inhibitor; an anti-estrogen; a progestin; an aromatase inhibitor; an anti-androgen; an LHRH agonist; a corticosteroid hormone; a DNA alkylating agent; a taxane; a *vinca* alkaloid; a microtubule poison, or a combination of any two or more thereof. In any embodiment herein, the administering may further include administration of a chemotherapeutic agent such as busulfan, cisplatin, carboplatin, oxaliplatin, an octahedral platinum (IV) compound, chlorambucil, cyclophosphamide, ifosfamide, dacarbazine (DTIC), mechlorethamine (nitrogen mustard), melphalan, temozolomide, carmustine (BCNU), lomustine (CCNU), 5-fluorouracil, capecitabine, 6-mercaptopurine, methotrexate, gemcitabine, cytarabine (ara-C), fludarabine, pemetrexed, daunorubicin, doxorubicin (Adriamycin), epirubicin, idarubicin, mitoxantrone, topotecan, irinotecan, etoposide (VP-16), teniposide, paclitaxel, docetaxel, vinblastine, vincristine, vinorelbine, prednisone, dexamethasone, L-asparaginase, dactinomycin, thalidomide, tretinoin, imatinib (Gleevec), gefitinib (Iressa), erlotinib (Tarceva), rituximab (Rituxan), bevacizumab (Avastin), ipilimumab, nivolumab (Opdivo), pembrolizumab (Ketruda), tamoxifen, fulvestrant, anastrozole, exemestane, letrozole, megestrol acetate, bicalutamide, flutamide, leuprolide, goserelin, or a combination of any two or more thereof.

In any embodiment herein, the administering may include local administration of the compound to a site in the subject including the cancer or local administration of the composition to a site in the subject including the cancer. In any embodiment herein, the administering may include oral, rectal, nasal, vaginal, transdermal, intravenous, intramuscular, or inhalation administration. In any embodiment herein, the administering may include injection of the compound into the site in the subject including the cancer or proximal to the site in the subject including the cancer.

In an aspect, a method of slowing or reversing growth of a tumor in a subject is provided, where the method includes administering to the subject an effective amount of a compound of any embodiment disclosed herein or administering an effective amount of a composition of any embodiment disclosed herein, wherein the effective amount is an amount effective to slow or reverse growth of the tumor.

The tumor may be of a cancer such as squamous cell carcinoma, soft tissue sarcoma, oral melanoma, acute lymphoblastic leukemia (ALL), acute myeloid leukemia (AML), adrenocortical carcinoma, AIDS-related cancers, Kaposi sarcoma (soft tissue sarcoma), AIDS-related lymphoma (lymphoma), anal cancer, appendix cancer, gastrointestinal carcinoid tumors, astrocytomas, atypical teratoid/rhabdoid tumor, basal cell carcinoma of the skin, bile duct cancer, bladder cancer, bone cancer (includes Ewing Sarcoma and Osteosarcoma and Malignant Fibrous Histiocytoma), brain tumors, breast cancer, bronchial tumors (lung cancer), Burkitt lymphoma, carcinoid tumor (gastrointestinal), carcinoma of unknown primary, cardiac (heart) tumors, childhood brain cancer, germ cell tumor, primary CNS lymphoma, cervical cancer, cholangiocarcinoma, chordoma, chronic lymphocytic leukemia (CLL), chronic myelogenous leukemia (CML), chronic myeloproliferative neoplasms, colorectal cancer, craniopharyngioma, cutaneous T-cell lymphoma, ductal carcinoma in situ (DCIS), embryonal tumors, medulloblastoma, endometrial cancer (uterine cancer), ependymoma, esophageal cancer, esthesioneuroblastoma (head and neck cancer), extracranial germ cell tumor, eye cancer, retinoblastoma, fallopian tube cancer, fibrous histiocytoma of bone, osteosarcoma, gallbladder cancer, gastric (stomach) cancer, gastrointestinal stromal tumors (GIST) (soft tissue sarcoma), germ cell tumors, childhood central nervous system germ cell tumors (brain cancer), childhood extracranial germ cell tumors, extragonadal germ cell tumors, ovarian germ cell tumors, testicular cancer, gestational trophoblastic disease, hairy cell leukemia, head and neck cancer, heart tumors, hepatocellular (liver) cancer, histiocytosis, Hodgkin lymphoma, intraocular melanoma, islet cell tumors, pancreatic neuroendocrine tumors, kidney (renal cell) cancer, Langerhans cell histiocytosis, laryngeal cancer (head and neck cancer), leukemia, lip and oral cavity cancer (head and neck cancer), liver cancer, lung cancer, lymphoma, male breast cancer, malignant fibrous histiocytoma of bone and osteosarcoma, melanoma, Merkel cell carcinoma (skin cancer), mesothelioma, metastatic cancer, metastatic squamous neck cancer with occult primary (head and neck cancer), midline tract carcinoma with nut gene changes, mouth cancer (head and neck cancer), multiple endocrine neoplasia syndromes, multiple myeloma/plasma cell neoplasms, mycosis fungoides (lymphoma), myelodysplastic syndromes, myelogenous leukemia, myeloid leukemia, myeloproliferative neoplasms, nasal cavity and paranasal sinus cancer (head and neck cancer), nasopharyngeal cancer (head and neck cancer), neuroblastoma, non-Hodgkin lymphoma, non-small cell lung cancer, oral cancer, osteosarcoma and malignant fibrous histiocytoma of bone, ovarian cancer, pancreatic cancer, pancreatic neuroendocrine tumors (islet cell tumors), papillomatosis (childhood laryngeal), paraganglioma, paranasal sinus and nasal cavity cancer (head and neck cancer), parathyroid cancer, penile cancer, pharyngeal cancer (head and neck cancer), pheochromocytoma, pituitary tumor, plasma cell neoplasm/multiple myeloma, pleuropulmonary blastoma (lung cancer), pregnancy and breast cancer, primary central nervous system (CNS) lymphoma, primary peritoneal cancer, prostate cancer, rectal cancer, recurrent cancer, renal cell (kidney) cancer, rhabdomyosarcoma, salivary gland cancer (head and neck cancer), sarcoma, childhood rhabdomyosarcoma, childhood vascular tumors, Ewing sarcoma (bone cancer), Kaposi sarcoma, osteosarcoma (bone cancer), Sézary syndrome (lymphoma), skin cancer, small cell lung cancer, small intestine cancer, squamous cell carcinoma of the skin, squamous neck cancer with occult primary, metastatic (head and neck cancer), stomach (gastric) cancer, T-cell lymphoma, throat cancer (head and neck cancer), oropharyngeal cancer, hypopharyngeal cancer, thymoma and thymic carcinoma, thyroid cancer, tracheobronchial tumors (lung cancer), transitional cell cancer of the renal pelvis and ureter (kidney (renal cell) cancer), urethral cancer, uterine cancer, uterine sarcoma, vaginal cancer, vascular tumors, vulvar cancer, and/or Wilms tumor and other childhood kidney tumors.

In any embodiment herein, the administering may further include administration of a chemotherapeutic agent such as an alkylating agent; a nitrosourea; an antimetabolite; an anthracycline; a topoisomerase II inhibitor; a mitotic inhibitor; an anti-estrogen; a progestin; an aromatase inhibitor; an anti-androgen; an LHRH agonist; a corticosteroid hormone; a DNA alkylating agent; a taxane; a *vinca* alkaloid; a microtubule poison, or a combination of any two or more thereof. In any embodiment herein, the administering may further include administration of a chemotherapeutic agent such as busulfan, cisplatin, carboplatin, oxaliplatin, an octahedral platinum (IV) compound, chlorambucil, cyclophosphamide, ifosfamide, dacarbazine (DTIC), mechlorethamine (nitrogen mustard), melphalan, temozolomide, carmustine (BCNU), lomustine (CCNU), 5-fluorouracil, capecitabine, 6-mercaptopurine, methotrexate, gemcitabine, cytarabine (ara-C), fludarabine, pemetrexed, daunorubicin, doxorubicin (Adriamycin), epirubicin, idarubicin, mitoxantrone, topotecan, irinotecan, etoposide (VP-16), teniposide, paclitaxel, docetaxel, vinblastine, vincristine, vinorelbine, prednisone, dexamethasone, L-asparaginase, dactinomycin, thalidomide, tretinoin, imatinib (Gleevec), gefitinib (Iressa), erlotinib (Tarceva), rituximab (Rituxan), bevacizumab (Avastin), ipilimumab, nivolumab (Opdivo), pembrolizumab (Ketruda), tamoxifen, fulvestrant, anastrozole, exemestane, letrozole, megestrol acetate, bicalutamide, flutamide, leuprolide, goserelin, or a combination of any two or more thereof.

In any embodiment herein, the administering may include local administration of the compound to the tumor or local administration of the composition to the tumor. In any embodiment herein, the administering may include oral, rectal, nasal, vaginal, transdermal, intravenous, intramuscular, or inhalation administration. In any embodiment herein, the administering may include injection of the compound into the tumor or proximal to the tumor.

In an aspect, a method of vaccinating a subject is provided, where the method includes administering a vaccine for a disease and administering a vaccine adjuvant, where the vaccine adjuvant includes a compound of any embodiment disclosed herein or a composition of any embodiment disclosed herein. The vaccine adjuvant may be administered concurrently with the vaccine and/or sequentially with the vaccine.

The examples herein are provided to illustrate advantages of the present technology and to further assist a person of ordinary skill in the art with preparing or using the compounds and compositions of the present technology. The examples herein are also presented in order to more fully illustrate the preferred aspects of the present technology. The examples should in no way be construed as limiting the scope of the present technology, as defined by the appended claims. The examples can include or incorporate any of the variations, aspects, or embodiments of the present technology described above. The variations, aspects or aspects described above may also further each include or incorporate the variations of any or all other variations, aspects, or embodiments of the present technology.

EXAMPLES

Example 1: Synthetic Procedures

General Experimental Conditions: All solvents were ACS grade or better and used as received. All starting chemicals were purchased from AK Scientific, Ark Pharm, AstraTech, Combi-Blocks, eNovation Chemicals, Fisher, Oakwood Chemical, Sigma-Aldrich, and Strem Chemicals or were synthesized using the cited literature protocol. All reactions were conducted under an atmosphere of $N_2$ or Ar unless stated otherwise. Thin layer chromatography (TLC) was performed on 0.25 mm glass-backed silica GF plates from Analtech. Developed plates were visualized with a handheld UV lamp. Flash chromatography was performed on a CombiFlash RF system using pre-packed columns from Teledyne-Isco. $^1$H and $^{13}$C NMR spectra were recorded on a 500 MHz Bruker AVIII spectrometer equipped with a cryoprobe or a Bruker 400 MHz spectrometer in the noted solvent. Peaks are reported as chemical shift (δ) in ppm, coupling constants reported in (J) are reported in Hz, and number of protons (H) are noted from integrations in MestReNova software. High resolution mass spectra (FIRMS) were obtained on an LCT Premier (Micromass Ltd., Manchester UK) time-of-flight (TOF) mass spectrometer (MS) equipped with an ESI interface. Final compounds were tested for purity and confirmed to be greater than 90% before evaluation in cell assays by HPLC/MS. Compounds 16a, 17a and 18a were synthesized according to literature.[19]

Exemplary Preparation C7-substituted Imidazoquinolones of the Present Technology

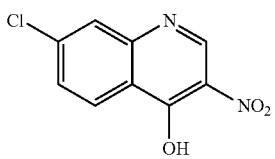

7-Chloro-4-hydroxy-3-nitroquinoline (16b)

The procedure was adapted from Gerster et al. with modifications.[19] In a round bottom flask, 7-chloro-4-hydroxyquinoline was suspended in propionic acid and heated to reflux with a water cooled condenser open to air. 70% nitric acid (2.2 equiv.) was added dropwise over 15 minutes. The reaction was refluxed for 1 h. The reaction was allowed to cool to room temperature and diluted with EtOH and the solid was collected by vacuum filtration. The solid was washed with cold EtOH followed by hexanes, and 16b was isolated in 70% yield as a tan solid and carried to the next step without further purification. $^1$H NMR (400 MHz, DMSO-$d_6$) δ 13.01 (s, 1H), 8.24 (d, J=8.7 Hz, 1H), 7.76 (d, J=2.0 Hz, 1H), 7.55 (dd, J=8.7, 2.0 Hz, 1H).

General Procedure A

The procedure was adapted from Gerster et al. with modifications.[19] Phosphorus oxychloride (1.2 equiv.) was added dropwise to a well stirred suspension of the 7-substituted-4-hydroxy-3-nitroquinoline in anhydrous DMF (1.8 mL per mmol) and an exothermic reaction was observed. After addition of POCl$_3$ was completed, the reaction was heated at 50° C. and stirred for 30 min. The resulting solution was cooled to room temperature and poured into ice water (7.5 mL per mmol). The resulting solid was collected by vacuum filtration, washed with water and pressed dry. The moist solid was added to a round bottom flask and suspended in EtOH (5 mL per mmol), Et$_3$N (2 equiv.), and the appropriate alkyl amine (1.3 equiv.) and refluxed for 15 min. Water was added to the solution and the solid was collected by vacuum filtration and carried onto the next step without further purification.

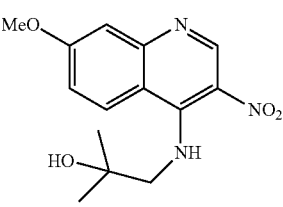

4-(2-Hydroxy-2-methylproylamino)-7-methoxy-3-nitroquinoline (17b)

The title compound was prepared according to the general procedure A using 16a and 1-amino-2-methyl-2-propanol to obtain a bright yellow solid in 80% yield. $^1$H NMR (400 MHz, Methanol-$d_4$) δ 9.20 (s, 1H), 8.38 (d, J=9.5 Hz, 1H), 7.28 (d, J=2.7 Hz, 1H), 7.19 (dd, J=9.4, 2.7 Hz, 1H), 4.59 (s, 1H), 3.97 (s, 3H), 3.91 (s, 2H), 1.29 (s, 6H).

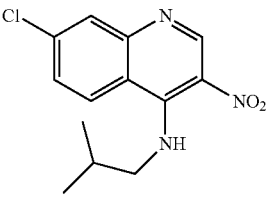

7-Chloro-4-(2-methylpropylamino)-3-nitroquinoline (17c)

The title compound was prepared according to the general procedure A using 16b and isobutylamine to obtain a bright yellow solid in 79% yield. $^1$H NMR (CDCl$_3$, 400 MHz) δ 9.87 (s, 1H), 9.37 (s, 1H), 8.25 (d, J=9.0 Hz, 1H), 8.03 (d, J=2.2 Hz, 1H), 7.45 (dd, J=9.1, 2.2 Hz, 1H), 3.77 (dd, J=6.5, 4.8 Hz, 2H), 2.09 (dt, J=13.3, 6.6 Hz, 1H), 1.11 (d, J=6.7 Hz, 6H).

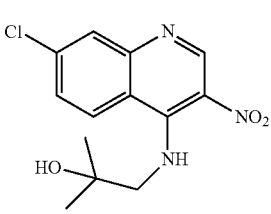

7-Chloro-4-(2-hydroxy-2-methylpropylamino)-3-nitroquinoline (17d)

The title compound was prepared according to the general procedure A using 16b and 1-Amino-2-methyl-2-propanol to obtain a bright yellow solid in 77% yield. $^1$H NMR (CDCl$_3$, 400 MHz) δ 9.93 (s, 1H), 9.37 (s, 1H), 8.18 (d, J=9.0 Hz, 1H), 7.99 (d, J=2.4 Hz, 1H), 7.44 (dd, J=9.1, 2.3 Hz, 1H), 3.85 (d, J=4.9 Hz, 2H), 1.36 (s, 6H).

General Procedure B

A suspension of 7-substituted amino nitroquinoline in EtOH was heated to reflux in open air. Iron (dust 5 equiv.) was added followed by aqueous NH$_4$Cl (2.3 M, 5 equiv.) and refluxed for 2 hours. The solution was allowed to cool and was filtered through a Celite plug and eluted with EtOAc. The volume of solvent was reduced on a rotovap and basified with saturated Na$_2$CO$_3$. The aqueous layer was extracted with EtOAc (3×). The combined organic layers were dried with Na$_2$SO$_4$, filtered, and evaporated on a rotovap to dryness. Valeric or ethoxy acetic acid (10 equiv.) was added to diaminoquinolines in a small round bottom flask. The suspension was heated to reflux (~150° C.) in open air until water ceased to be released from the reaction. The reaction was allowed to cool and diluted with water then basified with 6M NaOH. The water was extracted with DCM (3×) and the combined organic layer was washed with brine and dried with Na$_2$SO$_4$, filtered, and concentrated on rotovap. The compound was purified by CombiFlash (0-10% MeOH in DCM).

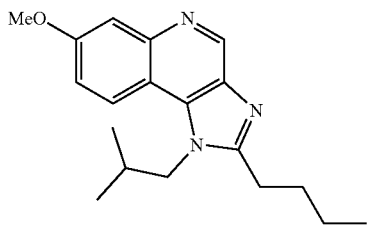

2-Butyl-7-methoxy-1-(2-methylpropyl)-1H-imidazo[4,5-c]quinoline (18a)

The title compound was prepared according to the general procedure B using 17a to obtain a brown solid in 95% yield. ¹H NMR (400 MHz, CDCl₃) δ 9.21 (s, 1H), 7.98 (d, J=9.2 Hz, 1H), 7.65 (d, J=2.7 Hz, 1H), 7.29-7.26 (m, 1H), 4.27 (d, J=7.6 Hz, 2H), 3.96 (s, 3H), 3.03-2.88 (m, 2H), 2.40-2.27 (m, 1H), 1.94 (m, 2H), 1.50 (m, 2H), 1.01 (m, 9H).

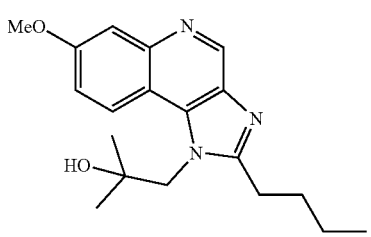

2-Butyl-1-(2-hydroxy-2-methylpropyl)-7-methoxy-1H-imidazo[4,5-c]quinoline (18b)

The title compound was prepared according to the general procedure B using 17b to obtain a brown solid in 48% yield. ¹H NMR (400 MHz, CDCl₃) δ 8.94 (s, 1H), 8.53 (s, 1H), 7.81 (s, 1H), 7.33 (d, J=9.4 Hz, 1H), 4.62 (s, 2H), 3.97 (s, 1H), 3.88 (s, 3H), 3.06 (t, 2H), 1.95 (p, J 7.8 Hz, 2H), 1.52 (q, J 7.5 Hz, 2H), 1.47 (s, 6H), 1.01 (t, J 7.3 Hz, 2H).

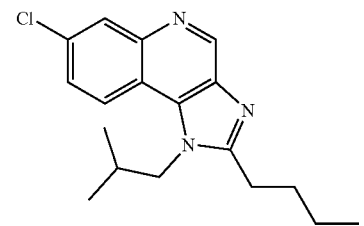

2-Butyl-7-chloro-1-(2-methylpropyl)-1H-imidazo[4,5-c]quinoline (18c)

The title compound was prepared according to the general procedure B using 17c to obtain a brown solid in 80% yield. ¹H NMR (CDCl₃, 500 MHz) δ 9.27 (s, 1H), 8.38 (d, J=2.2 Hz, 1H), 8.05 (d, J=9.0 Hz, 1H), 7.62 (dd, J=9.0, 2.2 Hz, 1H), 4.32 (d, J=7.5 Hz, 2H), 2.99-2.93 (m, 2H), 2.33 (m, 1H), 1.96 (m, 2H), 1.52 (m, 2H), 1.03 (d, J=6.7 Hz, 6H), 1.02 (t, J=7.4 Hz, 3H).

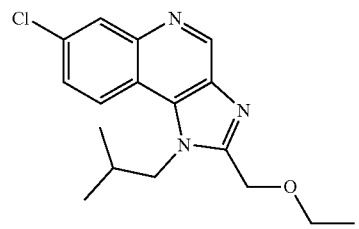

7-Chloro-2-(ethoxymethyl)-1-(2-methylpropyl)-1H-imidazo[4,5-c]quinoline (18d)

The title compound was prepared according to the general procedure B using 17c to obtain a brown solid in 88% yield. ¹H NMR (400 MHz, CDCl₃) δ 9.30 (s, 1H), 8.35 (d, J=2.z2 Hz, 1H), 8.07 (d, J=9.0 Hz, 1H), 7.64 (dd, J=8.9, 2.2 Hz, 1H), 4.89 (s, 2H), 4.51 (d, J=7.7 Hz, 2H), 3.61 (q, J 7.0 Hz, 2H), 2.37 (m, 1H), 1.25 (t, J 7.0 Hz, 3H), 1.09-1.00 (d, J=6.7 Hz, 6H).

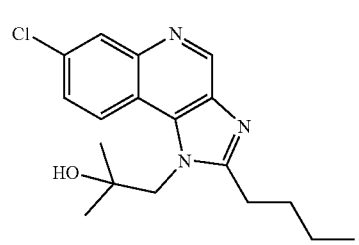

2-Butyl-7-chloro-1-(2-hydroxy-2-methylpropyl)-1H-imidazo[4,5-c]quinoline (18e)

The title compound was prepared according to the general procedure B using 17d to obtain a brown solid in 87% yield. ¹H NMR (400 MHz, CDCl₃) δ 8.99 (s, 1H), 8.52 (d, J=9.0 Hz, 1H), 8.13 (s, 1H), 7.55 (dd, J 9.1, 2.2 Hz, 1H), 4.62 (s, 2H), 3.06 (s, 2H), 1.95 (p, J=7.7 Hz, 2H), 1.51 (m 2H), 1.46 (s, 6H), 1.01 (t, J 7.3 Hz, 3H).

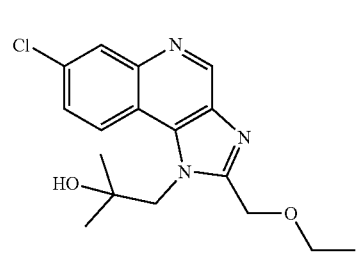

7-Chloro-2-(ethoxymethyl)-1-(2-hydroxy-2-methylpropyl)-1H-imidazo[4,5-c]quinoline (18f)

The title compound was prepared according to the general procedure B using 17d to obtain a brown solid in 87% yield. ¹H NMR (400 MHz, CDCl₃) δ 9.14 (s, 1H), 8.41 (s, 1H), 8.25 (s, 1H), 7.60 (d, J=8.9 Hz, 1H), 4.99 (s, 2H), 4.83 (s, 2H), 3.65 (q, J=7.0 Hz, 2H), 1.40 (s, 6H), 1.25 (dd, J=7.4, 6.7 Hz, 3H).

General Procedure C

The procedure was adapted from Gerster et al. with modifications.[19] In a round bottom flask, imidazoquinoline was dissolved in CHCl₃ and stirred at room temperature. mCPBA (1+1 equiv.) was added portion-wise 1 h apart. After 3 hours the reaction was diluted with dichloromethane (DCM), washed with saturated Na₂CO₃ aqueous solution, extracted with DCM (3×), dried with Na₂SO₄, filtered, and concentrated on rotovap. The compound was purified by CombiFlash (0-10% MeOH in DCM).

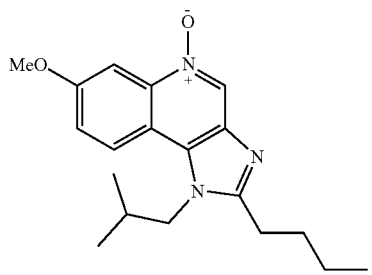

19a

2-Butyl-7-methoxy-1-(2-methylpropyl)-1H-imidazo[4,5-c]quinoline 5-oxide (19a)

The title compound was prepared according to the general procedure C using 18a to obtain a brown solid in 45% yield. $^1$H NMR (DMSO-$d_6$, 500 MHz) δ 8.99 (s, 1H), 8.24 (d, J=9.0 Hz, 1H), 8.22 (d, J=2.8 Hz, 1H), 7.47 (dd, J=9.2, 2.9 Hz, 1H), 4.37 (d, J=7.6 Hz, 2H), 2.91 (t, J=7.6 Hz, 2H), 2.13 (dt, J=13.5, 6.8 Hz, 1H), 1.82 (p, J=7.5 Hz, 2H), 1.44 (h, J=7.4 Hz, 2H), 0.94 (t, J=7.5 Hz, 3H), 0.91 (d, J=6.7 Hz, 6H). HRMS (m/z): [M+H]⁺ calcd for $C_{19}H_{26}N_3O_2$, 328.2025; found 328.2034.

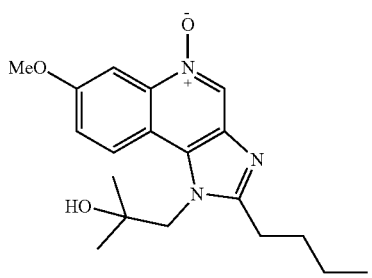

19b

2-Butyl-1-(2-hydroxy-2-methylpropyl)-7-methoxy-1H-imidazo[4,5-c]quinoline 5-oxide (19b)

The title compound was prepared according to the general procedure C using 18b to obtain a brown solid in 90% yield. $^1$H NMR (400 MHz, CDCl₃) δ 8.67 (d, J=9.3 Hz, 1H), 8.02 (s, 1H), 7.52 (d, J=2.7 Hz, 1H), 7.19 (dd, J=9.3, 2.8 Hz, 1H), 4.10 (s, 1H), 3.83 (s, 3H), 3.43 (d, J=3.8 Hz, 1H), 2.92 (s, 3H), 1.86 (q, J=7.7 Hz, 2H), 1.30 (d, J=2.0 Hz, 2H), 0.98 (t, J=7.4 Hz, 3H). HRMS (m/z): [M+H]⁺ calcd for $C_{19}H_{26}N_3O_3$, 344.1974; found 344.1986.

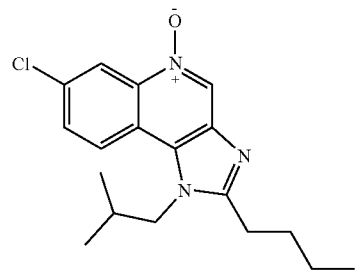

19c

2-Butyl-7-chloro-1-(2-methylpropyl)-1H-imidazo[4,5-c]quinoline 5-oxide (19c)

The title compound was prepared according to the general procedure C using 18c to obtain a brown solid in 80% yield. $^1$H NMR (CDCl₃, 500 MHz) δ 9.58 (s, 1H), 8.88 (d, J=2.0 Hz, 1H), 8.20 (d, J=9.0 Hz, 1H), 7.86 (dd, J=9.0, 2.2 Hz, 1H), 4.39 (d, J=7.6 Hz, 2H), 3.04-2.97 (m, 2H), 2.30 (dt, J=13.8, 6.9 Hz, 1H), 1.97 (p, J=7.6 Hz, 2H), 1.52 (ddd, J=14.2, 7.2, 5.4 Hz, 3H), 1.07 (d, J=6.7 Hz, 6H), 1.03 (t, J=7.3 Hz, 3H); HRMS (m/z): [M+Na]⁺ calcd for $C_{18}H_{22}ClN_3ONa$, 354.1349; found 354.1362.

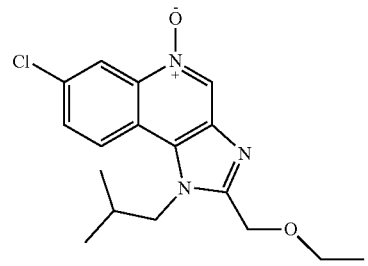

19d

7-Chloro-2-(ethoxymethyl)-1-(2-methylpropyl)-1H-imidazo[4,5-c]quinoline 5-oxide (19d)

The title compound was prepared according to the general procedure C using 18d to obtain a brown solid in 76% yield. $^1$H NMR (400 MHz, DMSO-$d_6$) δ 9.12 (d, J=9.9 Hz, 1H), 8.83-8.73 (m, 1H), 8.40 (dd, J=20.5, 9.0 Hz, 1H), 7.92 (ddd, J=10.9, 8.9, 2.4 Hz, 1H), 4.80 (s, 2H), 4.55-4.43 (m, 2H), 3.59 (q, J=7.0 Hz, 2H), 2.22 (p, J=7.1 Hz, 1H), 1.16 (t, J=7.0 Hz, 3H), 0.92 (d, J=6.7 Hz, 6H). HRMS (m/z): [M+H]⁺ calcd for $C_{17}H_{21}ClN_3O_2$, 334.1322; found 334.1328.

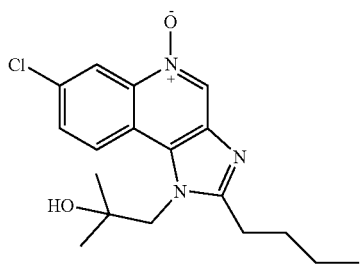

19e

2-Butyl-7-chloro-1-(2-hydroxy-2-methylpropyl)-1H-imidazo[4,5-c]quinoline 5-oxide (19e)

The title compound was prepared according to the general procedure C using 18e to obtain a brown solid in 71% yield. $^1$H NMR (400 MHz, CDCl$_3$) δ 9.04 (s, 1H), 8.72 (d, J=9.1 Hz, 1H), 8.48 (s, 1H), 7.65 (d, J=8.5 Hz, 1H), 4.48 (s, 2H), 3.01 (s, 2H), 1.93 (p, J=7.7 Hz, 2H), 1.51 (dt, J=15.0, 7.4 Hz, 2H), 1.44 (s, 6H), 1.23 (d, J=16.9 Hz, 1H), 1.01 (t, J=7.3 Hz, 3H). HRMS (m/z): [M+H]$^+$ calcd for C$_{18}$H$_{23}$ClN$_3$O$_2$, 348.1479; found 348.1468.

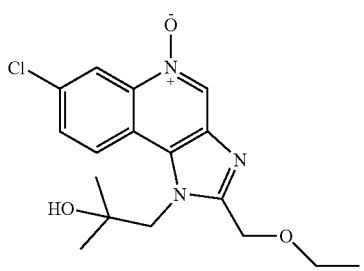

19f

7-Chloro-2-(ethoxymethyl)-1-(2-hydroxy-2-methylpropyl)-1H-imidazo[4,5-c]quinoline 5-oxide (19f)

The title compound was prepared according to the general procedure C using 18f to obtain a brown solid in 99% yield. $^1$H NMR (CDCl$_3$, 500 MHz) δ 9.18 (s, 1H), 8.66 (d, J=8.9 Hz, 1H), 8.64-8.60 (m, 1H), 7.73 (d, J=8.3 Hz, 1H), 4.97 (s, 2H), 4.80 (s, 2H), 3.61 (q, J=7.0 Hz, 2H), 1.41 (s, 6H), 1.24 (t, J=7.0 Hz, 3H). HRMS (m/z): [M+Na]$^+$ calcd for C$_{17}$H$_{20}$ClN$_3$O$_3$Na, 372.1091; found 372.1085.

General Procedure D

The procedure was adapted from Gerster et al. with modifications.[19] Concentrated NH$_4$OH (1 mL per mmol) was added to a round bottom flask containing N-oxide imidazoquinoline (1 equiv.) in anhydrous DCM (1 mL per mmol) stirring vigorously at room temperature. p-TsCl (1.1 equiv.) was added to an addition funnel and dissolved in anhydrous DCM (1 mL per mmol). The p-TsCl in DCM was added dropwise slowly over 15 min minutes and more DCM was added to help push residual p-TsCl into the flask to the round bottom. An exotherm was observed during the addition. The reaction was allowed to stir for another 15 min after addition of p-TsCl was completed. Water was added and if precipitate formed, the solid was isolated by vacuum filtration. The mother liquor or biphasic mixture was extracted with DCM, washed with brine, dried with Na$_2$SO$_4$, and concentrated in vacuo and purified by CombiFlash.

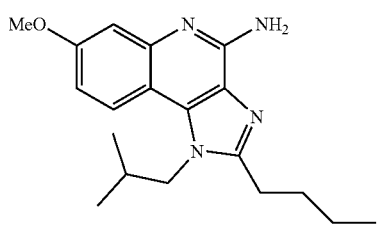

4

4-Amino-2-butyl-7-methoxy-1-(2-methylpropyl)-1H-imidazo[4,5-c]quinoline (4)

The title compound was prepared according to the general procedure D using 19a to obtain a brown solid in 77% yield. $^1$H NMR (CDCl$_3$, 500 MHz) δ 7.76 (d, J=9.0 Hz, 1H), 7.30 (d, J=2.7 Hz, 1H), 7.00 (dd, J=9.0, 2.6 Hz, 1H), 6.43 (s, 2H), 4.20 (d, J=7.6 Hz, 2H), 3.92 (s, 3H), 2.90-2.83 (m, 2H), 2.31 (dp, J=13.4, 6.6 Hz, 1H), 1.86 (p, J=7.6 Hz, 2H), 1.49 (h, J=7.4 Hz, 2H), 1.02-0.97 (m, 9H); $^{13}$C NMR (CDCl$_3$, 126 MHz) δ 159.49, 154.41, 150.80, 134.77, 124.73, 121.28, 114.23, 108.69, 105.40, 55.70, 52.71, 30.01, 29.28, 27.58, 22.73, 19.92, 19.79, 13.99. FIRMS (m/z): [M+H]$^+$ calcd for C$_{19}$H$_{27}$N$_4$O, 327.2185; found 327.2196.

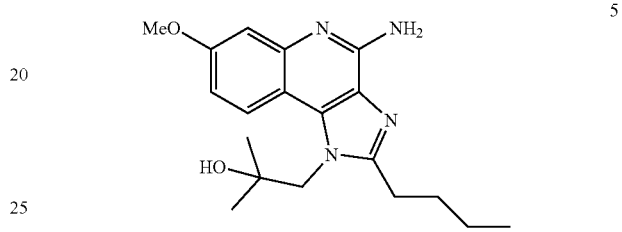

5

4-Amino-2-butyl-1-(2-hydroxy-2-methylpropyl)-7-methoxy-1H-imidazo[4,5-c]quinoline (5)

The title compound was prepared according to the general procedure D using 19b to obtain a brown solid in 71% yield. $^1$H NMR (500 MHz, DMSO-d$_6$) δ 9.12 (d, J=10.7 Hz, 1H), 8.80 (dd, J=5.0, 2.3 Hz, 1H), 8.40 (dd, J=20.5, 9.1 Hz, 1H), 7.91 (ddd, J=11.1, 9.0, 2.4 Hz, 1H), 4.80 (s, 1H), 4.49 (s, J=21.9, 7.7 Hz, 2H), 3.59 (q, J=7.0 Hz, 2H), 2.22 (p, J=7.0 Hz, 1H), 1.16 (t, J=7.0 Hz, 3H), 0.92 (d, J=6.6 Hz, 6H); $^{13}$C NMR (126 MHz, DMSO-d$_6$) δ 157.65, 154.34, 151.79, 146.23, 134.09, 124.72, 122.33, 110.62, 109.58, 106.88, 70.79, 54.87, 54.46, 48.59, 29.80, 26.76, 22.05, 13.87. HRMS (m/z): [M+H]$^+$ calcd for C$_{19}$H$_{27}$N$_4$O$_2$, 343.2134; found 343.2129.

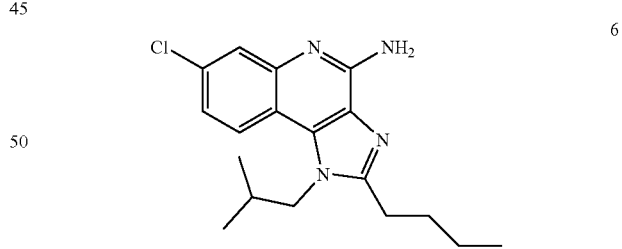

6

4-Amino-2-butyl-7-chloro-1-(2-methylpropyl)-1H-imidazo[4,5-c]quinoline (6)

The title compound was prepared according to the general procedure D using 19c to obtain a brown solid in 81% yield. $^1$H NMR (DMSO-d$_6$, 500 MHz) δ 7.97 (d, J=8.9 Hz, 1H), 7.56 (d, J=2.3 Hz, 1H), 7.26 (dd, J=8.8, 2.3 Hz, 1H), 6.69 (s, 2H), 4.33 (d, J=7.6 Hz, 2H), 2.93-2.87 (m, 2H), 2.11 (dq, J=13.8, 6.9 Hz, 1H), 1.85-1.76 (m, 2H), 1.44 (dt, J=14.7, 7.4 Hz, 2H), 0.95 (t, J=7.4 Hz, 3H), 0.91 (d, J=6.6 Hz, 6H); $^{13}$C NMR (DMSO-d$_6$, 126 MHz) δ 153.99, 152.59, 145.83, 132.08, 130.51, 126.58, 124.81, 121.97, 120.90, 113.57, 51.31, 29.65, 28.82, 26.43, 21.93, 19.16, 13.81. HRMS (m/z): [M]+ calcd for $C_{18}H_{23}ClN_4$, 330.1611; found 330.1630.

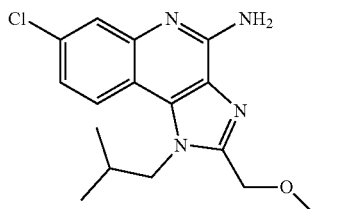

4-Amino-7-chloro-2-(ethoxymethyl)-1-(2-methylpropyl)-1H-imidazo[4,5-c]quinoline (7)

The title compound was prepared according to the general procedure D using 19d to obtain a brown solid in 78% yield. $^1$H NMR (500 MHz, DMSO-$d_6$) δ 8.01 (d, J=8.8 Hz, 1H), 7.58 (d, J=2.3 Hz, 1H), 7.27 (dd, J=8.8, 2.3 Hz, 1H), 6.88 (s, 2H), 4.75 (s, 2H), 4.42 (d, J=7.7 Hz, 2H), 3.56 (q, J=7.0 Hz, 2H), 2.20 (hept, J=6.9 Hz, 1H), 1.15 (t, J=7.0 Hz, 3H), 0.91 (d, J=6.6 Hz, 6H); $^{13}$C NMR (126 MHz, DMSO-$d_6$) δ 152.93, 149.72, 146.29, 132.82, 131.12, 126.48, 124.82, 122.43, 121.00, 113.45, 65.41, 64.16, 51.77, 28.61, 19.25, 14.92. HRMS (m/z): [M+H]+ calcd for $C_{17}H_{22}ClN_4O$, 333.1482; found 333.1475.

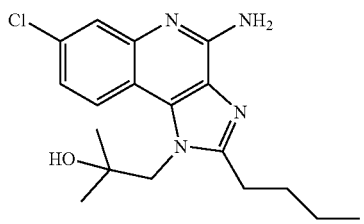

4-Amino-2-butyl-7-chloro-1-(2-hydroxy-2-methylpropyl)-1H-imidazo[4,5-c]quinoline (8)

The title compound was prepared according to the general procedure D using 19e to obtain a brown solid in 73% yield. $^1$H NMR (CDCl$_3$, 500 MHz) δ 8.29 (d, J=8.9 Hz, 1H), 7.53 (d, J=2.3 Hz, 1H), 7.17 (dd, J=8.8, 2.3 Hz, 1H), 6.63 (s, 2H), 4.77 (s, 1H), 4.51 (s, 2H), 3.00 (t, 2H), 1.78 (ddd, J=15.4, 8.9, 7.1 Hz, 2H), 1.42 (h, J=7.4 Hz, 2H), 1.16 (s, 6H), 0.94 (t, J=7.4 Hz, 3H); $^{13}$C NMR (CDCl$_3$, 126z MHz) δ 155.39, 152.57, 145.93, 133.30, 130.16, 126.28, 124.58, 123.17, 120.10, 114.26, 70.76, 54.49, 48.59, 29.78, 26.80, 22.03, 13.86. HRMS (m/z): [M+H]+ calcd for $C_{18}H_{24}ClN_4O$, 347.1639; found 347.1649.

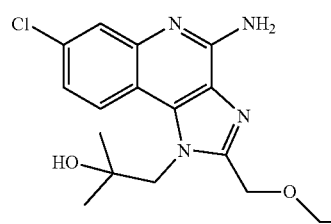

4-Amino-7-chloro-2-(ethoxymethyl)-1-(2-hydroxy-2-methylpropyl)-1H-imidazo[4,5-c]quinoline (9)

The title compound was prepared according to the general procedure D using 19f to obtain a brown solid in 84% yield. $^1$H NMR (DMSO-$d_6$, 500 MHz) δ 8.30 (d, J=8.9 Hz, 1H), 7.54 (d, J=2.3 Hz, 1H), 7.19 (dd, J=8.8, 2.3 Hz, 1H), 6.79 (s, 2H), 4.88 (s, 1H), 4.64 (s, 2H), 3.51 (q, J=7.0 Hz, 2H), 1.16 (s, 6H), 1.13 (t, J=7.0 Hz, 3H); $^{13}$C NMR (DMSO-$d_6$, 126 MHz) δ 153.38, 151.61, 146.91, 134.40, 131.26, 126.67, 125.14, 123.86, 120.75, 114.52, 71.11, 65.80, 65.28, 55.25, 15.47. HRMS (m/z): [M+H]+ calcd for $C_{17}H_{22}ClN_4O_2$, 349.1431; found 349.1425.

Preparation of Aryl Nitriles
General Procedure E

The procedure was adapted from Littke et al. with modifications.[4] Aryl chloride (1 equiv.), Pd(TFA)$_2$ (5%), Zn (dust, 20%), rac-2-(Di-tert-butylphosphino)-1,1'-binaphthyl (TrixiePhos) (10%), Zn(CN)$_2$ (56%) were added to an oven-dried 40 mL vial and vacuum flushed with nitrogen three times. Anhydrous dimethylacetamide (DMAC) (0.19 M) was added via syringe to the sealed vial. The vial was shaken and placed on a heating mantel at 95° C. and stirred overnight. The mixture was allowed to cool to room temperature and filtered through a plug of Celite using either 100% EtOAc or 20% MeOH in DCM to elute product. The solvent was then concentrated down and redissolved in EtOAc and washed with water (4-5× by 10× the volume of DMAC), washed with brine and dried with Na$_2$SO$_4$. Solvent was concentrated down on rotovap and purified by CombiFlash (0-10% MeOH in DCM).

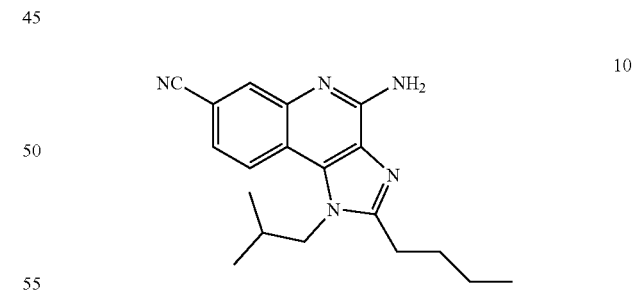

4-Amino-2-butyl-7-carbonitrile-1-(2-methylpropyl)-1H-imidazo[4,5-c]quinoline (10)

The title compound was prepared according to the general procedure E using 6 to obtain a brown solid in 82% yield. $^1$H NMR (500 MHz, DMSO-$d_6$) δ 8.13 (d, J=8.5 Hz, 1H), 7.98 (t, J=1.5 Hz, 1H), 7.56 (dt, J=8.3, 1.5 Hz, 1H), 6.90 (s, 2H), 4.38 (d, J=7.6 Hz, 2H), 2.94 (t, J=6.3 Hz, 2H), 2.18-2.06 (m, 1H), 1.83 (t, J=7.7 Hz, 2H), 1.46 (q, J=7.6 Hz, 2H), 0.98-0.94 (t, 3H), 0.93 (d, J=6.6 Hz, 7H); $^{13}$C NMR (500 MHz, DMSO-$d_6$) δ 155.29, 152.90, 144.07, 131.51, 130.47, 128.12, 122.36, 121.70, 119.40, 118.00, 108.27, 51.38, 29.60, 28.90, 26.48, 21.91, 19.13, 13.80. HRMS (m/z): [M+H]$^+$ calcd for $C_{19}H_{24}N_5$, 322.2032; found 322.2034.

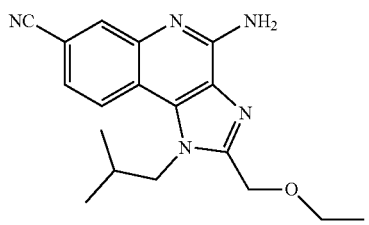

4-Amino-7-carbonitrile-2-(ethoxymethyl)-1-(2-methylpropyl)-1H-imidazo[4,5-c]quinoline (11)

The title compound was prepared according to the general procedure E using 7 to obtain a brown solid in 80% yield. $^1$H NMR (400 MHz, CDCl$_3$) δ 8.22 (d, J=1.7 Hz, 1H), 8.01 (d, J=8.5 Hz, 1H), 7.61 (dd, J=8.5, 1.7 Hz, 1H), 6.42 (s, 2H), 4.86 (s, 2H), 4.48 (d, J=7.7 Hz, 2H), 4.15 (q, J=7.1 Hz, 1H), 3.65 (q, J=7.0 Hz, 2H), 2.36 (dt, J=13.9, 7.0 Hz, 1H), 1.31-1.24 (m, 3H), 1.07 (d, J=6.7 Hz, 6H); $^{13}$C NMR (126 MHz, DMSO-$d_6$) δ 151.85, 149.18, 143.94, 132.94, 132.40, 129.13, 124.57, 122.81, 119.48, 119.06, 109.77, 66.15, 64.69, 52.50, 29.12, 19.74, 15.45. HRMS (m/z): [M+H]$^+$ calcd for $C_{18}H_{22}N_5O$, 324.1824; found 324.1816.

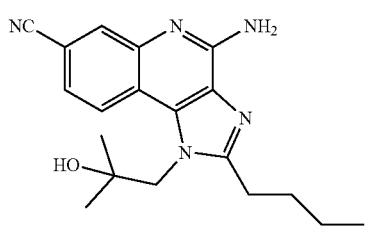

4-Amino-2-butyl-7-carbonitrile-1-(2-hydroxy-2-methylpropyl)-1H-imidazo[4,5-c]quinoline (12)

The title compound was prepared according to the general procedure E using 8 to obtain a brown solid in 81% yield. $^1$H NMR (500 MHz, DMSO-$d_6$) δ 8.45 (d, J=8.6 Hz, 1H), 7.94 (d, J=1.8 Hz, 1H), 7.46 (dd, J=8.6, 1.8 Hz, 1H), 6.85 (s, 2H), 4.78 (s, 1H), 4.52 (s, 2H), 3.02 (t, J=7.8 Hz, 2H), 1.80 (ddd, J=15.3, 8.9, 7.1 Hz, 2H), 1.42 (h, J=7.4 Hz, 2H), 1.17 (s, 6H), 0.94 (t, J=7.4 Hz, 3H); $^{13}$C NMR (126 MHz, DMSO-$d_6$) δ 156.64, 152.92, 144.16, 132.82, 130.29, 127.82, 123.04, 121.50, 119.52, 118.79, 107.94, 70.75, 54.55, 29.75, 26.88, 22.02, 13.86. HRMS (m/z): [M+H]$^+$ calcd for $C_{19}H_{24}N_5O$, 338.1981; found 338.1981.

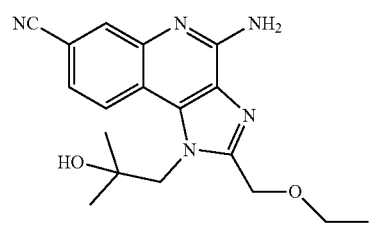

4-Amino-7-carbonitrile-2-(ethoxymethyl)-1-(2-hydroxy-2-methylpropyl)-1H-imidazo[4,5-c]quinoline (13)

The title compound was prepared according to the general procedure E using 9 to obtain a brown solid in 76% yield. $^1$H NMR (500 MHz, DMSO-$d_6$) δ 8.47 (d, J=8.6 Hz, 1H), 7.96 (d, J=1.8 Hz, 1H), 7.48 (dd, J=8.5, 1.8 Hz, 1H), 7.01 (s, 2H), 4.89 (s, 1H), 4.68 (s, 2H), 3.52 (q, J=7.0 Hz, 2H), 1.19-1.15 (m, 2H), 1.13 (t, J=7.0 Hz, 3H); $^{13}$C NMR (126 MHz, DMSO-$d_6$) δ 153.22, 152.28, 144.67, 133.41, 130.35, 127.66, 123.24, 121.66, 119.38, 118.59, 108.61, 70.61, 65.43, 64.75, 54.86, 27.58, 14.98. HRMS (m/z): [M+H]$^+$ calcd for $C_{18}H_{22}N_5O_2$, 340.1774; found 340.1778.

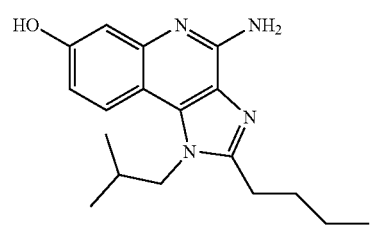

4-Amino-2-butyl-7-hydroxy-1-(2-methylpropyl)-1H-imidazo[4,5-c]quinoline (14)

4 (1 equiv.) was added to a melt of pyridine hydrochloride (10 equiv.) and heated at 210° C. for 30 minutes. The reaction was allowed to cool for a few minutes and diluted with water then acidified with 6 N HCl to pH 1. The solid was collected by vacuum filtration and washed with hexanes and dried in air to obtain 14 in 85% yield as a light brown solid. $^1$H NMR (500 MHz, DMSO-$d_6$) δ 14.00 (s, 1H), 10.69 (s, 1H), 8.60 (s, 3H), 7.98 (d, J=9.1 Hz, 1H), 7.19 (d, J=2.4 Hz, 1H), 7.09 (dd, J=9.0, 2.4 Hz, 1H), 5.10 (s, 4H), 4.35 (d, J=7.6 Hz, 2H), 2.92 (t, J=7.6 Hz, 2H), 2.09 (dq, J=13.8, 6.9 Hz, 1H), 1.81 (p, J=7.6 Hz, 2H), 1.44 (h, J=7.4 Hz, 2H), 0.97-0.90 (m, 9H); $^{13}$C NMR (126 MHz, DMSO-$d_6$) δ 158.73, 155.98, 148.63, 135.85, 135.55, 123.38, 122.04, 115.11, 105.18, 102.76, 51.49, 29.25, 28.73, 26.38, 21.84, 19.11, 13.81. HRMS (m/z): [M+H]$^+$ calcd for $C_{18}H_{25}N_4O$ 313.2028; found 313.2041.

Scheme 1: Synthesis of R848-Toco conjugate (17)

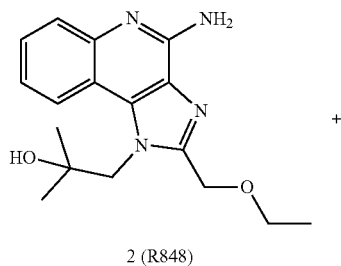

2 (R848)

+

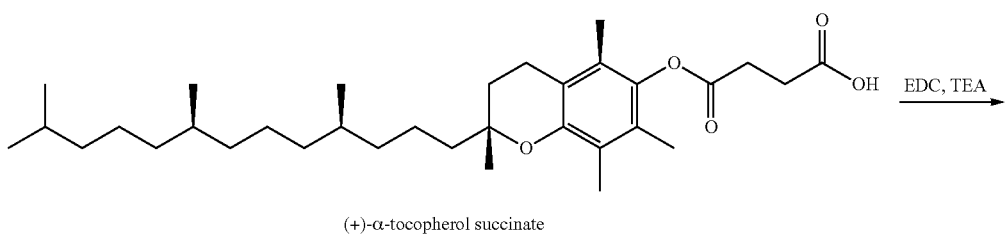

(+)-α-tocopherol succinate

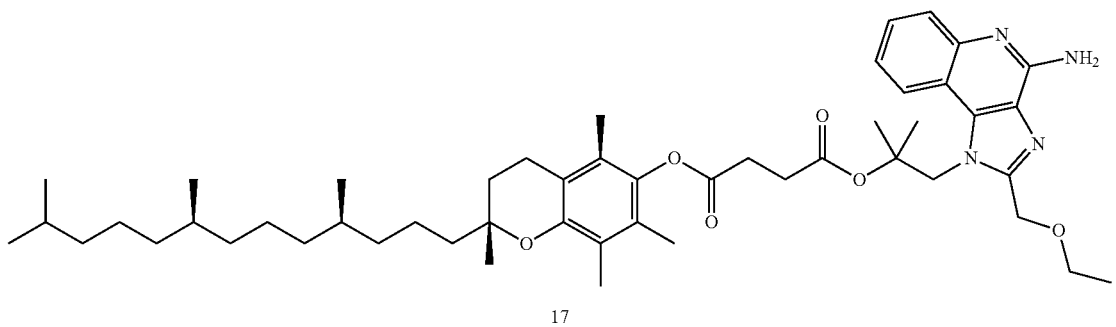

17

R848-Toco Conjugate (17)

R848, 2, purchased from Invivogen (San Diego, CA, USA), (100 mg, 0.32 mmol) was conjugated to (+)-α-tocopherol succinate (253 mg, 0.47 mmol) in the presence of EDC·HCl (75 mg, 0.48 mmol) and TEA (0.2 mL) in $CH_2Cl_2$ (10 mL) under a nitrogen atmosphere and at ambient temperature (ca. 20° C.) for 15 h. The mixture was then purified by silica gel chromatography using hexane-ethyl acetate as eluent solvents (product eluted at 70% ethyl acetate) and dried in vacuo to provide a clear pale-yellow viscous oil product 17 (177 mg, 67%). Purity was 99.4% by high-performance liquid chromatography (HPLC) analysis (LC-2010C HT, Shimadzu, Kyoto, Japan) with a UV detector (290 nm) and a C8 column (4.6 um×50 mm, 5 μm), thermostatic at 45° C. Mobile phases were A: 0.1% TFA/water and B: 0.1% TFA/acetonitrile with a gradient elution (20-95% B) over 8 min at a flow rate of 1.0 mL/min. $^1$H NMR (400 MHz, Chloroform-d) δ 8.20 (d, J=8.3 Hz, 1H), 8.00 (dd, J=8.4, 1.4 Hz, 1H), 7.54 (dddd, J=39.6, 8.3, 7.0, 1.3 Hz, 2H), 4.89 (s, 2H), 4.77 (s, 2H), 3.62 (q, J=7.0 Hz, 4H), 3.11 (t, J=6.9 Hz, 2H), 2.58 (t, J=6.8 Hz, 2H), 2.07 (d, J=7.8 Hz, 6H), 2.02 (s, 3H), 1.77 (ddq, J=20.0, 13.2, 6.8 Hz, 2H), 0.94-0.73 (m, 13H). Chemical formula: $C_{50}H_{74}N_4O_6$. ESI-MS: M+H$^+$=827.5608, found 827.5660.

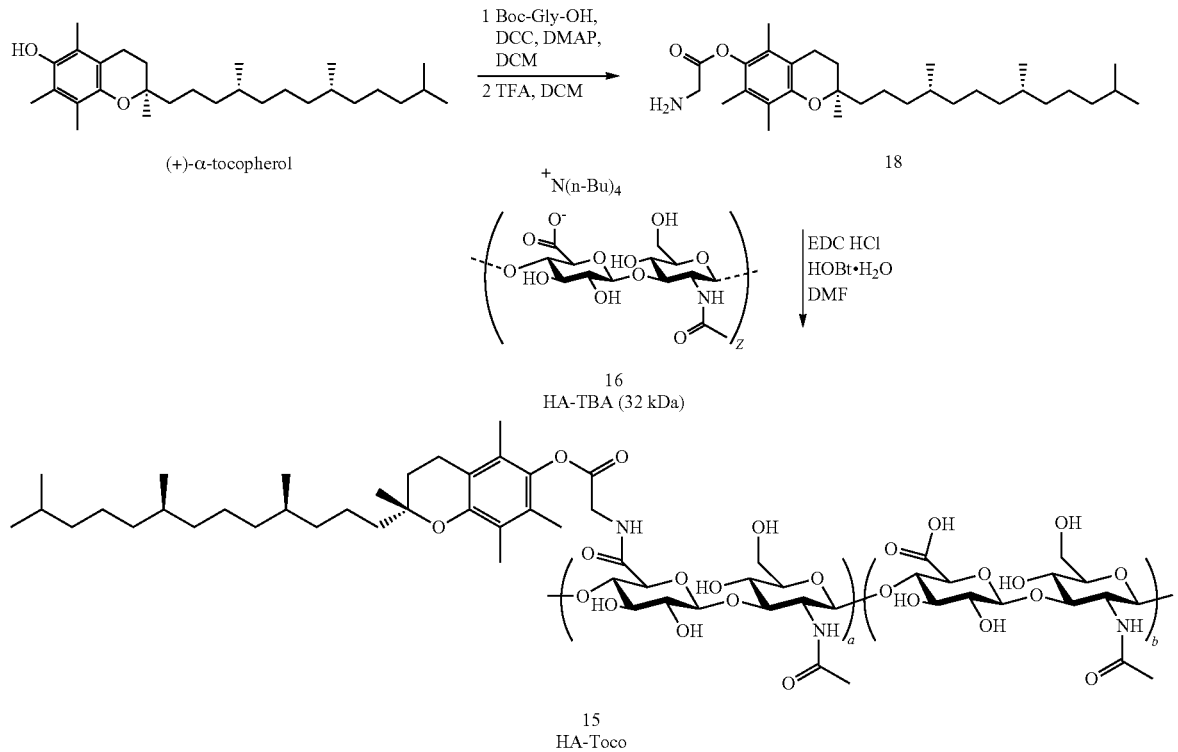

Scheme 2: Synthesis of HA-Toco (15)

Glycine-Tocopherol (18)

A mixture of Boc-Gly-OH (0.89 g, 5.11 mmol), (+)-α-tocopherol (2.20 g, 5.11 mmol), DCC (1.05 g, 5.11 mmol), and DMAP (64 mg, 0.52 mmol) in $CH_2Cl_2$ (20 mL) was stirred at ca. 20° C. overnight. The reaction mixture was then cooled down to −20° C. and filtered to remove unwanted precipitate. Filtrate was then purified by silica gel chromatography using hexane-ethyl acetate as eluent solvents (product eluted at 5% ethyl acetate) and dried in vacuo to provide colorless oil (2.89 g, 96%). The oil was dissolved in $CH_2Cl_2$ (15 mL), and a TFA solution in $CH_2Cl_2$ (50% v/v, 5 mL) was added dropwise. The mixture was stirred at 0° C. for 0.5 h and then warmed to room temperature (ca. 20° C.) and stirred for an additional 1 h, followed by evaporation in vacuo to remove the solvent and TFA. The gray solid was purified via silica gel chromatography using hexane-ethyl acetate as eluent solvents (product eluted at 5% ethyl acetate) and dried in vacuo to provide a white solid as the product 18 (14.24 g, 60%). $^1$H NMR (400 MHz, DMSO-$d_6$) δ 8.44 (s, 2H), 4.26 (s, 2H), 2.57 (t, J=6.9 Hz, 2H), 2.02 (s, 3H), 1.96 (s, 3H), 1.94 (s, 3H), 1.81-1.72 (m, 2H), 1.56-1.44 (m, 3H), 1.40 (t, J=8.7 Hz, 4H), 1.31-1.16 (m, 11H), 1.16-0.99 (m, 6H), 0.83 (dd, J=9.1, 6.5 Hz, 12H). Chemical formula: $C_{31}H_{53}NO_3$. ESI-MS: M+H$^+$=487.4025, found 487.4106.

Hyaluronan-Tetrabutylammonium Salt (HA-TBA, 16)

Hyaluronic acid sodium salt (32 kDa, 10 g) was dissolved in deionized $H_2O$ (200 mL) and stirred for 1 h, followed by the addition of Dowex AG 50W-X8 resin (30 g), and the mixture was stirred for 12 h at ca. 20° C. The resin was removed via filtration, and the filtrate was titrated with TBA-OH to adjust pH to 8-9. The water solution was lyophilized to obtain a pale-yellow powdered cake 16 (6.7 g, 64%).

HA-Tocopherol (15)

A solution of 16 (200 mg, 0.32 mmol) in DMF (15 mL) was stirred for 1 h at ca. 20° C. DMF solutions of 18 (19 mg, 0.03 mmol, 10 mg/mL), EDC·HCl (153 mg, 0.80 mmol, 10 mg/mL), and HOBt·$H_2O$ (74 mg, 0.48 mmol, 20 mg/mL) were added subsequently to the reaction mixture, which was stirred at ca. 20° C. for 12 h. The reaction mixture was dialyzed using dialysis tubing (MWCO 10,000 kDa) against 50% EtOH/$H_2O$ for 12 h, sodium chloride solution (150 mM) for 12 h, followed by three water changes over another 48 h. The dialyzed mixture was lyophilized to yield a white cotton-like polymer 15 (139 mg, 69%). The degree of substitution (SD) of tocopherol molecules on HA was calculated as around 7% on molar basis by comparing the intensity ratio between the representative peaks of N-acetyl peak of HA (1.8 ppm) and methyl groups of tocopherol (0.8 ppm) in $^1$H NMR spectrum.

Preparation of Agonist/HA-Toco Nanocomplex

The agonist-loaded nanocomplex was prepared by an emulsification-solvent evaporation method.[29,64] An aqueous solution of 15 (10 mg/mL) was added dropwise to an ethanol solution of 2 or 17 (10 mg/mL) while stirring, and the mixture was stirred at 200 rpm for 10 min. The emulsion was then dried using a Centrivap concentrator (Labconco, Kansas City, MO, USA) to obtain a pale-yellow transparent solid, which was rehydrated with sterile water for injection over 12 h to form a white emulsion. Particle size measurements were performed using a ZetaPALS (Brookhaven Instruments Corp., ZetaPALS, Holtsville, New York) at 25° C. Samples were dissolved in 1×PBS to a concentration of 0.05 mg/mL and filtered through a 0.45 μm filter. The intensity-averaged hydrodynamic radius was reported.

To determine the drug concentration in the formulation, a sample was diluted 1:100 v/v in acetone and sonicated for 10 min. The mixture was centrifuged (12,000×g, 5 min) and the supernatant was measured by HPLC (LC-2010C HT, Shimadzu, Kyoto, Japan) with a UV detector (290 nm) and a C8 column (4.6 um×150 mm, 5 μm), thermostated at 45° C. The mobile phases were A: 0.1% TFA/water and B: 0.1% TFA/ acetonitrile with a gradient elution (20-100% B) over 13 min at a flow rate of 1.0 mL/min.

Characterization of R848-Toco/HA-Toco as a Nano-Emulsion

Nanoformulations and depots are useful strategies for localized targeted delivery and sustained release.[65] Compared to a 'conjugation to' method wherein the parent drug is directly conjugated to the polymer, prodrug synthesis followed by polymer encapsulation has more versatility, such as low steric hindrance, easy purification and quantification of the prodrug.[62] In this study, R848 was prepared as a prodrug by conjugation to α-tocopherol (Toco). α-Tocopherol, a constituent of vitamin E, is a hydrophobic compound that itself has been investigated as an anti-cancer drug, as it shows anti-neoplastic activity with no toxicity to normal cells.[31,44] The R848-Toco prodrug had increased lipophilicity compared to the parent drug, and thus could be easily loaded into the hydrophobic inner core of the novel polymer HA-Toco.

The substitution degree (SD) of tocopherol molecules to HA was around 7% on molar basis, and this low SD (<25%) indicated that the biodegradability and biocompatibility of HA was not affected by the tocopherol modification, and HA-Toco should retain similar delivery properties to that of native HA.[15] HA itself undergoes some self-association to form a loose gel-like network, with a particle size of about 12.2 nm for 30 kDa HA. With the hydrophilic HA backbone and the hydrophobic tocopherol, HA-Toco furtherly self-aggregates to form nanoparticles in aqueous solution. This self-association resulted in a nearly 30-fold size increase, as the particle size of HA-Toco was measured as 353±18 nm (Table 1), which was consistent with the measurement of previous studies (350-400 nm).[9,33]

R848-Toco was encapsulated into the hydrophobic core of HA-Toco. The formulated nanocomplex formed a stable homogeneous nano-emulsion after rehydration, which was readily injectable. Since drug suspensions and oily emulsions are common vehicles for depot injections (e.g. Depo-Provera® and Fluanxol® Depot), the evaluation of this formulation was continued.[1] R848-Toco in the formulated sample was close to the targeted concentration (98.2±3.9% encapsulation efficiency). In aqueous solution, the particle size of R848-Toco/HA-Toco was measured as 525±42 nm (Table 1), which was larger than the vehicle HA-Toco (353±18 nm), suggesting that the R848-Toco conjugates were embedded into the inner core of HA-Toco polymeric nanoparticles. A homogenous nanoparticle population was indicated by a polydispersity index (PDI) of less than 0.2. All sizing measurements were taken from three separately prepared samples, confirming the consistency of the quantification batch-to-batch.

TABLE 1

DLS measured hydrodynamic particle sizes and polydispersity index (PDI)

| Sample | Z-average (d. nm) | PDI |
|---|---|---|
| HA-Toco (10 mg/mL) | 353 ± 18 | 0.149 ± 0.033 |
| R848-Toco (10 mg/mL)/HA-Toco (15mg/mL) | 525 ± 42 | 0.098 ± 0.016 |

Example 2: Structure-Activity Relationship of Imidazoquinolines; Identification of Potent C7 Substituted Imidazoquinolines Small molecule agonists of TLR7/8, such as imidazoquinolines, are validated agonists for the treatment of cancer and for use in vaccine adjuvants. Imidazoquinolines have been extensively modified to understand the structure-activity relationship (SAR) at the N1- and C2-positions resulting in the clinical drug imiquimod, resiquimod (also referred to as "R848"), and several other highly potent analogues. However, the SAR of the aryl ring has not been fully elucidated. This example examines the SAR of C7-substituted imidazoquinolines. Compounds of the present technology not only demonstrated that TLR7/8 tolerate changes at the C7 position but such changes can increase potency and change their cytokine profiles. The most notable TLR7/8 agonists developed from this study 5, 8, and 14 are up to 4-fold and 2-fold more active than resiquimod for TLR8 and/or TLR7, respectively, and up to 100-fold more active than the FDA approved imiquimod for TLR7.

Toll-like Receptors (TLRs) are a validated target for developing new immunostimulatory drugs. TLRs are a part of the innate immune system, called pattern recognition receptors (PRRs), that help prime the adaptive immune system.[27] PRRs detect pathogen-associated molecular patterns (PAMPs), which are conserved features common to many pathogenic microorganisms and viruses, but not expressed by the host organism (e.g. flagellin, lipopolysaccharides, bacterial DNA, and viral RNA).[35] In humans, there are 10 TLRs (1-10), which can broadly be separated into endosomal (TLR3, 7, 8 and 9) and cell surface receptors (TLR1, 2, 4, 5, 6 and 10).[35] The endosomal TLRs are natively activated by nucleic acid constructs not normally found or tightly controlled in the host, including double stranded RNA (TLR3), single stranded RNA (TLR7/8) and unmethylated CpG oligodeoxynucleotides (TLR9).[34] TLR7/8 are expressed in a subset of immune system leukocytes, including monocytes, macrophages, natural killer (NK) cells, and B- and T-lymphocytes.[24] TLR7/8 are canonical activators of the MyD88 pathway, which induces expression of pro-inflammatory type I interferons.[5] Activation of Toll-like Receptor 7 and 8 (TLR7/8) is associated with a Th-1 biased (cell-mediated) immune response, as opposed to a Th-2 humoral (antibody) response.[63] The cell-mediated immune response primarily helps eliminate intracellular pathogens, such as viruses, that may have limited exposure to humoral defenses.[7] The cell-mediated immune response is also crucial in the host regulation of improper cell replication and development of cancers.[6] For these reasons, small molecule agonists of TLR7/8 are highly sought after for the development of new vaccine adjuvants or antitumor agents.

Native ligands of TLR7/8 are guanosine and uridine-rich sequences common to viral single stranded RNA (ssRNA).[23] In the case of TLR7, guanosine binds a first docking site on the receptor, which primes a second site to bind uridine with subsequent dimerization and activation.[67] Binding of either guanosine or uridine alone is insufficient for activation. However, several small molecules have been described with sufficient affinity to activate TLR7/8 after binding of the first (guanosine) site alone, including imidazoquinolines, thiazoquinolines, benzoazepines, benzonaphthyridine, and guanine analogs.[20,21,25,64] The most recognizable imidazoquinolines are imiquimod and resiquimod (shown below). Imiquimod is the only FDA-approved TLR7 agonist and is the active ingredient in the topical ointment Aldara®, used to treat skin conditions such as superficial basal cell carcinoma and actinic keratosis.[43] Resiquimod is a dual TLR7/8 agonist that is in clinical trials for treatment of cutaneous T-cell lymphoma and melanoma.[49,51,61]

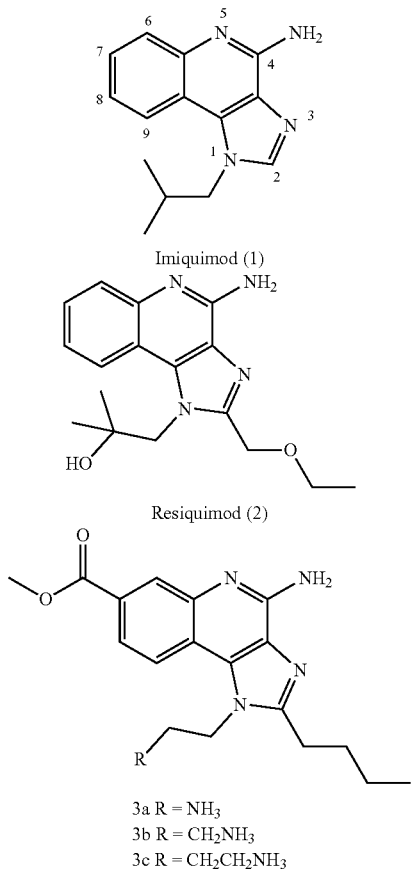

Since imidazoquinolines have been proven to be useful immunostimulants, significant effort has been put forth to develop the structure-activity relationship (SAR) and to help identify potent and effective imidazoquinolines suitable for vaccine adjuvants and cancer treatments.[36,53,55,56,57] To date, the SAR investigations of imidazoquinolines have mostly focused on the N1 and C2 positions. The N1 position has been substituted with several different groups with differing results of selective TLR7, TLR8 or mixed TLR7/8 agonists.[19,36,53,57] TLR7 tolerates many changes at N1 and C2 and are not required for activity, however, substitutions at these positions typically increase potency.[19,57] TLR8 typically prefers N1 alkyl hydroxy substituents and either C2 n-butyl or n-pentyl with n-pentyl being more potent to produce mixed TLR7/8 agonists.[53] The C4 amine is required for activity as changes to this position result in no activity.[19] One position that has been relatively under-explored is the C7 position. Gerster et al. found that imidazoquinolines with a C7 methoxy, hydroxyl, and/or methyl group retained similar IFNα production when compared to 1.[19] Recently, Larson et al. showed that imidazoquinolines 3a-c are TLR8 selective.[36] In addition, the disclosure of the crystal structure of 2 bound to the TLR8 receptor provides further evidence that the C7 position might tolerate changes better than other aryl positions.[60] Various C7 substituted derivatives were evaluated for their activities in TLR7/8 reporter cell lines and their cytokine induction in donor canine leukocytes. In this study, the influence of electronic effects at the C7 position through the addition of electron withdrawing and electron donating groups (EWGs and EDGs) was explored.

Secreted Embryonic Alkaline Phosphatase ("SEAP") Reporter Assay for hTLR-7 and hTLR-8 Activity The analogs (4-14) were screened for TLR7 and TLR8 activity in vitro using commercially available human embryonic kidney cells (HEK293) stably co-transfected to express either hTLR7 or hTLR8, along with a secreted embryonic alkaline phosphatase (SEAP) reporter gene induced by NF-κB (HEK-Blue™, InvivoGen). TLR activation induces NF-κB production and subsequent SEAP secretion, which is measured using HEK-Detection media (InvivoGen) containing a colorimetric substrate for SEAP (UV-Vis, 637 nm). Transfected null cell lines lacking the hTLR7 or hTLR8 receptors but possessing the NF-κB induced SEAP reporter gene were used as a control to screen for non-specific activation of NF-κB (Table 2). Target compounds were not evaluated at concentrations higher than 100 µM due to solubility issues. None of the compounds tested showed activity in the Null 1-k and Null 1 controls, indicating no substantial NF-κB induction from endogenous, low level TLR expression by HEK293 cells.

The experiments followed manufacturer protocol as follows: SEAP levels were measured via absorbance at 637 nm using HEK-Blue Detection cell culture medium (InvivoGen), which contains a SEAP-specific colorimetric substrate. Compound stock solutions were first diluted in sterile DMSO at a concentration of 10 mM. Lower concentrations were prepared by serial dilution of the initial 10 mM stock samples into sterile DMSO and these solutions (22 µL) were subsequently diluted into sterile $H_2O$ (198 µL) using a BioTek Precision XS pipetting system. HEK-Blue hTLR7, HEK-Blue hTLR8, Null 1-k, and Null 1 cell suspensions in sterile HEK-Blue Detection medium were prepared at a density of 220,000 cells per mL. Clear bottom, 96-well tissue culture treated plates (Corning) were seeded with hTLR7 and Null 1-k or hTLR8 and Null 1 cell suspensions (180 µL/well), after which 20 µL of the various sample concentrations in 10% v/v DMSO/$H_2O$ were added (20 µL) in quadruplicate wells to yield the desired testing concentration in 1% v/v DMSO cell suspension. Plates were incubated at 37° C. and 5% $CO_2$ in the dark. Absorbance measurements were taken at 637 nm at 12 hours, 4 replicates per concentration point, per cell line (hTLR7, hTLR8, Null 1-k, Null 1). Three independent measurements on different days were performed for each analog. Positive and negative controls were resiquimod and DMSO, respectively, and were tested alongside analogs 4-14 during independent measurements.

Figure 2:
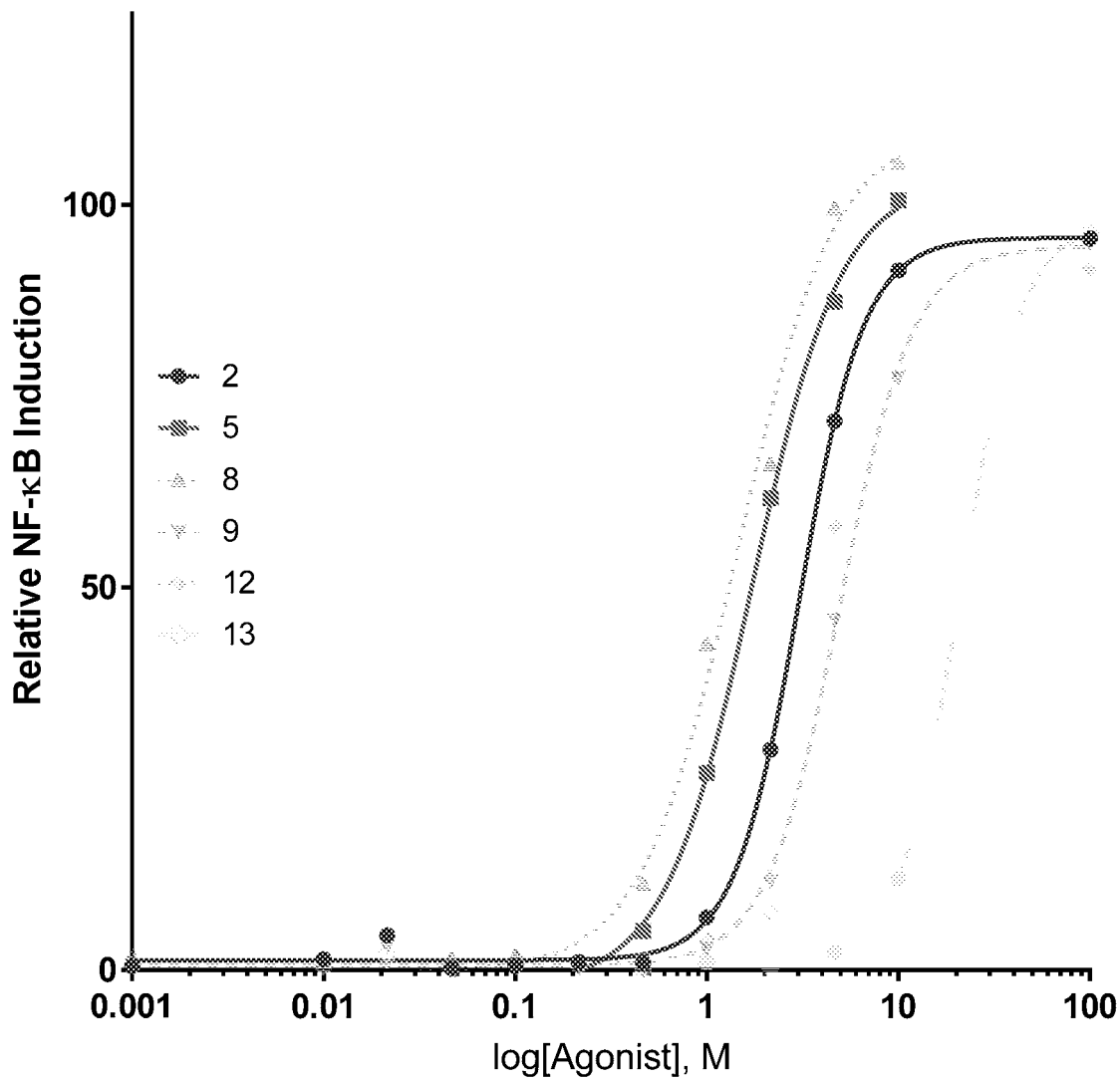
FIG. 2 shows a dose response curve of TLR8 activation for compounds of the present technology.
Figure 3A:
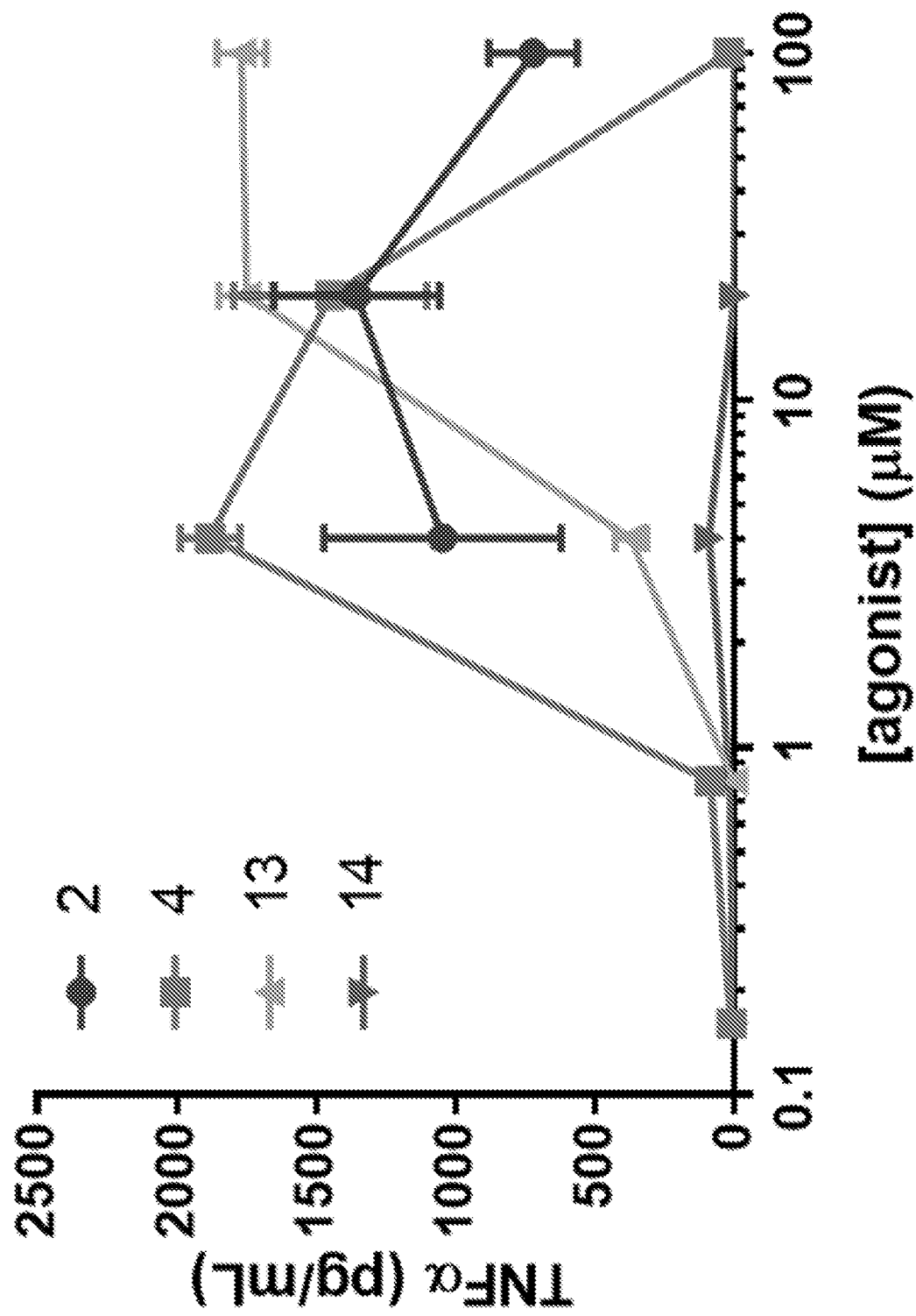
FIGS. 3A-3D show secretion levels of various cytokines (FIG. 3A: TNFα.
Figure 3B:
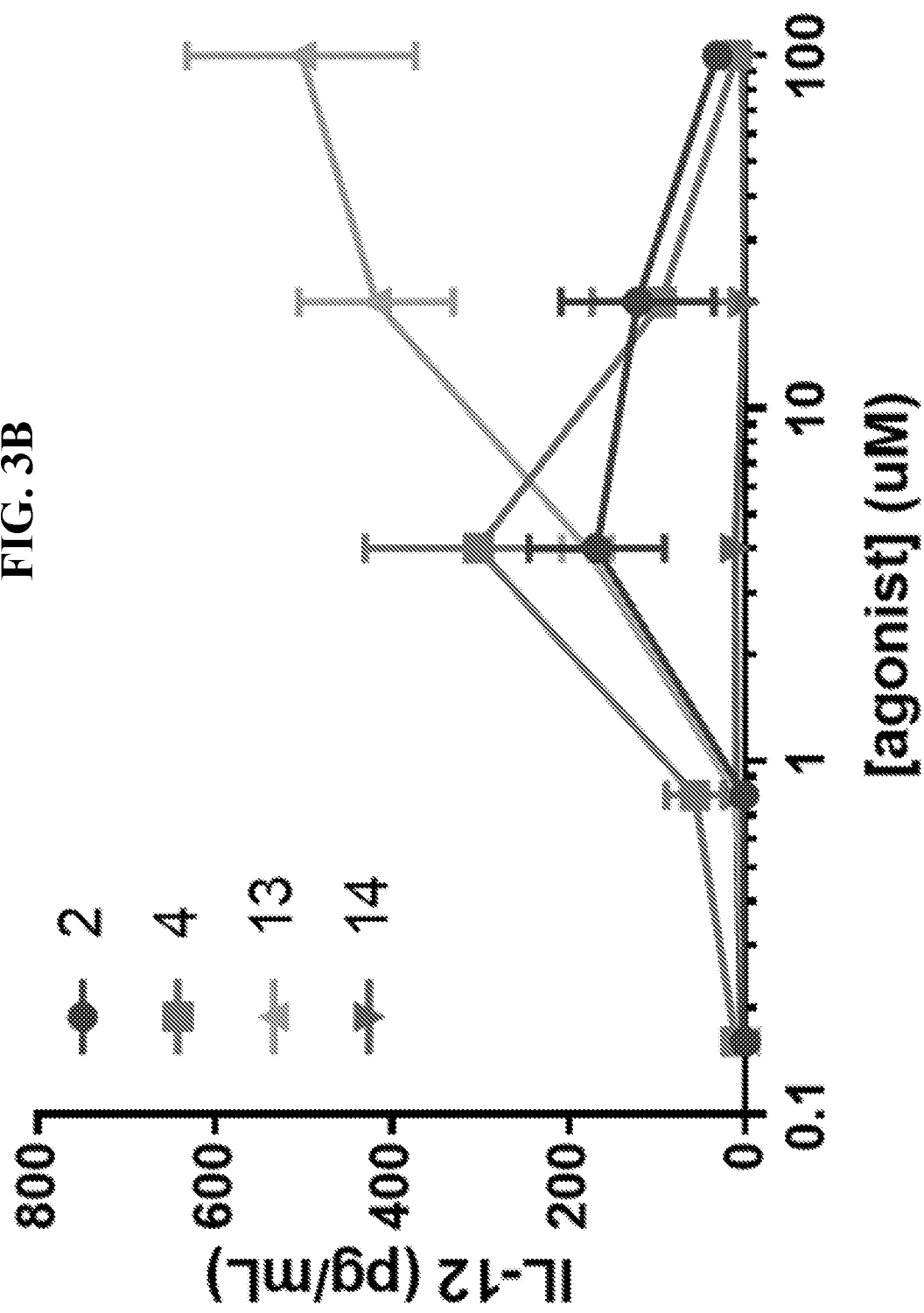
Figure 3C:
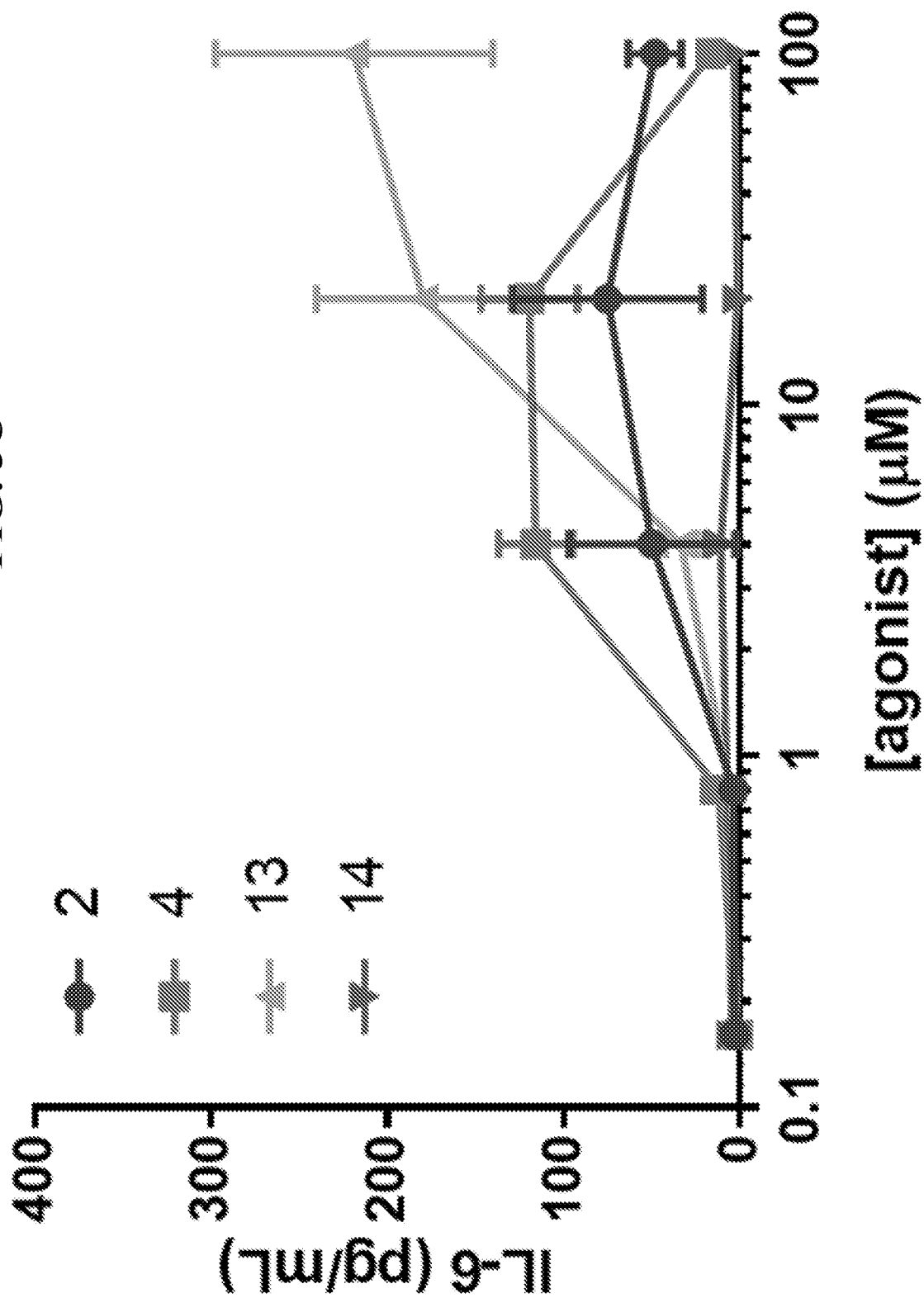
Figure 3D:
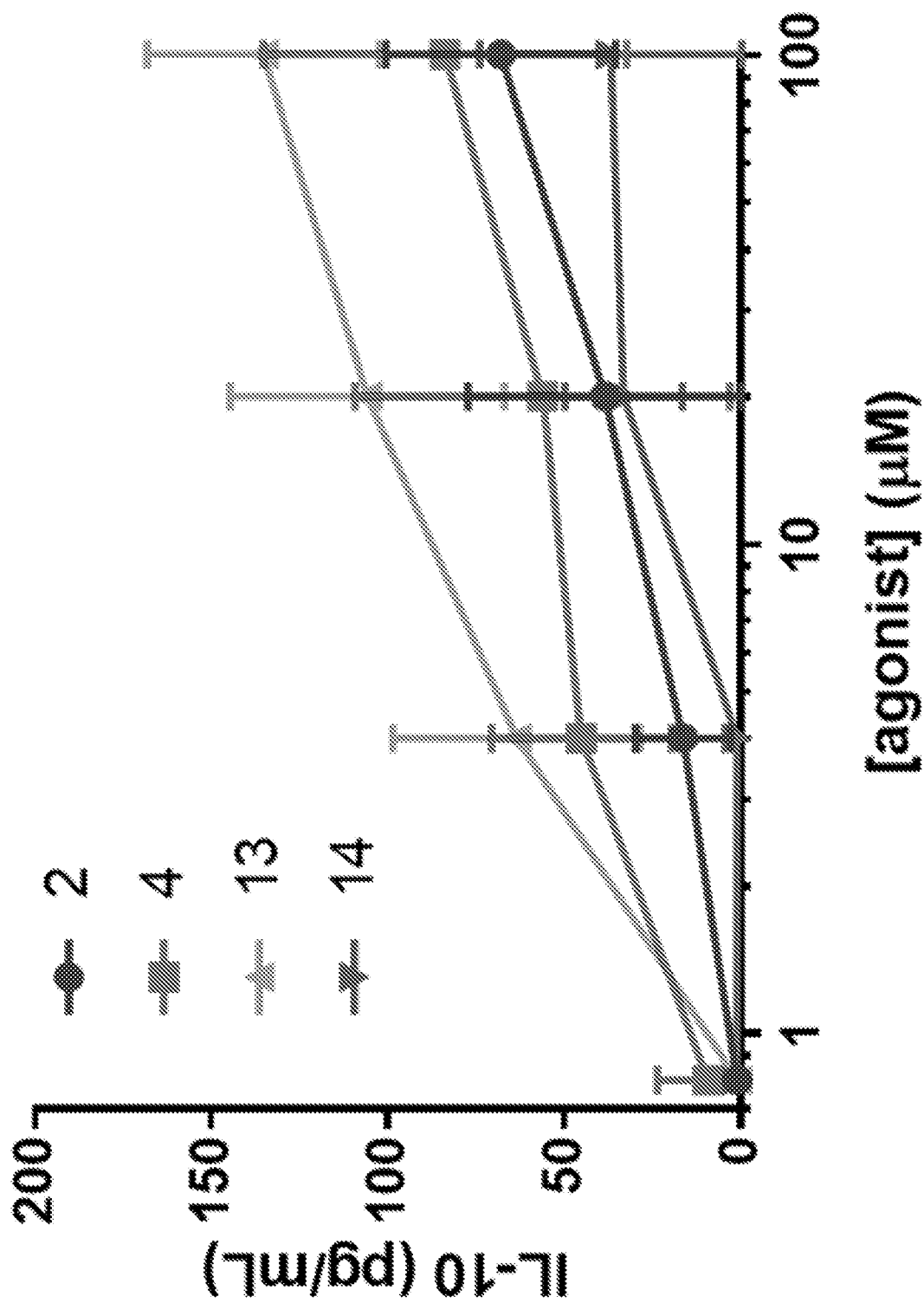
Figure 4B:
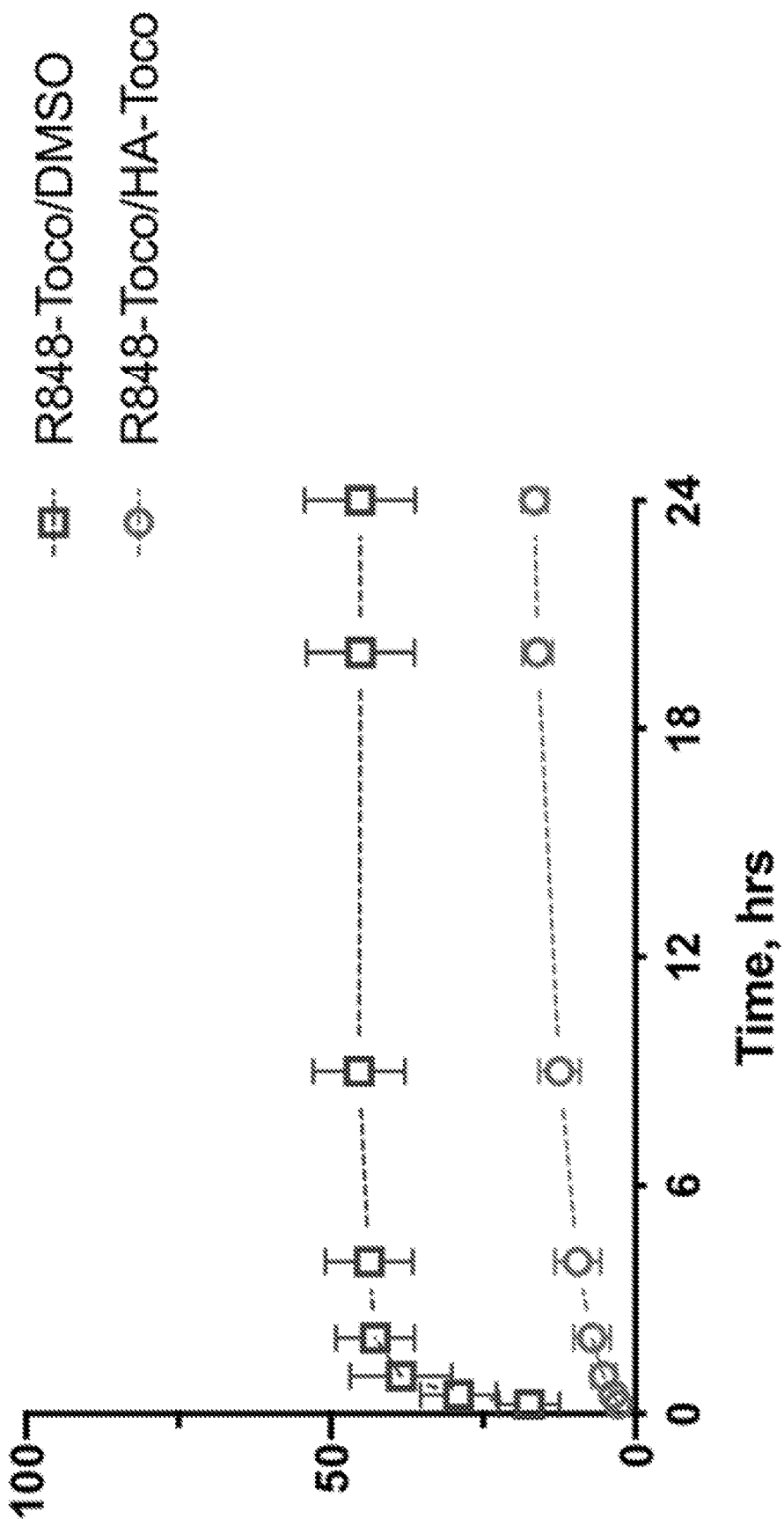
Figure 4C:
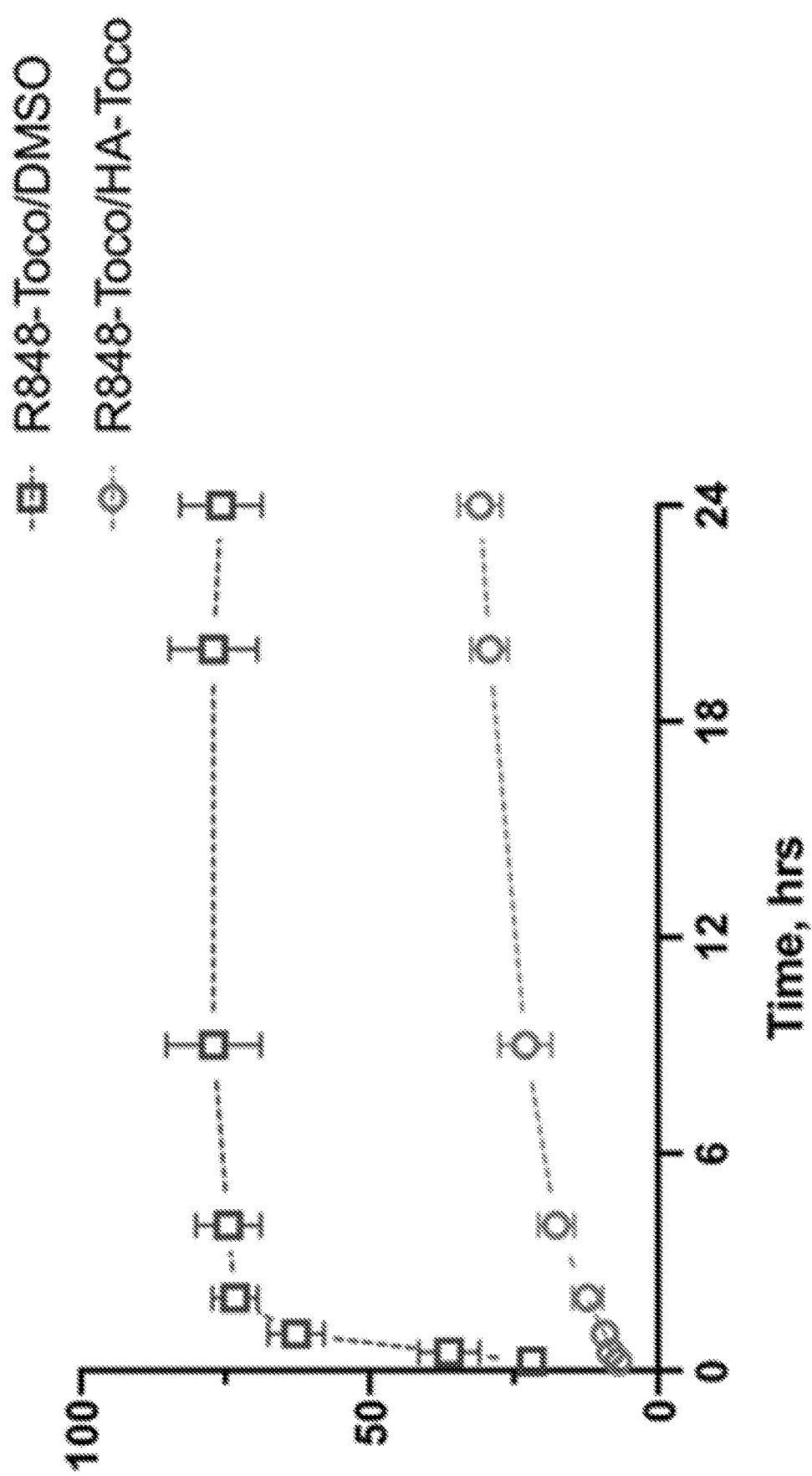
Figure 5A:
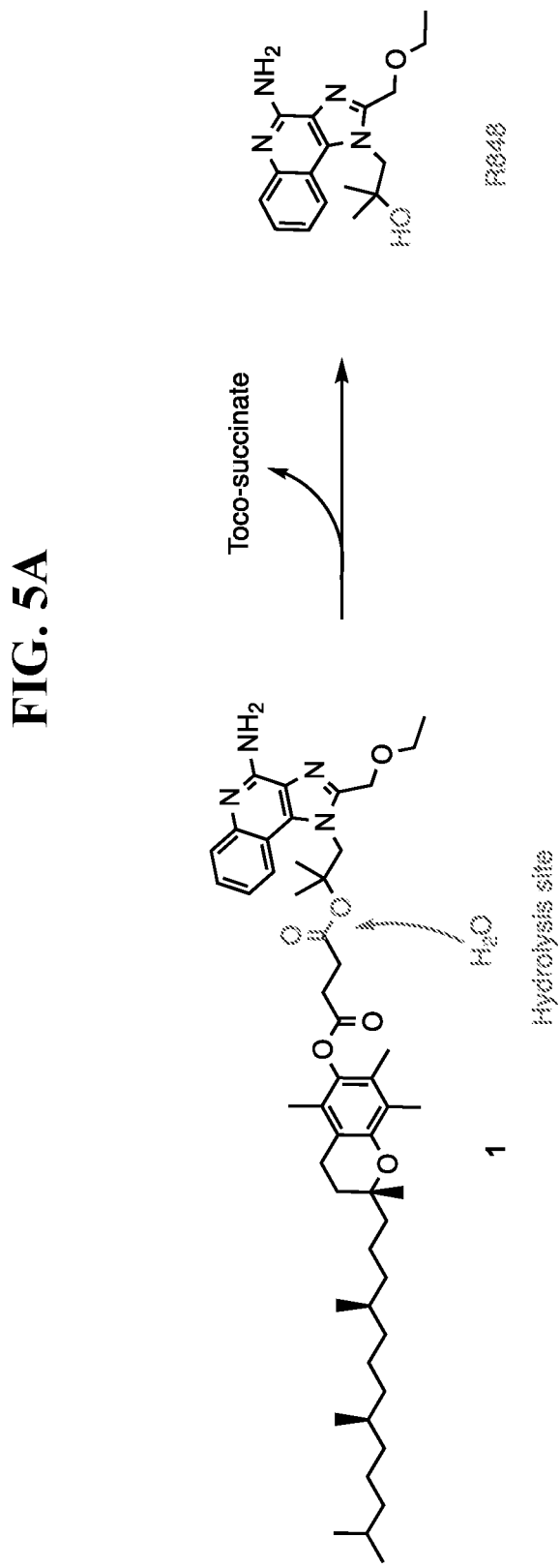
FIG. 5A shows a schematic illustration of proposed R848-Toco hydrolysis. Hydrolyzed products did not contain any R848-succinate and free tocopherol.
Figure 5B:
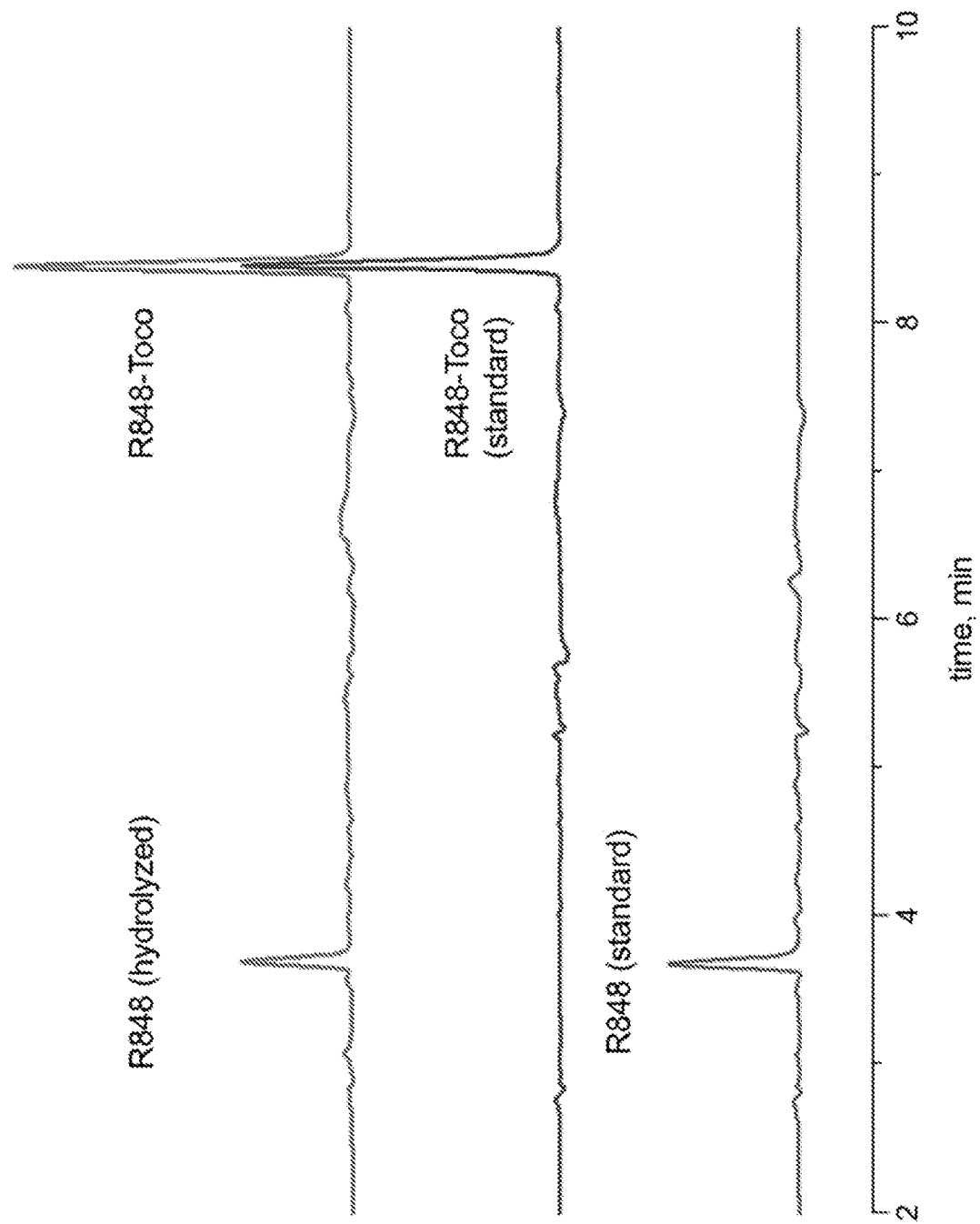
FIG. 5B shows HPLC chromatogram of hydrolysis sample at 8 h. R848-Toco was hydrolyzed to R848, which was the only observed hydrolyzed product (top trace). Standards were measured to confirm the peak (center trace: R848-Toco; bottom trace: R848).

Corresponding well absorbance values for each concentration tested were averaged with respect to days tested, and the average relative NF-κB induction (UV-Vis, 637 nm) of the null cell lines (Null 1-k or Null 1) were subtracted from the respective average TLR expressing cell line (hTLR7 or hTLR8) absorbance averages. The absorbance data observed was then normalized to that day's respective Resiquimod controls based on 100% activity to better compare the biological replicates. The three independent, normalized averages for each analog were then pooled, and the data was fit using the Hill-Slope model (GraphPad Prism v7.0) using the non-linear fit from the [Agonist] vs. response—Variable Slope (four parameters) with a hill slope constrained to less than 3. These gave the dose response curves for TLR7 (FIG. 1) and TLR8 (FIG. 2), along with the $EC_{50}$ values reported in Table 2.

As expected, imiquimod (1) and resiquimod (2) were found to be agonists for TLR7 and TLR8 receptors with values consistent with previous reports.[19,36,53,55] It was observed that (1) TLR7 is more tolerant to changes than TLR8; (2) tertiary alcohols at the N1 position tend to increase the TLR7 activity when compared to those without the tertiary alcohol; and (3) TLR8 activity requires the tertiary alcohol at N1.[55] It was also observed that when C2 contains the ether substitution, TLR7/8 activity decreases when compared to the C2-butyl. The changes made at C7 do not cause a change in the trend for N1 and C2 sites.

TABLE 2

TLR7/8 Agonist Activities of Analogs 4-13[a]

| Compound | $EC_{50}$ (μM) ± SD[b] | | Cytokine (pg/mL) ± SD[b] | | | | | |
|---|---|---|---|---|---|---|---|---|
| | TLR7 | TLR8 | TNFa | IL-12 | IL-6 | IL-10 | IL-2 | IFNg |
| 1 | 6.8 ± 0.8 | 25 ± 3 | 1200 ± 140 | 300 ± 48 | 16 ± 2 | 85 ± 37 | 18 ± 6 | |
| 2 | 0.25 ± 0.03 | 3.0 ± 0.3 | 190 ± 30 | 2800 ± 520 | 380 ± 80 | 21 ± 2 | 120 ± 12 | 26 ± 7 |
| 4 | 0.11 ± 0.01 | >100[c] | 49 ± 9 | 746 ± 130 | 500 ± 140 | 37 ± 13 | 30 ± 29 | 0 |
| 5 | 0.081 ± 0.009 | 1.7 ± 0.3 | 64 ± 12 | 2000 ± 160 | 290 ± 63 | 14 ± 2 | 82 ± 56 | 14.5 ± 6 |
| 6 | 0.30 ± 0.02 | >100 | 91 ± 20 | 760 ± 50 | 240 ± 67 | 14 ± 4 | 63 ± 44 | 7 ± 1 |
| 7 | 0.91 ± 0.09 | >100 | 114 ± 25 | 781 ± 40 | 280 ± 81 | 20 ± 1 | 50 ± 22 | 5 ± 5 |
| 8 | 0.084 ± 0.007 | 1.5 ± 0.2 | 22 ± 4 | 1700 ± 330 | 230 ± 44 | 7 ± 6 | 55 ± 30 | 13 ± 10 |
| 9 | 0.63 ± 0.03 | 4.9 ± 0.6 | 70 ± 8 | 1900 ± 130 | 320 ± 76 | 12 ± 3 | 76 ± 59 | 16 ± 2 |
| 10 | 0.99 ± 0.40 | >100 | 10 ± 1 | 920 ± 170 | 350 ± 95 | 37 ± 10 | 60 ± 41 | 13 ± 5 |
| 11 | 6.8 ± 0.7 | >100 | 7 ± 1 | 190 ± 62 | 71 ± 20 | 6 ± 2 | 57 ± 14 | 4 ± 3 |
| 12 | 0.79 ± 0.23 | 3.9 ± 0.2 | 44 ± 10 | 418 ± 72 | 290 ± 77 | 14 ± 3 | 45 ± 22 | 12 ± 4 |
| 13 | 3.5 ± 0.7 | 27 ± 6 | 80 ± 20 | 13 ± 3 | 214 ± 69 | 6 ± 3 | 46 ± 42 | 0.2 ± 0.4 |
| 14 | 0.073 ± 0.005 | >100 | 270 ± 70 - | 102 ± 65 | 330 ± 92 | 17 ± 3 | 79 ± 19 | 9 ± 8 |
| Vehicle | | | 8 ± 2 | 18 ± 8 | 310 ± 90 | 33 ± 16 | 47 ± 20 | 0.4 ± 0.7 |

[a]Average $EC_{50}$ values were determined from three independent measurements at 10 or more concentrations, performed in quadruplicate using either hTLR7 or hTLR8 transfected HEK-Blue cells along with corresponding Null controls.
[b]Cytokine production was measured in triplicate at 20 μM,
[c]>100 = no activity observed at 100 μM.

TLR7/8 continues to tolerate C7 substitutions when the N1 and C2 are substituted appropriately.[53] The most important finding is that there is a general trend for C7 substitutions. It has been observed in this study that EDGs are stronger activators of TLR7/8 than EWGs. For TLR7 the range was from no statistically significant difference to a 13-fold decrease. For TLR8 the range was from no statistically significant difference to a 9-fold decrease. The observed decrease in activity could be due to the electron deficiency of the imidazoquinoline ring system.

Some notable compounds are the C7-methoxy compounds, 4 and 5, and the C7-hydroxyl, 14, as these are substantially more active agonists, which suggests that the increase of electron density of the imidazoquinoline ring system may be increasing the hydrogen bonding interactions of the C4-amine and N5 pyridine nitrogen, or the increase could be contributed to a potential hydrogen bond from the neighboring tyrosine in the binding pocket.[60]

The imidazoquinolines were further screened for cytokine production in canine peripheral blood mononuclear cells (cPBMCs). The agonists at 20 μM concentrations were evaluated for TNFα, IL-12, IL-6, IL-10, IL-2, and IFNγ production by ELISA following incubation with 2×10⁶ PBMC/mL for 29 hours. TNFα and IL-12 were chosen as they are typically seen in a Th-1 cytokine response. None of the compounds studied activated IL-6, IL-10 or IL-2 significantly above vehicle.

Peripheral blood from a healthy canine donor was obtained with appropriate informed consent of the owner and under approved institutional guidelines. Blood (8 mL per tube) was drawn via sterile venipuncture into a BD Vacutainer cell preparation tube containing sodium heparin (BD Biosciences). PBMCs were isolated within one hour following procurement by density gradient centrifugation according to the manufacturer protocol and resuspended to 2.22×10⁶ cells/mL in sterile RPMI 1640 medium with L-glutamine (Gibco) supplemented with 100 U/mL penicillin, 100 μg/mL streptomycin (Corning) and 10% (v/v) heat-inactivated Fetalgro (RMBIO). Corning 3917, 96-well tissue culture treated plates were seeded with the PBMC suspension (180 μL/well), 20 μL of the serially diluted TLR agonists were added in triplicate to yield the desired concentrations in a 1% (v/v) DMSO cell suspension. Cells were incubated at 37° C. in 5% $CO_2$ for 9 hours (FIGS. 3A-3D) or 29 hours (Table 2) after which supernatants were removed and frozen at −80° C. Cytokine secretion levels were measured by ELISA (Duoset, R&D Systems) according to the manufacturer protocol. Samples and standards (n=3) were thawed and plated onto a Maxisorp flat-bottom, 384-well plate (Thermo Scientific) using a BioTek Precision XS pipetting system. Cytokine concentrations were determined by a hyperbolic or four-parameter logistic non-linear regression of the recombinant standards and subsequent interpolation using Graphpad Prism 7.0.

As expected nearly all compounds in this study activated IL-12 and TNFα. A trend is observed that IL-12 production increases when the tertiary alcohol of the N1 position is present, suggesting that TLR8 helps increase IL-12 production. Also having a tertiary alcohol at the N1 position appears to activate INFγ production. It is also observed that EDGs are typically stronger activators of TNFα and IL-12 when compared to EWGs. One compound that is interesting is 14. It did not follow the trends above. It has one of the highest TNFα responses but one of the lowest IL-12 responses observed despite that it is strongly electron donating and one of the strongest activators of TLR7. Possible explanations are time courses changes in the cytokine response, or other secondary interactions of the compound within cell lines.

Conclusion

In this example the SAR of the C7 position of imidazoquinolines was further evaluated by synthesizing compounds 4-14 with overall yields around 30% at the gram scale. Changes to the N1 and C2 positions combined with the C7 position maintained activity trends consistent with previous findings. TLR7/8 tolerates all of the target C7 substitutions made in this study when the N1 and C2 are substituted appropriately. EDGs at C7 of imidazoquinolines are stronger activators of TLR7/8 when compared to EWGs. This study also found TLR7/8 activating substitutions generally increased TNFα and IL-12 cytokine responses and that TLR8 activation potentiated an IFNγ response. However, one compound, 14, breaks this trend. Despite being one of the strongest TLR7 selective agonists 14 barely potentiates any cytokine induction. Notable compounds produced from this study are 5, 8, and 14 which are up to 4-fold and 2-fold more active than resiquimod for TLR8 and/or TLR7, respectively, and up to 100× more active than the FDA approved imiquimod for TLR7. This is the first report of high potency agonists based on modifications at the C7 position using the methoxy, chloro, and nitrile functional groups. The results in cPBMCs show that different C7 functionalities alter the agonist-cytokine response profile.

Example 3: Formulation and Preclinical Evaluation of Toll-Like Receptor 7 Agonist Conjugate as an Anti-Tumoral Immunomodulator In this study, a novel aqueous depot formulation of the TLR7/8 agonist R848 has been prepared and evaluated. To increase the retention of R848 while maintaining its agonist activity, R848 was covalently linked to tocopherol (vitamin E) to form an R848-tocopherol conjugate (R848-Toco), producing a larger lipophilic molecule that can release free R848 molecules in aqueous conditions. This conjugate, which is poorly soluble in water due to the addition of tocopherol, requires an aqueous formulation to administer by injection. Hyaluronic acid (HA) is an endogenous mucopolysaccharide that has been applied as a useful vehicle for anti-cancer compounds due to its high water solubility, biocompatibility, and specific interaction with CD44 receptors expressed on tumor cells.[15] In this study, a novel hyaluronan-based polymer was able to form water-soluble complexes with poorly soluble R848-Toco as a readily injectable formulation. The formulated nanocomplexes allowed for controlled and localized delivery of the agonist while avoiding rapid dispersion.

Materials: Resiquimod (R848), HEK-Blue cell lines and QUANTI-blue™ were purchased from Invivogen (San Diego, CA, USA). 32 kDa hyaluronic acid was purchased from Contipro C (Dolni Dobrouc, Czech Republic). Synthesis compounds and reagents, including (+)-α-tocopherol, (+)-α-tocopherol succinate, 1-ethyl-3-(3-dimethylaminopropyl)carbodiimide hydrochloride (EDC·HCl), triethylamine (TEA), N,N'-dicyclohexylcarbodiimide (DCC), 4-dimethylaminopyridine (DMAP), N-(tert-butoxycarbonyl) glycine (Boc-Gly-OH), trifluoroacetic acid (TFA), tetrabutylammonium hydroxide (TBA-OH), 1-hydroxybenzotriazole hydrate ($HOBt{\cdot}H_2O$), anhydrous dichloromethane ($CH_2Cl_2$), dimethylformamide (DMF), silica gel 60 and thin-layer chromatography plates were purchased from Sigma Aldrich (St. Louis, MO, USA). Solvents for column chromatography, HPLC grade solvents, sterile water for injection (WFI) and cell culture supplies were purchased from Fisher Scientific (Hampton, NH, USA). Zorbax C8 columns were purchased from Agilent (Santa Clara, CA, USA). SnakeSkin® dialysis tubing and dialysis supplies were purchased from Thermo Scientific (Waltham, MA, USA). Alexa Fluor® antibodies were purchased from BioLegend (San Diego, CA, USA).

In Vitro Release Kinetics

Solutions (1 mL) of free R848 in DMSO, R848/HA-Toco in water, R848-Toco in DMSO, and R848-Toco/HA-Toco in water, with a concentration of 1 mg/mL on R848 basis were dialyzed using SnakeSkin® dialysis tubing (MWCO 3500 kDa) against 30 mL of phosphate buffered saline release medium (PBS, 10 mM sodium phosphate, 137 mM NaCl, pH 7.4) with 0.5% (w/v) polysorbate 80 at 37° C. At predetermined time points, 1 mL aliquots of release medium were sampled and replaced with an equal volume of fresh medium. The samples were kept frozen (−20° C.) until HPLC analysis.

Results: The in vitro release profiles of R848 and R848-Toco from the HA-Toco were studied using a dialysis method. To avoid the solubility limitations of the free drug and to maintain sink conditions, 80% of the release medium was sampled at regular intervals and immediately replaced with fresh medium. The release of parent R848 formulated with HA-Toco was tested in PBS media, with free R848 dissolved in DMSO as a control. Similar release kinetics were observed whether R848 was formulated with HA-Toco or without (t1=2, release=2.5 h), and in both conditions nearly 100% of the agonist was released over 24 h (FIG. 4A). Thus, although HA-Toco could formulate the poorly soluble R848 parent drug, it did not provide any prolonged release.

When the R848-Toco conjugate was loaded into HA-Toco vehicle, the release was sustained likely due to the association between tocopherol molecules on the cargo and the carrier. The formulated R848-Toco/HA-Toco had a much slower release compared to the free R848 (FIG. 4B). Unformulated R848-Toco, dissolved in DMSO, showed a burst release within the first half hour. The low extent of total free drug released was due to the extensive precipitation of the poorly soluble R848-Toco in the dialysis bag. Polysorbate 80 (Tween 80) was then added into the release medium to improve the solubility of the conjugate. In the 0.5% w/v polysorbate 80 solution of PBS, 33% of the R848-Toco/HA-Toco was released over the first 24 h, whereas the unformulated control group released 76% (FIG. 4C). Since HA-Toco provided a prolonged release of R848-Toco but had little effect on the release of the parent R848, the interaction between the conjugate R848-Toco and the vehicle HA-Toco was most likely due to the association between lipophilic tocopherol molecules.

Hydrolysis

For hydrolysis, R848-Toco (0.1 mg) was dissolved in 1 mL of DMSO, and the solution was added into 9 mL of hydrolysis media (PBS or 0.5% (w/v) polysorbate 80/PBS). The solution was then rapidly mixed and filtered using a syringe filter (0.22 μm×13 mm, nylon). The filtrate was then incubated at 37° C. under agitation (250 rpm). At predetermined time points, 50 μL of the solution was sampled and analyzed immediately by HPLC.

R848 and Toco were conjugated using a succinate linker, with the advantage that the parent R848 can be released through the ester bond degradation upon hydrolysis (FIG. 5A). In the hydrolysis study, hydrolysis of the ester bond between R848 and the tocopherol succinate appeared to be the dominant release mechanism. Based on HPLC analysis, both R848-Toco and free R848 were found in the media during the initial 8 h (FIG. 5B), and 72% of the R848-Toco was hydrolyzed to R848. The ester bond between R848 and tocopherol-succinate was more labile based on this observation, although it was also possible that any R848-succinate rapidly hydrolyzed to R848 before it could be detected. Most likely, the ester between the tocopherol and succinate is less labile, resulting from water exclusion by the bulky lipophilic tocopherol. A similar hydrolysis pattern was observed by Fu et al., as their paclitaxel-tocopherol (PTX-VE) conjugate hydrolyzed at the ester bond on the PTX side to release the free PTX, and using this conjugate they proved that the hydrolysis was favored by decreased steric hindrance and increase polarity, i.e. the site closer to the parent drug.[50] Therefore, in this aqueous formulation, only the intended R848 and the prodrug were observed, with no presence of undesired intermediates or degradants.

In Vitro TLR7 Activity Assay

TLR agonist activity was measured in a dose-response study using reporter cell lines expressing the human TLR7 (hTLR7). Human kidney cells (HEK-293) were transfected to express the hTLR7 gene, and co-transfected to express a SEAP reporter gene under the control of a NF-κB induced promoter.[26] The Null 1-k cell line, which does not express hTLR7 but is also transfected with the NF-κB/SEAP reporter system, was used as a control. The hTLR7 activity of R848-Toco, the formulation and its components were assessed using HEK-293 cells co-transfected with the hTLR7 gene and an inducible SEAP reporter gene along with the corresponding null control line (HEK-Blue™ hTLR7 and Null-1k cells, Invivogen). Cells were maintained in DMEM media with selective antibiotics according to the manufacturer protocol.[26] HEK-Blue™ cells were seeded into 96 well plates at a density of 220,000 cells/mL with 180 μL/well of culture medium. Stock solutions in DMSO were first serially diluted to seven concentrations (DMSO solutions further diluted into $H_2O$). Each well was stimulated with 20 μL of agonists or agonist-free controls (equivalent concentration of HA-Toco, D-α-Tocopherol succinate, PBS or 100 μM DMSO) at the determined final concentrations in 5 replicates. After 16 h of incubation at 37° C. in a 5% $CO_2$ atmosphere, 20 μL of the supernatant from each well was sampled and spiked into 180 μL of QUANTI-Blue™ solution followed by incubation for 1 h at 37° C. Relative hTLR7 activity was then analyzed by UV-Vis at 637 nm using a microplate UV reader (SpectraMAX GeminiXS, Molecular Devices, San Jose, CA, USA). For each compound and concentration, a corresponding sample was applied to the HEK-Blue™ Null-1k cell line. The TLR7 agonist activity was determined after averaging across hTLR7 replications and subtracting the averaged Null response.

Figure 6:
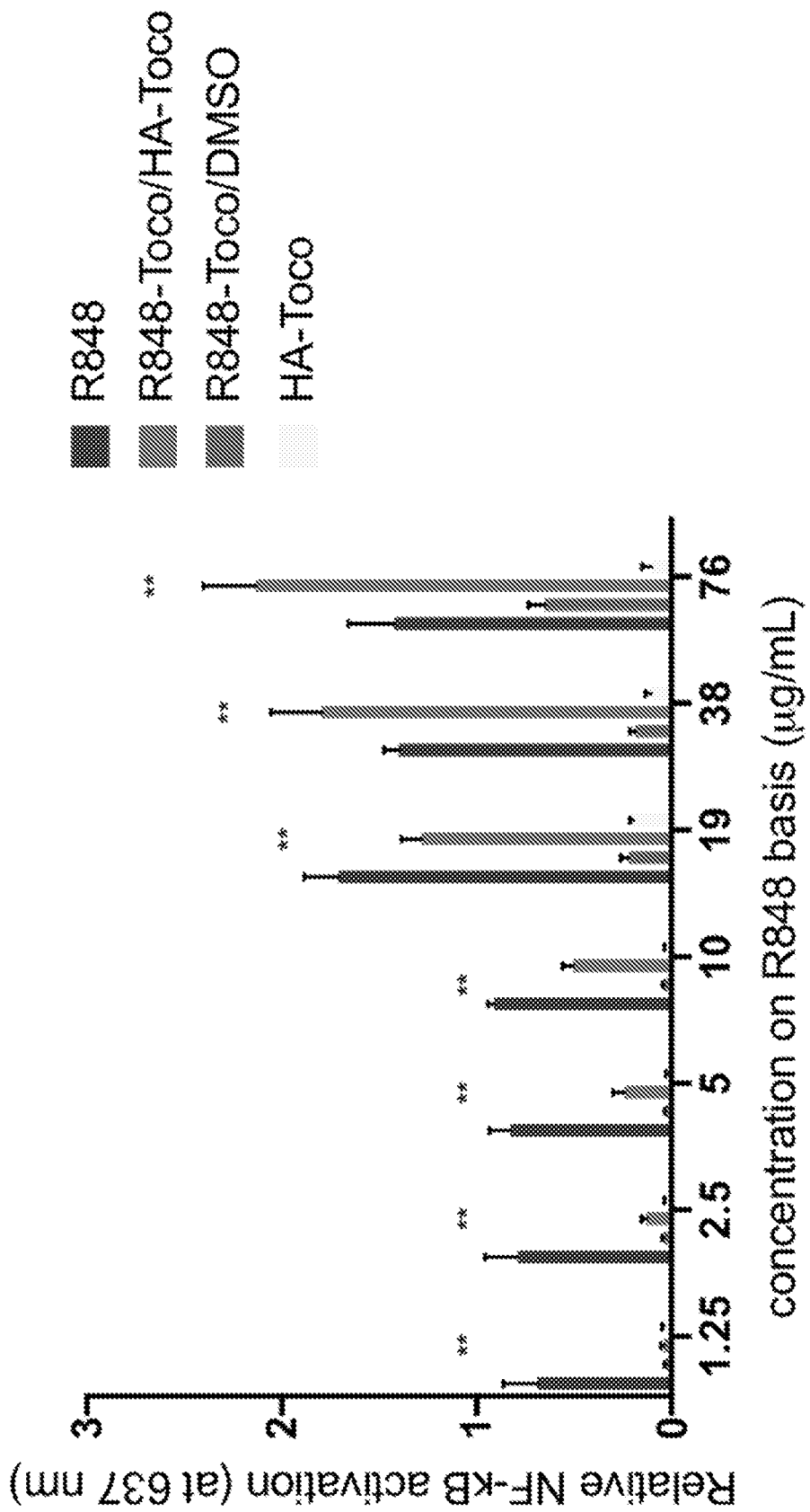
FIG. 6 shows NF-κB activation in human kidney HEK-293 hTLR7 cells. One way ANOVA ** p<0.01.

Activation levels were calculated as the difference between the average readings of the hTLR7 cell line and the Null 1-k cell line, to account for non-hTLR7 related induction of NF-κB. As shown in FIG. 6, the known agonist R848 induced strong dose-dependent activation as expected, and R848-Toco/HA-Toco was more active than free R848 at higher screened concentrations.[45] TLR7 agonists have been reported to be toxic at high concentrations in transformed cells lines, whereas the sustained release of the conjugate may prevent some toxicity.[8,38] At lower concentrations, R848-Toco/HA-Toco had weaker hTLR7 activity than free R848, although this may be due to the sustained release and that induction was measured after 16 h of exposure. The unformulated R848-Toco was much less active, possibly due to the poor solubility as observed in the kinetics studies, while formulating with HA-Toco improved the solubility and prevented R848-Toco aggregation in the aqueous solution. Non-conjugated Toco-succinate and blank HA-Toco vehicle did not induce any significant activation compared to PBS. Therefore, this study confirmed that R848-Toco, formulated with HA-Toco as an emulsion, maintained its TLR agonist activity. Furthermore, tocopherol and tocopherol succinate, which have anti-inflammatory properties and are known to inhibit NF-κB activation at higher concentrations had no significant effect on agonist activity in the conjugate or over the concentration range screened.[59,66]

In Vitro Cytokine Secretion Assay

As a TLR7/8 agonist, R848 binds to endosomal TLR7 and 8 receptors located on antigen presenting cells (APCs). The activation of APCs produces pro-inflammatory cytokines including TNF-α, type I IFN and IL-12. These cytokines, together with stimulated APCs that take up tumor antigens, enhance the activation of anti-tumor Th-1 immune responses that involve both $CD4^+$ T helper cells and $CD8^+$ cytotoxic T cells.[16] To evaluate the Th-1 associated cytokine production in vitro, isolated canine PBMCs were treated with R848, formulated or unformulated R848-Toco, and the secretion of TNF-α and IL-12 were measured by ELISA as markers of generalized inflammatory response. Canines were chosen as a model over mice because of the greater genetic similarity to humans and more similar immune systems.[46] Peripheral blood from healthy canine donors of 7-10 years age (similar to the age of typical canines with cancer[14]) was obtained with appropriate informed consent of the owner. Blood (8 mL per tube) was drawn via sterile venipuncture into a BD Vacutainer cell preparation tube containing sodium heparin (BD Biosciences). PBMCs were isolated within one hour following procurement by density gradient centrifugation according to the manufacturer protocol and resuspended to $3 \times 10^6$ cells/mL in sterile RPMI 1640 medium with L-glutamine (Gibco) supplemented with 100 IU/mL penicillin, 100 μg/mL streptomycin (Corning) and 10% (v/v) heat-inactivated Fetalgro (RMBIO). Corning 3917, 96-well tissue culture treated plates were seeded with the PBMC suspension (180 μL/well), 20 μL of the serially diluted R848 samples were added in triplicate and HA-Toco vehicle in duplicate to yield the desired concentrations in a 1% (v/v) DMSO cell suspension. Samples (n=6) and standards (n=3) were thawed and plated onto a Maxisorp flat-bottom, 384-well plate (Thermo Scientific) using a BioTek Precision XS pipetting system (BioTek Instruments, Winooski, VT, USA). Sample cytokine concentrations were determined by interpolation of a four-parameter logistic curve of the recombinant standards using GraphPad Prism 6. Cells were incubated at 37° C. in 5% $CO_2$/3% $O_2$ for 15 hours after which supernatants were removed and frozen at −80° C. Cytokine secretion levels were measured by ELISA (Duoset, R&D Systems, Minneapolis, MN, USA) according to the manufacturer protocol.

Figure 7:
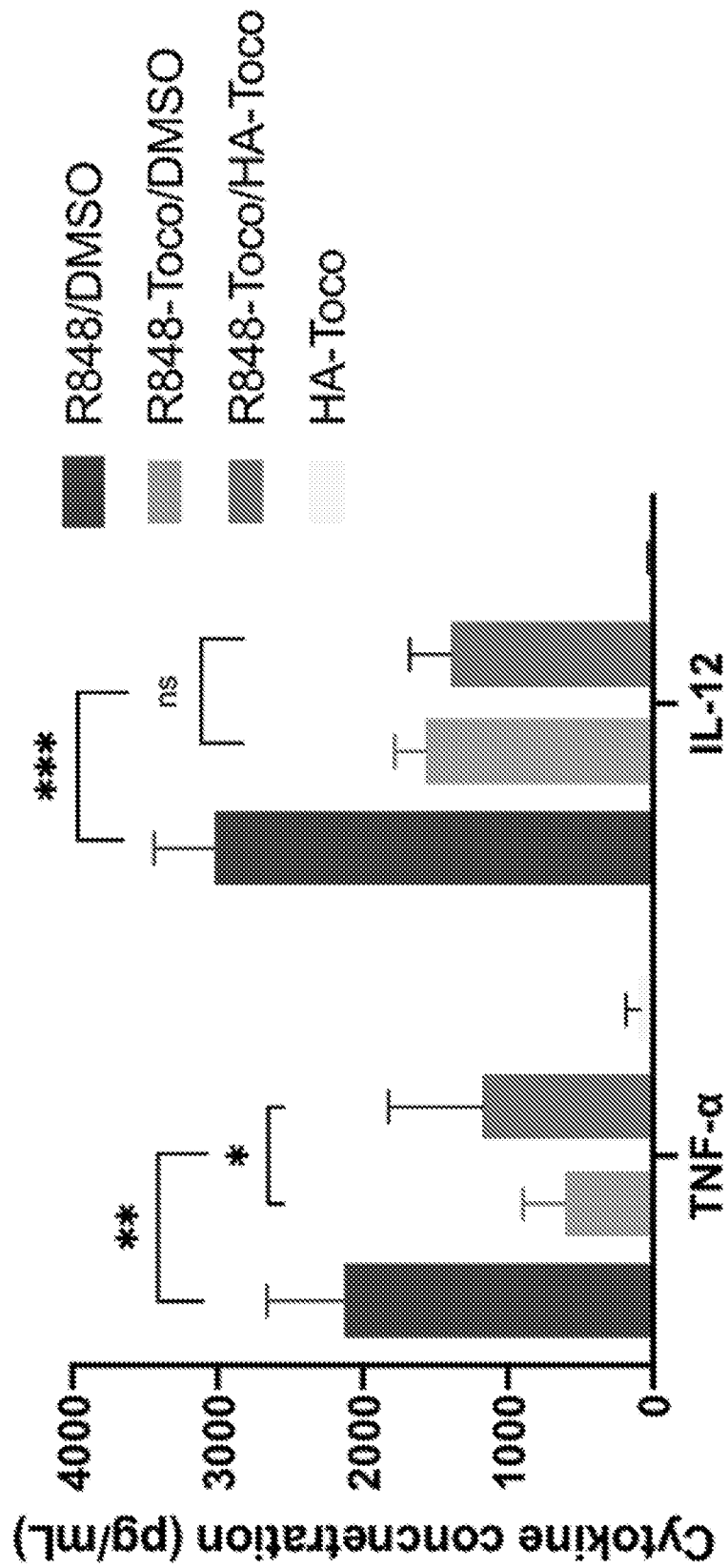
FIG. 7 shows cytokine secretion levels in canine PBMCs. ns=No significant difference was found for R848-Toco/DMSO and R848-Toco/HA-Toco in the IL-12 group.

Referring to FIG. 7, strong secretion of TNF-α was observed for free R848 and R848-Toco/HA-Toco, and to a lesser extent for unformulated R848-Toco. IL-12 levels were highest in free R848 samples, with a lower expression in R848-Toco/HA-Toco and unformulated R848-Toco groups. HA-Toco alone did not produce any notable expression of either TNF-α or IL-12. Taken together, R848-Toco retained its ability to induce the selected Th-1 related cytokines in canine PBMCs. Similar to the hTLR7 reporter cell line, the cytokine induction levels were slightly lower than parent R848 drug, potentially because during the measured time frame free R848 was only partially released from the nanocomplex.

Depot Effect of R848-Toco/HA-Toco

It was observed that a local injection of the R848-Toco/HA-Toco nano-emulsion forms a depot at the site of injection and releases the loaded agonist in a sustained fashion, producing prolonged and localized immune stimulation while minimizing systemic off-target effects. To test the localization effect, an ear inflammation test was conducted in healthy rabbits. R848-Toco/HA-Toco and unformulated R848 were injected subcutaneously into opposing rabbit ears of subjects, and local inflammation and systemic TNF-α responses were observed.

New Zealand White rabbits (3-4 kg) were anaesthetized using 5% isoflurane and injected subcutaneously with 2.5 mg of R848 in 250 µl of vehicle into the ipsilateral ear. R848-Toco/HA-Toco was formulated as described above, and the R848 parent compound was formulated in 0.5% polysorbate 80 (w/v) in water. For histopathology, punch biopsies were taken 24 hours post injection, fixed in formalin, and analyzed by a board-certified veterinary pathologist (Kansas State Veterinary Hospital, Topeka, KS, USA). In separate animals, blood samples were taken pre-injection and at 0.5, 1, 2, 5, and 24 h post-injection time points from the contra-lateral ear (marginal vein, 22 ga). Whole blood was centrifuged at 1500×g for 5 min and the serum were collected for cytokine evaluation. All samples and controls were prepared, and serum cytokine levels were measured.

Figure 8A:
FIG. 8A shows local response at the injection site of rabbit ears. The left showed minimum change after injection of free R848, while the right showed swelling and warmth over 7 days post-treatment. Injection points were marked in purple.
Figure 8A:
Figure 8B:
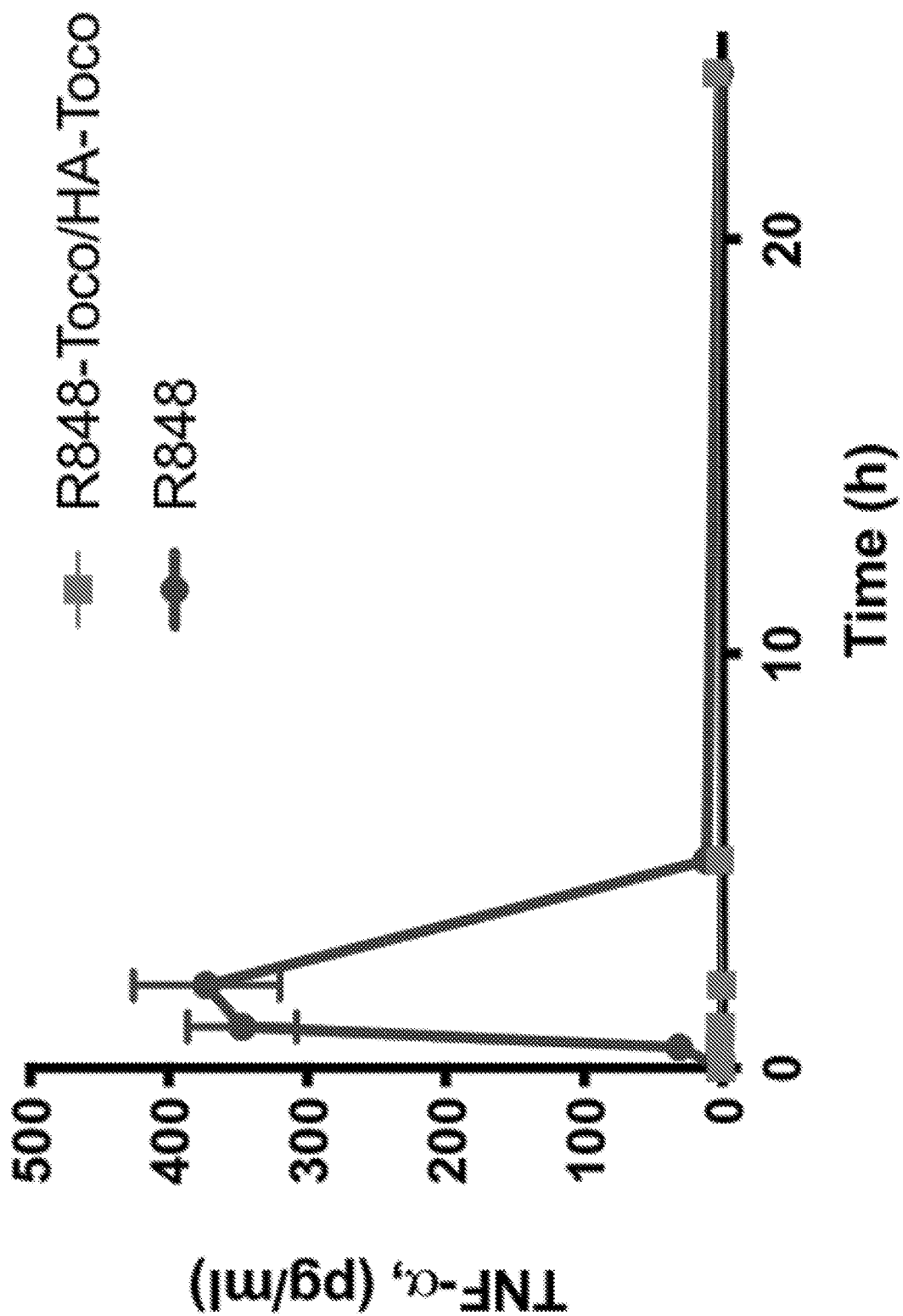
FIG. 8B shows plasma TNF-α levels (n=4). No TNF-α secretion was observed in plasma of rabbits injected with R848-Toco/HA-Toco.

The nano-emulsion produced lasting warmth and swelling at the injection site over several days (FIG. 8A), and histopathological examination of ear tissue confirmed local macrophage infiltration at the injection site, compared to no response in vehicle controls. Systemic TNF-α was not elevated in the plasma, indicating that the response was localized to the injection site during the studied time frame (FIG. 8B). In contrast, free R848 caused no local reaction, based on visual observation and histopathological examination, yet a significant elevation of plasma TNF-α levels occurred within 2 hours post-treatment. Free R848 showed rapid clearance from the injection site and the induction of a systemic response, which was consistent with previous studies as injected R848 dissipated into the blood and induced significant serum TNF-α.[13] Thus, in rabbits R848-Toco/HA-Toco induced a localized immune response at the injection site while minimizing the rapid clearance and subsequent systemic activity, suggesting that the formulation may be applicable for local treatments such as intratumoral injections.

In Vivo Anti-Tumor Efficacy

The anti-tumor efficacy of the R848-Toco nano-emulsion was next evaluated in an immune competent murine allograft model of head and neck cancer. The AT84 cell line was derived from a spontaneous oral squamous cell carcinoma (OSCC) of a C3H mouse and display several key similarities to the human disease including local invasiveness and lung metastases.[18,41] Before studies were performed, the cell line was confirmed to be free of mouse pathogens and other microbial contaminants that could induce an immunological response to the tumor cell injections. C3H mice with OSCC allografts were treated with R848-Toco/HA-Toco or the vehicle HA-Toco. Wildtype C3H mice (Charles River Strain 025, 6-8 weeks old) were used for in vivo tumor studies. Both male and female mice were used in the studies. Results are presented with both sexes as a single group since no significant differences were found in growth rates or results between sexes. Since unformulated R848 rapidly diffuses from the injection site and has no localized stimulatory effect, it was not suitable for intratumoral injection and thus was not tested in this study.

AT84 cells were derived from a spontaneous squamous cell carcinoma in the oral mucosa of a C3H mouse and were gifted by Aldo Venuti (Regina Elena National Cancer Institute, Rome, Italy). Cells tested negative for interspecies contamination (species: mouse(+), rat(−), human(−), Chinese hamster(−), African green monkey(−); Idexx BioResearch), negative for rodent pathogens (Idexx BioResearch, 21 pathogen IMPACT I PCR profile), and negative for Mycoplasm contamination prior to animal studies (Lonza, MycoAlert test kit). Idexx CellCheck STR (short tandem repeat) profile: MCA-4-2: 20.3, 21.3; MCA-5-5: 15; MCA-6-4: 18, 19; MCA-6-7: 12; MCA-9-2: 15; MCA-12-1: 16; MCA-15-3: 25.3, 26.3; MCA-18-3: 16; MCA-X-1: 26, 27. Cells were cultured in RPMI-1640 media (Gibco) supplemented with 10% FBS (Corning), and 100 U/mL penicillin/ 100 µg/mL streptomycin (HyClone) in a humidified incubator at 37° C. and 5% $CO_2$.

Mice were anesthetized using 5% isoflurane in $O_2$ for 5 min. One million AT84 cells in 50 µL of PBS were injected subcutaneously into the floor of the mouth using an extra oral route to obtain orthotopic allograft tumors.[41] Tumors were palpable by day 4. Under isoflurane anesthesia, 50 µL of R848-Toco/HA-Toco (25 µg on R848 basis) was injected intratumorally on days 4, 5, 11, 12, 18, and 19, which were the first 2 days of 3 consecutive weeks. The vehicle control was 50 µL of HA-Toco (16.7 mg/mL) and was injected on the same schedule. Tumor size was calculated as tumor volume $(mm^3)=0.52\times(width)^2\times length$, where length is the longer of two perpendicular dimensions.

Figure 9:
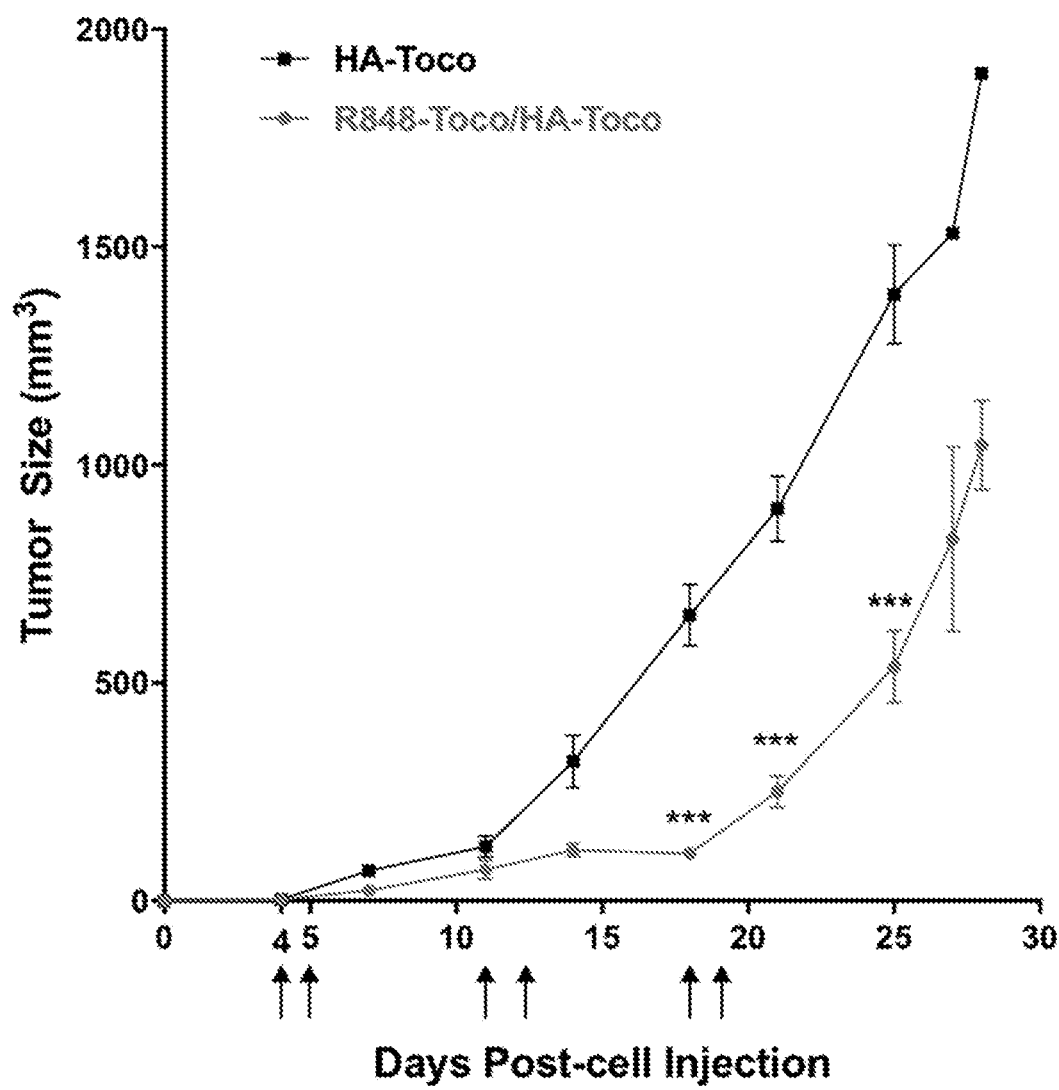
FIG. 9 shows that R848-Toco shows efficacy in oral squamous cell carcinoma (OSCC) allografts. Mice with OSCC allograft tumors were treated on days 4, 5, 11, 12, 18, and 19 (injection points marked by arrows). R848-Toco/HA-Toco significantly suppresses tumor growth compared to vehicle (two-way ANOVA: p<0.001 for treatment, time, and interaction; Bonferroni posttest *** p<0.001; n=6-8).

The R848-Toco/HA-Toco significantly decreased the tumor growth compared to HA-Toco vehicle over the selected time course of 6 treatments (FIG. 9). Tumor growth recovered after the treatment ended, indicating that either an increased dose or treatment time may be required to achieve a more durable response. Alternatively, R848-Toco may be combined with other immunotherapies that prevent immunosuppression. For example, the TLR9 agonist CpG injected intratumorally has minimum activity as a monotherapy, but demonstrated a significant enhancement of survival time in clinical trials for metastatic melanoma.[37]

Excised tumors were then imaged to determine if R848-Toco/HA-Toco induced immune cell infiltrations as found in the normal rabbit studies. General immune cell immunohistochemistry of the tumors was performed.

When tumors reached 200-400 $mm^3$ (about 2 weeks post-cell injection), R848-Toco/HA-Toco (25 µg on R848 basis) in 50 µL volume was injected intratumorally. After 24 h, tumors were dissected and embedded in OCT medium (Fisher Scientific), followed by storage at −80° C. Tumors were sectioned (10 µm) with a cryotome. Sections were fixed for 2×10 min with acetone and washed with PBS. Primary antibodies were diluted to 5 µg/mL in blocking buffer (5% goat serum in PBS) and incubated overnight at 4° C. Antibodies used were Alexa Fluor® 488 anti-CD8a, Alexa Fluor® 594 anti-CD11b, and Alexa Fluor® 647 anti-CD11c (BioLegend). After antibody staining, sections were stained with DAPI (0.5 µg/mL in PBS; Invitrogen) for 10 minutes, mounted in SouthernBiotech™ Fluoromount-G™ Slide Mounting Medium and stored in the dark at 4° C. Images were acquired using an Olympus IX-81 inverted epifluorescence microscope at 10× magnification, and images were captured with a Hamamatsu EM-CDD Digital Camera. The entire tumor section was imaged. Many 10× images were montaged together using SlideBook 6 to view the whole section.

Figure 10:
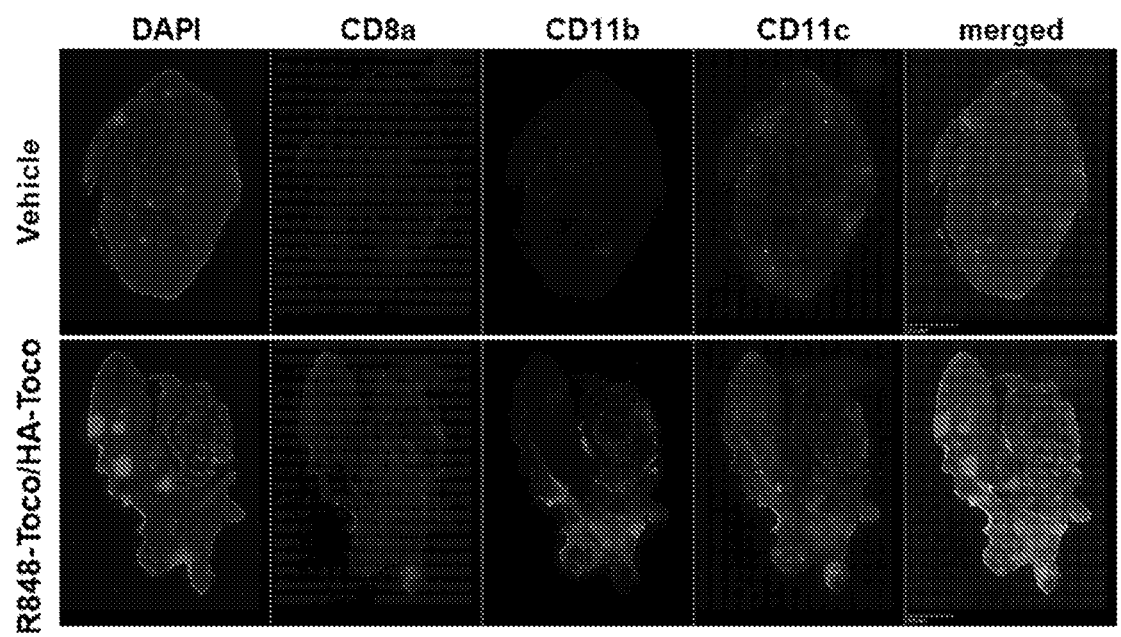
FIG. 10 shows that R848-Toco recruits immune cells to tumors. Immune cell markers, CD8a, CD11d, and CD11c, are increased in AT84 tumors after 6 treatments with intratumoral Res-Toco/HA-Toco (25 µg on R848 basis). Representative images are shown from 3 independent experiments using an Olympus IX-81 inverted epifluorescence microscope. The entire tumor section is viewed as a montage of 10× magnification images. Scale bar is 2.5 mm.

48 hours after final injection, tumors were removed, sectioned, and stained with fluorescently labeled antibodies of selected immunological markers (CD8a, CD11c, CD11b). R848-Toco/HA-Toco generated an increase in marker staining in allografts (FIG. 10). CD8a is marker for activated cytotoxic T cells, CD11b is a marker for macrophages, and CD11c is primarily a marker for DCs, but may also be expressed on T cells and macrophages, all critical immune cells involved in an anti-cancer immune response.[2,28] Macrophages are more associated with a T helper cell response, while DCs activate cytotoxic CD8a+ T cells. It is important to only compare antibody staining between treatments and not between different antibodies, as different antibodies have different affinities to their respective antigens. Therefore, these results are qualitative only, not quantitative. RNA sequencing studies are currently underway to make more quantitative comparisons. The recruitment of immune cells after R848-Toco/HA-Toco injection suggests immune activation at the injection site.

Pilot Canine Trial

Mast cell cancer is one of the most common neoplasms in canines. Treatment typically includes surgical removal of the tumor, but it has a high propensity for recurrence even if clean margins are achieved at the surgery. The only FDA-approved veterinary medication for the treatment of mast cell tumors is the kinase inhibitor toceranib phosphate (Palladia®). In a double-blind, randomized clinical study of toceranib phosphate in mast cell tumors, the response rate was 37.2% in 86 canine patients (7 complete response and 25 partial response) versus 7.9% (5 partial response) in 63 placebo-treated dogs.[10]

In this study a total of 6 subjects were treated that include two Labrador Retrievers (8 and 12.5-year old), an Italian Greyhound (13-year old), two American Staffordshire Terriers (7 and 9-year old), and a Boxer (7-year old). The diagnostics were obtained via either histopathology or cytology. The patients were treated at 3-week intervals with 2 to 7 injections of R848-Toco/HA-Toco at a dose level ranging from 0.07 to 1.70 mg on R848 basis. Complete blood counts and clinical chemistry were performed prior to the first treatment and 1-week post each subsequent injection.

Three of six had partial response (50%); one of six had complete response (17%); another two had stable disease (17%) and progressive disease (17%), respectively.

Figure 11A:
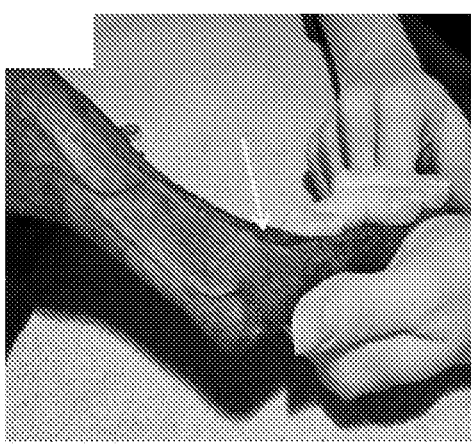
FIG. 11A shows the location of the tumor in the lateral right hock, indicated by the yellow arrow.
Figure 11B:
FIG. 11B shows the area prior to the first injection.
Figure 11C:
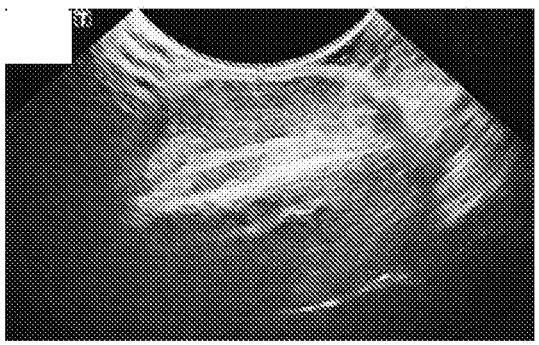
FIG. 11C shows the area prior to the second injection.
Figure 11D:
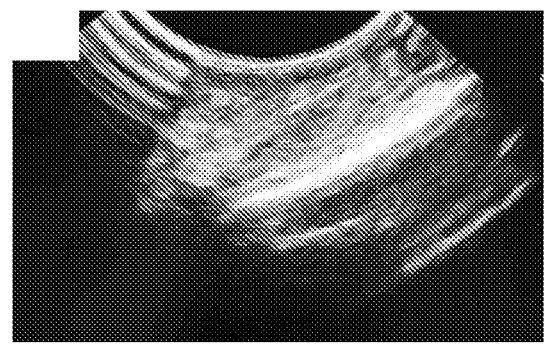
FIG. 11D shows the area 3 weeks after the second injection.

In the complete responder, a firm tumor was located over the lateral right hock of the dog (FIG. 11A). The mass was inoperable without amputation due to its location. The dog had previously been treated with toceranib phosphate but discontinued due to side effects and lack of effect. The dog received a total of 2 nano-emulsion injections intralesionally at a dose of 0.34 mg on a R848 basis per injection 3 weeks apart. The administration of the medication was performed via ultrasound guidance. The tumor measured 0.49 cm by 1.58 cm prior to the first injection (FIG. 11B). Three weeks later, the subject was rechecked, and the tumor size of the mass was about the same as prior to the first injection (FIG. 11C). The second treatment was administered intratumorally to the center of the mass tumor. Three weeks after the second treatment, the dog was presented for a physical exam, during which no gross evidence of the tumor was found, and ultrasound of the right hock area revealed no tumor (FIG. 11D). All prestudies and post treatment blood work results were unremarkable.

The three partial responders demonstrated similar remissions and clinical behaviors. These findings will be discussed as a group. At the beginning of the study, all three subjects have had tumors smaller than 2.5 cm in the longest dimension. All three subjects responded after the first treatment indicating tumor shrinkage in at least one dimension. For example, on the day of the second treatments (approximately 3 weeks after the first treatment), the percent reduction in the length of the masses was 57% (from 0.7 cm to 0.3 cm), 50% (from 2.4 cm to 1.2 cm) and 25% (from 1.6 cm to 1.2 cm), respectively, compared to the dimensions on the day of the first treatment. Complete blood counts with differentials and clinical chemistry tests (liver enzymes, BUN/creatinine etc.) revealed no significant differences between pre-study and post-treatment results.

The other two subjects have either stable or progressive disease with large (longer than 9.0 cm in the longest dimension) or multiple tumor burdens (a total of 7 individual, medium to large sized masses). Unfortunately, the subject with 7 tumors did not respond to the therapy after completing all four injections. However, it is to be noted that the stable disease subject only received the second injection. A partial remission is still possible after additional treatments.

Example 4: Retention of Coversin by HA-Toco

To show that Hyaluronan-Toco could form a subcutaneous depot for a variety of compounds including both small molecules such as the TLR7/8-tocopherol and for large molecules such as the ca. 17 kDa protein therapeutic Coversin, injections of the depots were performed in mice followed by fluorescent in vivo imaging.

Coversin-AlexaFluor647 dye conjugates (Cov647) were made by reacting Coversin (16.7 kDa) to NHS-AlexaFluor647 (1.25 kDa) at a 1:5 (mol:mol) ratio in 0.1 M NaHCO$_3$, pH 8.8 for 2 hours at 25° C. Unreacted dye was removed by gel permeation chromatography using a Sephadex G-25 PD10 column with subsequent exhaustive dialysis against a 10 kDa MWCO membrane with three, 3.5 L PBS bath changes over 48 hours.

Purified Cov647 (0.25 mg/ml, protein basis) was added to lyophilized 33 kDa Hyaluronic acid-tocopherol, 10% disacc. subs. (33kHAt10) to a final concentration of 10 mg/ml 33kHAt10 and dissolved overnight at 25° C. Once dissolved, to further reduce fluorescent intensity the sample was diluted 8:1 (vol:vol) using the same protein:polymer mixture, but with unmodified Coversin. PBS formulated Cov647 controls were prepared and diluted as above, but without 33kHAt10.

10 µl of Cov647/33kHAt10 or Cov647/PBS were injected to the hind footpad of three female BALB/c mice. Hind limb hair was removed to limit autofluorescence and areas imaged using a CRi Maestro In Vivo Imaging System with constant 1000 ms exposure, excitation filter (615 nm to 665 nm) and emission filter (645 nm longpass).

Unscaled 800 nm fluorescent emission images were uniformly background subtracted using ImageJ and overlaid with bright field images. The PBS control images showed that after 24 hours substantially all of the Cov647 had left the injection site (FIG. 12C). However, the 33KHAt10 substantially retained the Cov647 after 24 hours (FIG. 12D).

Figure 13:
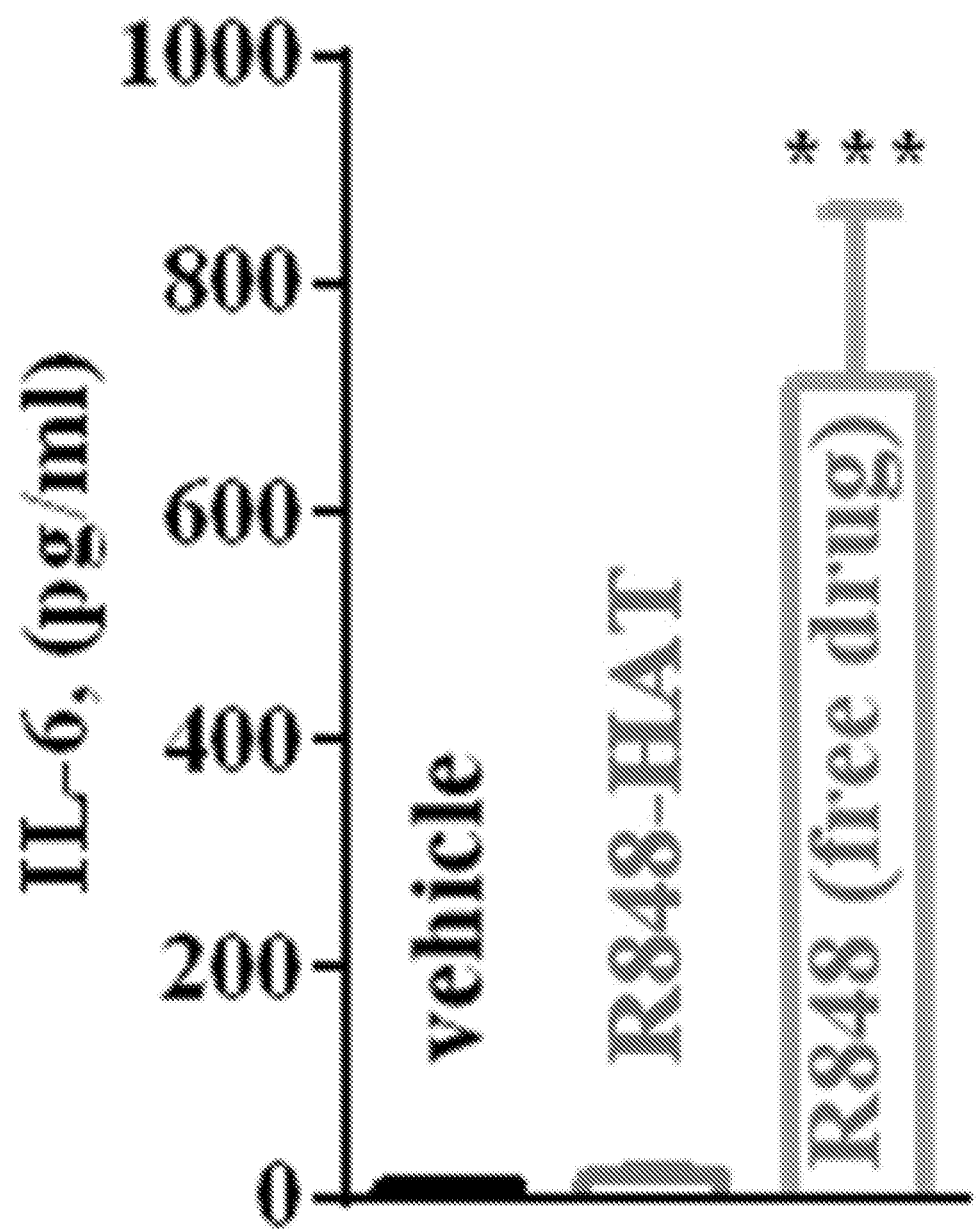
FIG. 13 illustrates the systemic release of IL6 (a proinflammatory cytokine) when R848 in DMSO is administered subcutaneously to a mouse, whereas subcutaneous depot injection of R848-Toco dispersed in HA-tocopherol ("R848-HAT") did not elicit release of systemic cytokines.

FIG. 13 illustrates the systemic release of IL6 (a proinflammatory cytokine) when R848 in DMSO is administered subcutaneously to a mouse, whereas subcutaneous depot injection of R848-Toco dispersed in HA-tocopherol ("R848-HAT") did not elicit release of systemic cytokines.

Example 5: R848-Toco and Local Inflammation in Rabbit Ears

Solutions 1–4 were prepared as follows:
1. R848-Toco/TPGS (TPGS=tocopheryl polyethylene glycol succinate): R848-Toco (10 mg) and TPGS (90 mg) were dissolved in dichloromethane (2 mL), and the mixture was slowly evaporated at 35° C. to form a thin film of dry solid, which was then rehydrated in water for injection (1 mL).
2. R848-Toco/EtOH/SAIB (SAIB=Sucrose acetate isobutyrate): A R848-Toco solution in ethanol (166.7 mg/mL, 0.06 mL) was added dropwise to the agitating solution of SAIB (w/15% EtOH, 0.94 mL), and the mixture was stirred at 37° C. for 16 h.

3. R848-Toco/DMSO/SAIB: An R848-Toco solution in DMSO (166.7 mg/mL, 0.06 mL) was added dropwise to the agitating solution of SAIB (w/10% DMSO, 0.94 mL), and the mixture was stirred at 37° C. for 16 h.
4. R848/0.5% Tween: R848 (10 mg) was suspended in 0.5% Tween 80 aqueous solution, and the mixture was agitated at 37° C. for 16 h, followed by filtration through 0.22 um filter.

New Zealand White rabbits (3-4 kg) were anaesthetized using 5% isoflurane and injected subcutaneously (s.c.) in the dorsal side of the ear with each formulation, which contained 2.5 mg of R848 in 250 µl volume. Injection site is marked in purple and was monitored for 7 days. The results for each injected solution 1-4 are as follows:

1. R848-Toco/TPGS: Much swelling at 4 hours through 72 hours. Moderate swelling 4 days. No swelling 7 days.
2. R848-Toco/EtOH/SAIB: Moderate swelling at 24 hours through 72 hours. No swelling 4-7 days
3. R848-Toco/DMSO/SAIB: No swelling through 7 days.
4. R848/0.5% Tween: Mild swelling at 1-2 hours; No swelling through 7 days.

REFERENCES (1) A. Allahham, P. Stewart, J. Marriott, D. E. Mainwaring, Flow and injection characteristics of pharmaceutical parenteral formulations using a micro-capillary rheometer, *Int. J. Pharm.* 270 (2004) 139-148. doi:10.1016/J.IJPHARM.2003.10.008.

(2) A. M. Wolf, D. Wolf, M. Steurer, G. Gastl, E. Gunsilius, B. Grubeck-Loebenstein, Increase of regulatory T cells in the peripheral blood of cancer patients., *Clin. Cancer Res.* 9 (2003) 606-12. http://www.ncbi.nlm.nih.gov/pubmed/12576425 (accessed Jan. 12, 2019).

(3) A. Z. Dudek, C. Yunis, L. I. Harrison, S. Kumar, R. Hawkinson, S. Cooley, J. P. Vasilakos, K. S. Gorski, J. S. Miller, First in human phase I trial of 852A, a novel systemic toll-like receptor 7 agonist, to activate innate immune responses in patients with advanced cancer, *Clin. Cancer Res.* 13 (2007) 7119-7125. doi:10.1158/1078-0432.CCR-07-1443.

(4) Adam Littke, *,†; Maxime Soumeillant, *‡; Robert F. Kaltenbach III, §; Robert J. Cherney, §; Christine M. Tarby, § and; Kiau ∛, S. Mild and General Methods for the Palladium-Catalyzed Cyanation of Aryl and Heteroaryl Chlorides. *Org. Lett.* 2007, 9, 9, 1711-1714.

(5) Akira, S.; Takeda, K.; Kaisho, T. Toll-like Receptors: Critical Proteins Linking Innate and Acquired Immunity. *Nat. Immunol.* 2001, 2 (8), 675-680.

(6) Bonaccorsi, I.; Pezzino, G.; Morandi, B.; Ferlazzo, G. Novel Perspectives on Dendritic Cell-Based Immunotherapy of Cancer. *Immunol. Lett.* 2013, 155 (1-2), 6-10.

(7) Bott, R. *Janeways Immunobiology;* 2014.

(8) C. Hotz, M. Treinies, I. Mottas, L. C. Rötzer, A. Oberson, L. Spagnuolo, M. Perdicchio, T. Spinetti, T. Herbst, C. Bourquin, Reprogramming of TLR7 signaling enhances antitumor NK and cytotoxic T cell responses, *Oncoimmunology.* 5 (2016) e1232219. doi:10.1080/2162402X.2016.1232219.

(9) C. Kuehl, T. Zhang, L. M. Kaminskas, C. J. H. Porter, N. M. Davies, L. Forrest, C. Berkland, Hyaluronic Acid Molecular Weight Determines Lung Clearance and Biodistribution after Instillation, (2016). doi:10.1021/acs.molpharmaceut.6b00069.

(10) C. A. London, P. B. Malpas, S. L. Wood-Follis, J. F. Boucher, A. W. Rusk, M. P. Rosenberg, C. J. Henry, K. L. Mitchener, M. K. Klein, J. G. Hintermeister, P. J. Bergman, G. C. Couto, G. N. Mauldin, G. M. Michels, Multi-center, Placebo-controlled, Double-blind, Randomized Study of Oral Toceranib Phosphate (SU11654), a Receptor Tyrosine Kinase Inhibitor, for the Treatment of Dogs with Recurrent (Either Local or Distant) Mast Cell Tumor Following Surgical Excision, *Clin. Cancer Res.* 15 (2009) 3856 LP-3865. doi:10.1158/1078-0432.CCR-08-1860.

(11) C. B. Fox, M. T. Orr, N. Van Hoeven, S. C. Parker, T. J. T. Mikasa, T. Phan, E. A. Beebe, G. I. Nana, S. W. Joshi, M. A. Tomai, J. Elvecrog, T. R. Fouts, S. G. Reed, Adsorption of a synthetic TLR7/8 ligand to aluminum oxyhydroxide for enhanced vaccine adjuvant activity: A formulation approach, *J. Control. Release.* 244 (2016) 98-107. doi:10.1016/j.jconrel.2016.11.011.

(12) C. M. Perry, H. M. Lamb, Topical Imiquimod, Drugs. 58 (1999) 375-390. doi:10.2165/00003495-199958020-00017.

(13) D. Smirnov, J. J. Schmidt, J. T. Capecchi, P. D. Wightman, Vaccine adjuvant activity of 3m-052: An imidazoquinoline designed for local activity without systemic cytokine induction, Vaccine. 29 (2011) 5434-5442. doi:10.1016/j.vaccine.2011.05.061.

(14) E. G. MacEwen, Spontaneous tumors in dogs and cats: Models for the study of cancer biology and treatment, *Cancer Metastasis Rev.* 9 (1990) 125-136. doi:10.1007/BF00046339.

(15) E. J. Oh, K. Park, K. S. Kim, J. Kim, J. A. Yang, J. H. Kong, M. Y. Lee, A. S. Hoffman, S. K. Hahn, Target specific and long-acting delivery of protein, peptide, and nucleotide therapeutics using hyaluronic acid derivatives, *J. Control. Release.* 141 (2010) 2-12. doi:10.1016/j.jconrel.2009.09.010.

(16) E. L. J. M. Smits, N. Cools, E. Lion, K. Van Camp, P. Ponsaerts, Z. N. Berneman, V. F. I. Van Tendeloo, The Toll-like receptor 7/8 agonist resiquimod greatly increases the immunostimulatory capacity of human acute myeloid leukemia cells, *Cancer Immunol. Immunother.* 59 (2010) 35-46. doi:10.1007/s00262-009-0721-8.

(17) European Medicines Agency, Orphan designation EU/3/16/1653, (2016). https://www.ema.europa.eu/en/medicines/human/orphan-designations/eu3161653.

(18) F. Paolini, S. Massa, I. Manni, R. Franconi, A. Venuti, Immunotherapy in new preclinical models of HPV-associated oral cancers., *Hum. Vaccin. Immunother.* 9 (2013) 534-43. doi:10.4161/HV.23232.

(19) Gerster, J. F.; Lindstrom, K. J.; Miller, R. L.; Tomai, M. a; Birmachu, W.; Bomersine, S. N.; Gibson, S. J.; Imbertson, L. M.; Jacobson, J. R.; Knafla, R. T.; Maye, P. V; Nikolaides, N.; Oneyemi, F. Y.; Parkhurst, G. J.; Pecore, S. E.; Reiter, M. J.; Scribner, L. S.; Testerman, T. L.; Thompson, N. J.; Wagner, T. L.; Weeks, C. E.; Andre, J.-D.; Lagain, D.; Bastard, Y.; Lupu, M. Synthesis and Structure-Activity-Relationships of 1H-Imidazo[4,5-c] Quinolines That Induce Interferon Production. *J. Med. Chem.* 2005, 48 (10), 3481-3491.

(20) Gerster, John F.; Lindstrom, Kyle J.; Marszalek, Gregory J.; Merrill, Bryon A.; Mickelson, John W.; Rice, M. J. Preparation of Oxazolo, Thiazolo and Selenazolo [4,5-c]Quinolin-4-Amines as Immunomodulators and for Inducing Cytokine Biosynthesis. WO 2000006577, 2000.

(21) Goodman, M. G. A New Approach to Vaccine Adjuvants; Springer, Boston, MA, 1995; pp 581-609.
(22) H. Kumar, T. Kawai, S. Akira, Toll-like receptors and innate immunity, *Biochem. Biophys. Res. Commun.* 388 (2009) 621-625. doi:10.1016/J.BBRC.2009.08.062.
(23) Heil, F. Species-Specific Recognition of Single-Stranded RNA via Toll-like Receptor 7 and 8. *Science* (80-.). 2004, 303 (5663), 1526-1529.
(24) Hornung, V.; Rothenfusser, S.; Britsch, S.; Krug, A.; Jahrsdorfer, B.; Giese, T.; Endres, S.; Hartmann, G. Quantitative Expression of Toll-like Receptor 1-10 MRNA in Cellular Subsets of Human Peripheral Blood Mononuclear Cells and Sensitivity to CpG Oligodeoxynucleotides. *J. Immunol.* 2002, 168 (9), 4531-4537.
(25) Howbert, J. J.; Dietsch, G.; Hershberg, R.; Burgess, L. E.; Lyssikatos, J. P.; Newhouse, B.; Yang, H. W. Substituted Benzoazepines as Toll-Like Receptor Modulators. WO2011022508A2, 2011.
(26) Invivogen, HEK-Blue TLR7 cells, (2018). https://www.invivogen.com/hek-blue-tlr7.
(27) Iwasaki, A.; Medzhitov, R. Regulation of Adaptive Immunity by the Innate Immune System. *Science* 2010, 327 (5963), 291-295.
(28) J. Qualai, L.-X. Li, J. Cantero, A. Tarrats, M. A. Fernandez, L. Sumoy, A. Rodolosse, S. J. McSorley, M. Genescà, Expression of CD11c Is Associated with Unconventional Activated T Cell Subsets with High Migratory Potential, *PLoS One.* 11 (2016) e0154253. doi:10.1371/journal.pone.0154253.
(29) K. Bouchemal, S. Briançon, E. Perrier, H. Fessi, Nano-emulsion formulation using spontaneous emulsification: solvent, oil and surfactant optimisation, *Int. J. Pharm.* 280 (2004) 241-251. doi:10.1016/J.IJPHARM.2004.05.016.
(30) K. Dabbagh, D. B. Lewis, Toll-like receptors and T-helper-1/T-helper-2 responses, *Curr. Opin. Infect. Dis.* (2003) 199-204. doi:10.1097/01.qco.0000073767.11390.47.
(31) K. N. Prasad, B. Kumar, X.-D. Yan, A. J. Hanson, W. C. Cole, α-Tocopheryl Succinate, the Most Effective Form of Vitamin E for Adjuvant Cancer Treatment: A Review, *J. Am. Coll. Nutr.* 22 (2003) 108-117. doi:10.1080/07315724.2003.10719283.
(32) K. R. Richter, A. N. Nasr, A. M. Mexas, Cytokine Concentrations Measured by Multiplex Assays in Canine Peripheral Blood Samples, *Vet. Pathol.* 55 (2018) 53-67. doi:10.1177/0300985817725388.
(33) K. Y. Choi, K. H. Min, J. H. Na, K. Choi, K. Kim, J. H. Park, I. C. Kwon, S. Y. Jeong, Self-assembled hyaluronic acid nanoparticles as a potential drug carrier for cancer therapy: synthesis, characterization, and in vivo biodistribution, *J. Mater. Chem.* 19 (2009) 4102. doi:10.1039/b900456d.
(34) Kawai, T.; Akira, S. The Role of Pattern-Recognition Receptors in Innate Immunity: Update on Toll-like Receptors. *Nat. Immunol.* 2010, 11 (5), 373-384.
(35) Kumagai, Y.; Takeuchi, O.; Akira, S. Pathogen Recognition by Innate *Receptors. J. Infect. Chemother.* 2008, 14 (2), 86-92.
(36) Larson, P.; Kucaba, T. A.; Xiong, Z.; Olin, M.; Griffith, T. S.; Ferguson, D. M. Design and Synthesis of N1-Modified Imidazoquinoline Agonists for Selective Activation of Toll-like Receptors 7 and 8. *ACS Med. Chem. Lett.* 2017, 8 (11), 1148-1152.
(37) M. Pashenkov, G. Goëss, C. Wagner, M. Hörmann, T. Jandl, A. Moser, C. M. Britten, J. Smolle, S. Koller, C. Mauch, I. Tantcheva-Poor, S. Grabbe, C. Loquai, S. Esser, T. Franckson, A. Schneeberger, C. Haarmann, A. M. Krieg, G. Stingl, S. N. Wagner, Phase II Trial of a Toll-Like Receptor 9-Activating Oligonucleotide in Patients With Metastatic Melanoma, *J. Clin. Oncol.* 24 (2006) 5716-5724. doi:10.1200/JCO.2006.07.9129.
(38) M. Singh, H. Khong, Z. Dai, X.-F. Huang, J. A. Wargo, Z. A. Cooper, J. P. Vasilakos, P. Hwu, W. W. Overwijk, Effective Innate and Adaptive Antimelanoma Immunity through Localized TLR7/8 Activation, *J. Immunol.* 193 (2014) 4722-4731. doi:10.4049/JIMMUNOL.1401160.
(39) M. A. Tomai, J. P. Vasilakos, TLR7/8 Agonists as Vaccine Adjuvants, in: November Immune Potentiators Deliv. Technol. next Gener. *Vaccines,* 2013: pp. 3-18.
(40) M. G. Netea, J. W. M. Van Der Meer, R. P. Sutmuller, G. J. Adema, B.-J. Kullberg, From the Th1/Th2 Paradigm towards a Toll-Like Receptor/T-Helper Bias, *Antimicrob. Agents Chemother.* 49 (2005) 3991-3996. doi:10.1128/AAC.49.10.3991-3996.2005.
(41) M. P. Hier, M. J. Black, G. Shenouda, N. Sadeghi, S. E. Karp, A murine model for the immunotherapy of head and neck squamous cell carcinoma, *Laryngoscope.* 105 (1995) 1077-1080. doi:10.1288/00005537-199510000-00013.
(42) Miller, R.; Gerster, J.; Owens, M.; Slade, H.; Tomai, M. Review Article Imiquimod Applied Topically: A Novel Immune Response Modifier and New Class of Drug. *Int. J. Immunopharmacol.* 1999, 21 (1), 1-14.
(43) Mogensen, M.; Nürnberg, B. M.; Forman, J. L.; Thomsen, J. B.; Thrane, L.; Jemec, G. B. E. In Vivo Thickness Measurement of Basal Cell Carcinoma and Actinic Keratosis with Optical Coherence Tomography and 20-MHz Ultrasound. *Br. J. Dermatol.* 2009, 160 (5), 1026-1033.
(44) N. Duhem, F. Danhier, V. Préat, Vitamin E-based nanomedicines for anti-cancer drug delivery, *J. Control. Release.* 182 (2014) 33-44. doi:10.1016/J.JCONREL.2014.03.009.
(45) N. M. Shukla, S. S. Malladi, C. A. Mutz, R. Balakrishna, S. A. David, Structure-Activity Relationships in Human Toll-Like Receptor 7-Active Imidazoquinoline Analogues, *J. Med. Chem.* 53 (2010) 4450-4465. doi:10.1021/jm100358c.
(46) P. J. Felsburg, Overview of immune system development in the dog: comparison with humans, *Hum. Exp. Toxicol.* 21 (2002) 487-492. doi:10.1191/0960327102ht286oa.
(47) P. O. Ilyinskii, C. J. Roy, C. P. O'Neil, E. A. Browning, L. A. Pittet, D. H. Altreuter, F. Alexis, E. Tonti, J. Shi, P. A. Basto, M. Iannacone, A. F. Radovic-Moreno, R. S. Langer, O. C. Farokhzad, U. H. von Andrian, L. P. M. M. Johnston, T. K. Kishimoto, C. P. O'Neil, E. A. Browning, L. A. Pittet, D. H. Altreuter, F. Alexis, E. Tonti, J. Shi, P. A. Basto, M. Iannacone, A. F. Radovic-Moreno, R. S. Langer, O. C. Farokhzad, U. H. von Andrian, L. P. M. M. Johnston, T. K. Kishimoto, Adjuvant-carrying synthetic vaccine particles augment the immune response to encapsulated antigen and exhibit strong local immune activation without inducing systemic cytokine release, Vaccine. 32 (2014) 2882-2895. doi:10.1016/j.vaccine.2014.02.027.
(48) P.-Y. Bochud, M. Bochud, A. Telenti, T. Calandra, Innate immunogenetics: a tool for exploring new frontiers of host defense., *Lancet. Infect. Dis.* 7 (2007) 531-42. doi:10.1016/S1473-3099(07)70185-8.
(49) Phase I/II Trial of a Long Peptide Vaccine (LPV7) Plus TLR Agonists—Full Text View—ClinicalTrials.gov https://clinicaltrials.gov/ct2/show/NCT02126579?term=resiqu-imod&phase=012&draw=3&rank=14 (accessed Aug. 15, 2018).
(50) Q. Fu, Y. Wang, Y. Ma, D. Zhang, J. K. Fallon, X. Yang, D. Liu, Z. He, F. Liu, Programmed Hydrolysis in Designing Paclitaxel Prodrug for Nanocarrier Assembly, *Sci. Rep.* 5 (2015) 12023. doi:10.1038/srep12023.
(51) Rook, A. H.; Gelfand, J. M.; Wysocka, M.; Troxel, A. B.; Benoit, B.; Surber, C.; Elenitsas, R.; Buchanan, M. A.; Leahy, D. S.; Watanabe, R.; Kirsch, I. R.; Kim, E. J.; Clark, R. A.; Clark, R. A. Topical Resiquimod Can Induce Disease Regression and Enhance T-Cell Effector Functions in Cutaneous T-Cell Lymphoma. *Blood* 2015, 126 (12), 1452-1461.
(52) S. van Aalst, M. A. A. Jansen, I. S. Ludwig, R. van der Zee, W. van Eden, F. Broere, Routing dependent immune responses after experimental R848-adjuvated vaccination, *Vaccine.* 36 (2018) 1405-1413. doi:10.1016/J.VACCINE.2018.01.077.
(53) Schiaffo, C.; Shi, C.; Xiong, Z.; Olin, M.; Ohlfest, J.; Aldrich, C.; Ferguson, D. Structure Activity Relationship Analysis of Imidazoquinolines with Toll-Like Receptor 7 and 8 Selectivity and Enhanced Cytokine Induction. *J. Med. Chem.* 2014.
(54) Schiffman, M.; Wacholder, S. Success of HPV Vaccination Is Now a Matter of Coverage. *Lancet. Oncol.* 2012, 13 (1), 10-12.
(55) Shi, C.; Xiong, Z.; Chittepu, P.; Aldrich, C. C.; Ohlfest, J. R.; Ferguson, D. M. Discovery of Imidazoquinolines with Toll-Like Receptor 7/8 Independent Cytokine Induction. *ACS Med. Chem. Lett.* 2012, 3 (6), 501-504.
(56) Shukla, N. M.; Kimbrell, M. R.; Malladi, S. S.; David, S. A. Regioisomerism-Dependent TLR7 Agonism and Antagonism in an Imidazoquinoline. *Bioorg. Med. Chem. Lett.* 2009, 19 (8), 2211-2214.
(57) Shukla, N. M.; Malladi, S. S.; Mutz, C. A.; Balakrishna, R.; David, S. A. Structure-Activity Relationships in Human Toll-like Receptor 7-Active Imidazoquinoline Analogues. *J. Med. Chem.* 2010, 53 (11), 4450-4465.
(58) T. Kawai, S. Akira, The role of pattern-recognition receptors in innate immunity: update on Toll-like receptors, *Nat. Immunol.* 11 (2010) 373-384. doi:10.1038/ni.1863.
(59) T. Nakamura, M. Goto, A. Matsumoto, I. Tanaka, Inhibition of NF-κB transcriptional activity by α-tocopheryl succinate, *BioFactors.* 7 (1998) 21-30. doi:10.1002/biof.5520070104.
(60) Tanji, H.; Ohto, U.; Shibata, T.; Miyake, K.; Shimizu, T. Structural Reorganization of The. *Science* (80-.). 2013, 1426 (March), 2013.
(61) Tumor and Vaccine Site With a Toll Like Receptor (TLR) Agonist—Full Text View—ClinicalTrials.gov https://clinicaltrials.gov/ct2/show/NCT00960752?term=resiquimod&phase=012&rank=10 (accessed Aug. 15, 2018).
(62) V. Delplace, P. Couvreur, J. Nicolas, Recent trends in the design of anticancer polymer prodrug nanocarriers, *Polym. Chem.* 5 (2014) 1529-1544. doi:10.1039/C3PY01384G.
(63) Wagner, T. L.; Ahonen, C. L.; Couture, A. M.; Gibson, S. J.; Miller, R. L.; Smith, R. M.; Reiter, M. J.; Vasilakos, J. P.; Tomai, M. A. Modulation of TH1 and TH2 Cytokine Production with the Immune Response Modifiers, R-848 and Imiquimod. *Cell. Immunol.* 1999, 191 (1), 10-19.
(64) Wu, T. Y. H.; Li, Y.; Cortez, A.; Zou, Y.; Mishra, P.; Zhang, X.; Skibinski, D.; Singh, M.; Valiante, N. Compounds and Compositions as Tlr Activity Modulators. 2009.
(65) Y. Singh, M. Palombo, P. Sinko, Recent Trends in Targeted Anticancer Prodrug and Conjugate Design, *Curr. Med. Chem.* 15 (2008) 1802-1826. doi:10.2174/092986708785132997.
(66) Y. J. Suzuki, L. Packer, Inhibition of NF-κB Activation by Vitamin E Derivatives, *Biochem. Biophys. Res. Commun.* 193 (1993) 277-283. doi:10.1006/bbrc.1993.1620.
(67) Zhang, Z.; Ohto, U.; Shibata, T.; Krayukhina, E.; Taoka, M.; Yamauchi, Y.; Tanji, H.; Isobe, T.; Uchiyama, S.; Miyake, K.; Shimizu, T. Structural Analysis Reveals That Toll-like Receptor 7 Is a Dual Receptor for Guanosine and Single-Stranded RNA. *Immunity* 2016, 45 (4), 737-748.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I

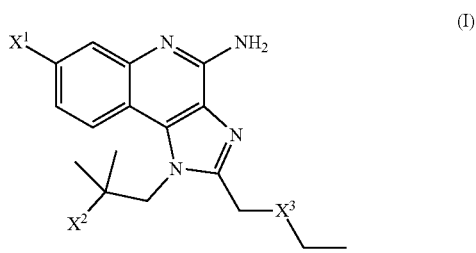

or a pharmaceutically acceptable salt thereof, wherein $X^1$ is H, halo, hydroxy, amino, cyano, trifluoromethyl, thiol, alkylthio, sulfoxide, sulfone, nitro, pentafluorosulfanyl, carboxylate, amide, ester, $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, aryloyloxy,

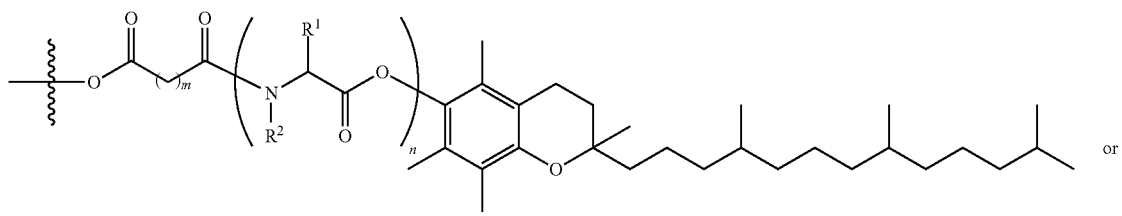

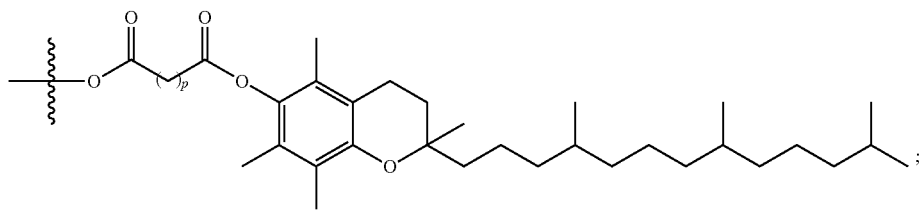

$X^2$ is H, hydroxyl,

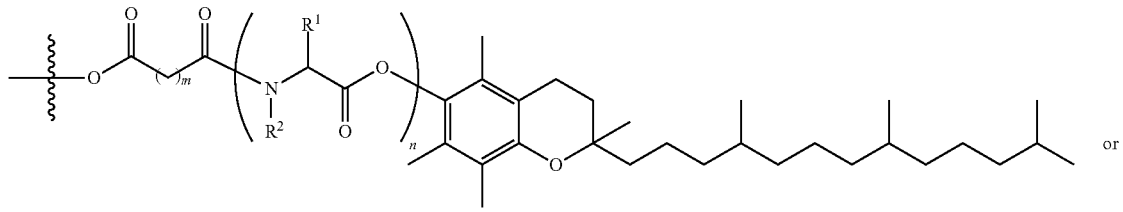

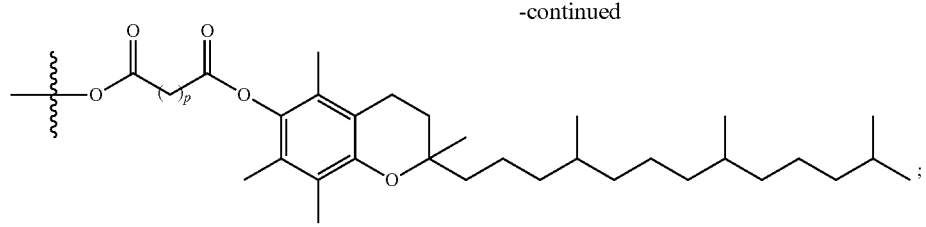
m is 1, 2, 3, 4, 5, 6, 7, or 8;
n is 1, 2, or 3;
p is 1, 2, 3, 4, 5, 6, 7, or 8; and
$X^3$ is $CH_2$ or O;
provided that at least one of $X^1$ and $X^2$ is not
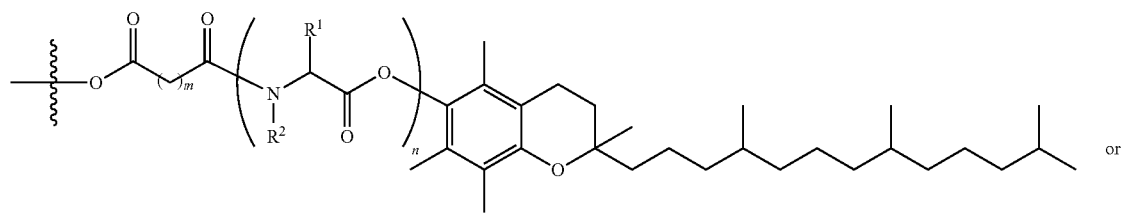 or
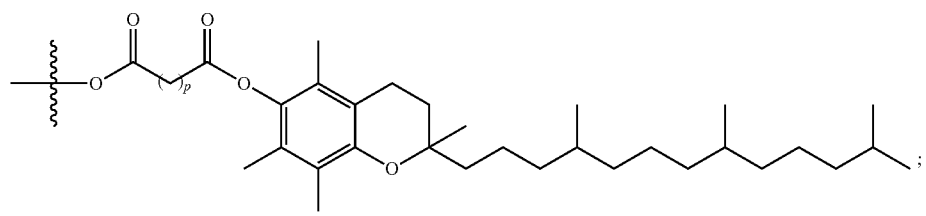
and
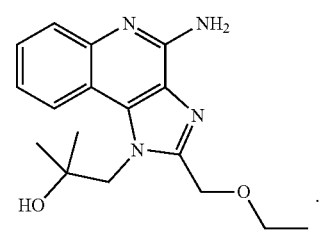 [SMILES: CCOCc1nc2c(N)nc3ccccc3c2n1CC(C)(C)O]
wherein the compound of Formula I is not
B. The compound of Paragraph A, wherein
$X^1$ is H, halo, hydroxy, amino, cyano, thiol, alkylthio, C1-C6 alkyl, C1-C6 alkoxy, aryloxy, $C_1$-$C_8$ alkanoyloxy, aryloyloxy,
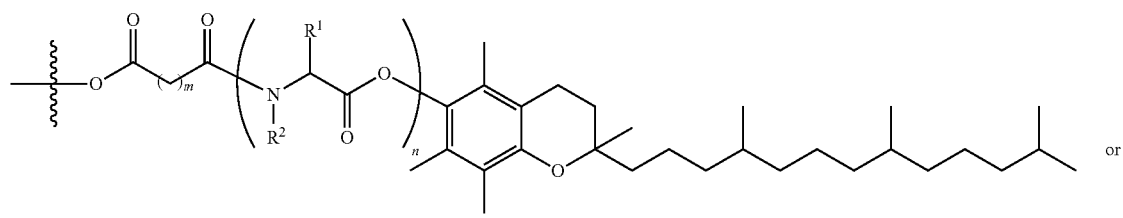 or

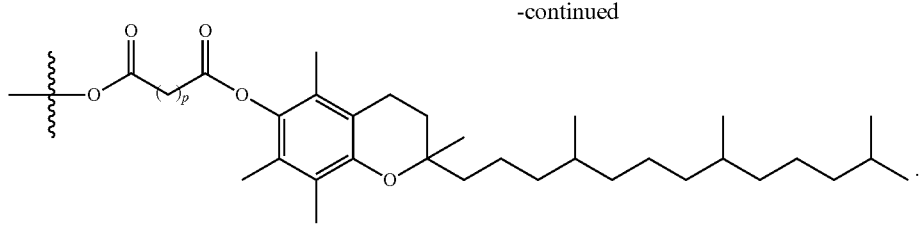

C. The compound of Paragraph A or Paragraph B, wherein $X^1$ is H, halo, hydroxy, amino, cyano, thiol, alkylthio, C1-C6 alkyl, C1-C6 alkoxy, aryloxy, $C_1$-$C_8$ alkanoyloxy, aryloyloxy,

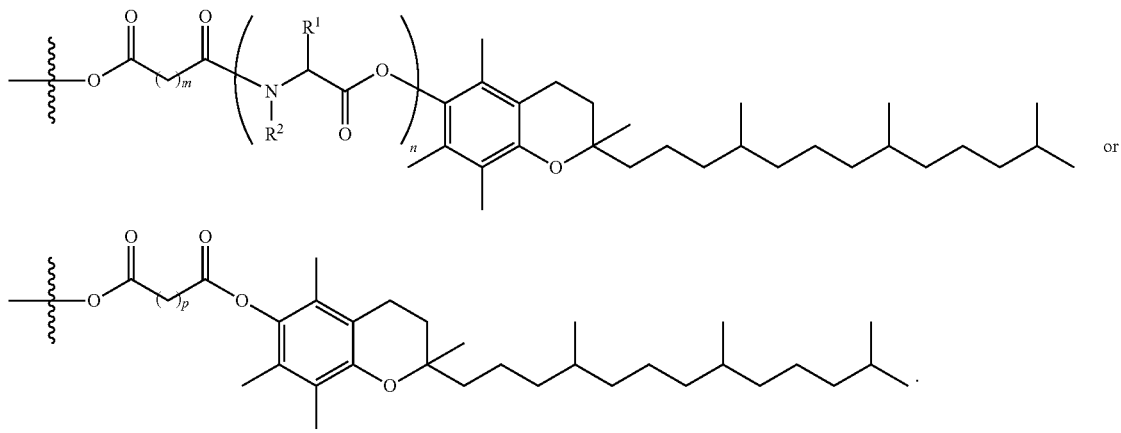

D. The compound of any one of Paragraphs A-C, wherein $X^1$ is H, halo, hydroxy, amino, cyano, thiol, alkylthio, $C_1$-$C_6$ alkyl, $C_1$-$C_6$ alkoxy, aryloxy, $C_1$-$C_8$ alkanoyloxy, or aryloyloxy.

E. The compound of any one of Paragraphs A-D, wherein $X^1$ is H, fluoro, chloro, hydroxy, cyano, $C_1$-$C_6$ alkyl, or $C_1$-$C_6$ alkoxy.

F. The compound of any one of Paragraphs A-E, wherein one of $X^1$ and $X^2$ is

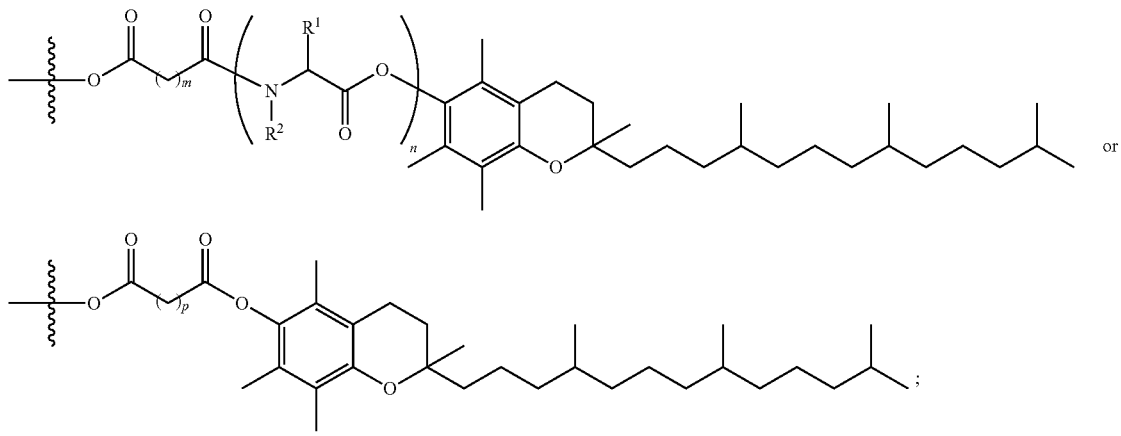

and the other one of $X^1$ and $X^2$ is not.

G. The compound of any one of Paragraphs A-F, wherein one of $X^1$ and $X^2$ is
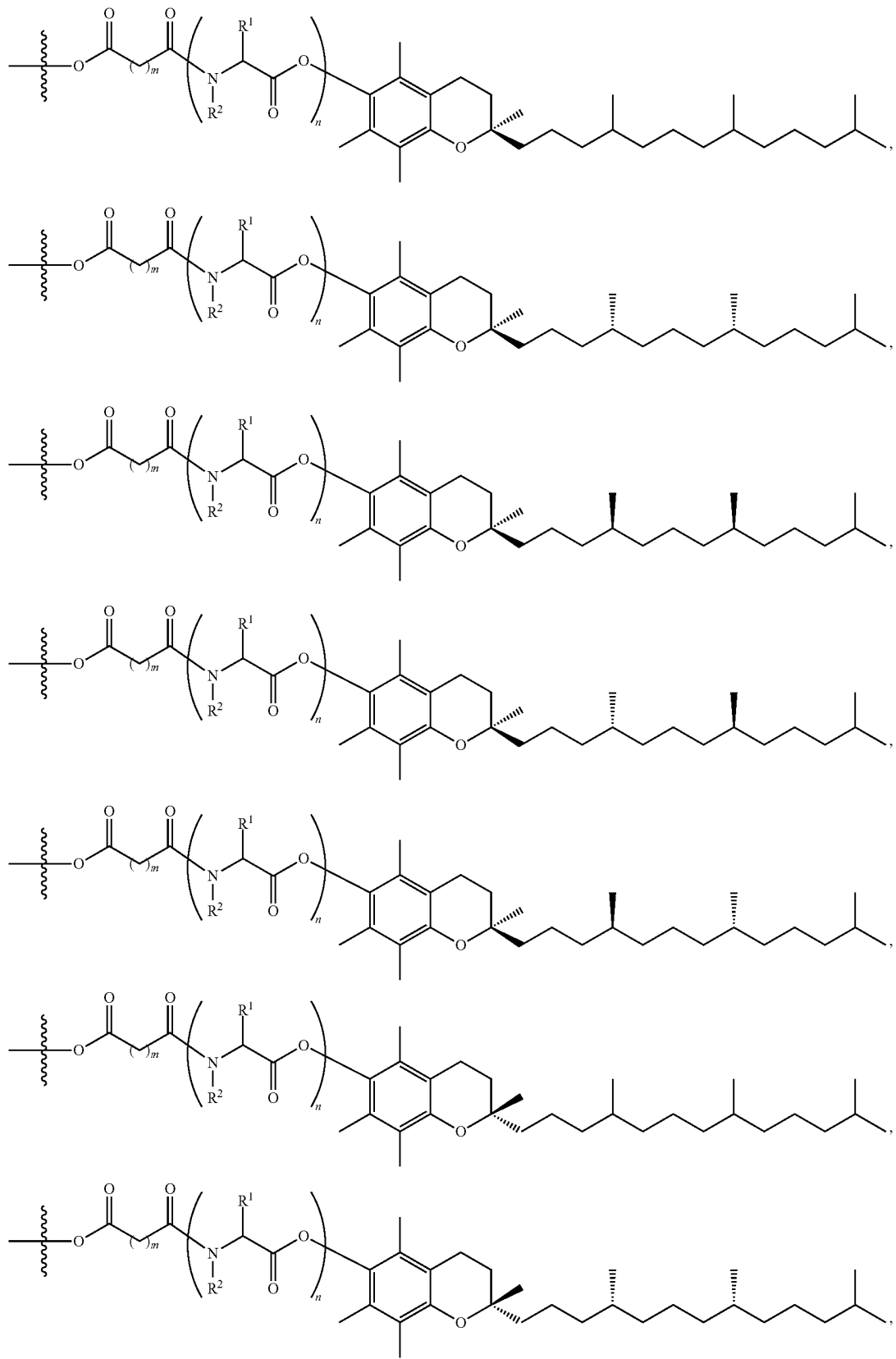

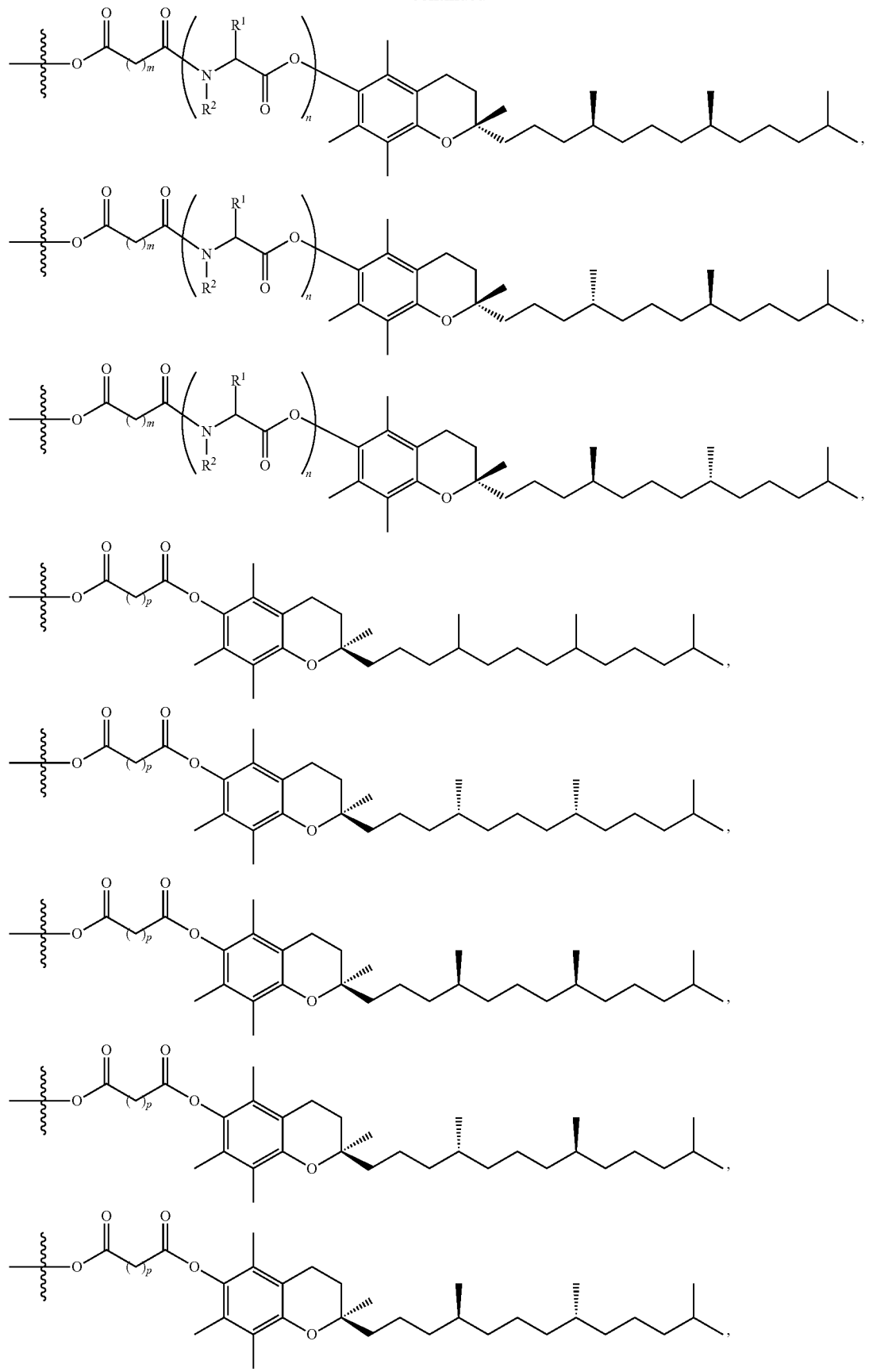

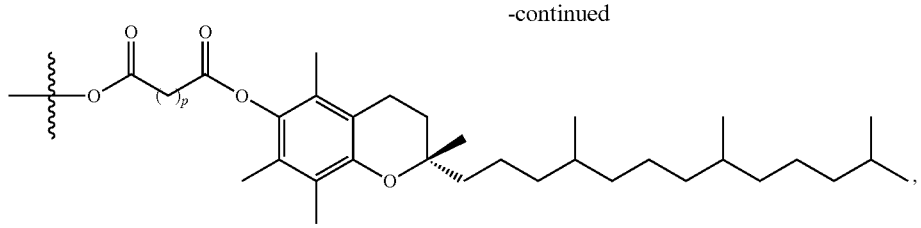,
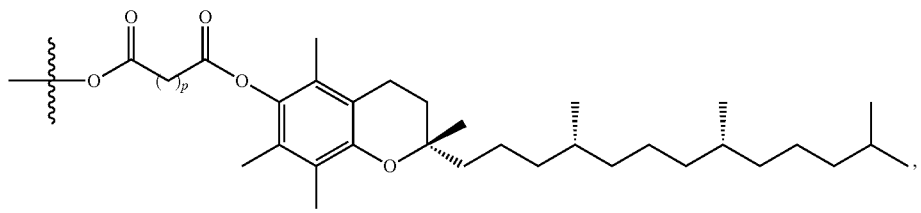,
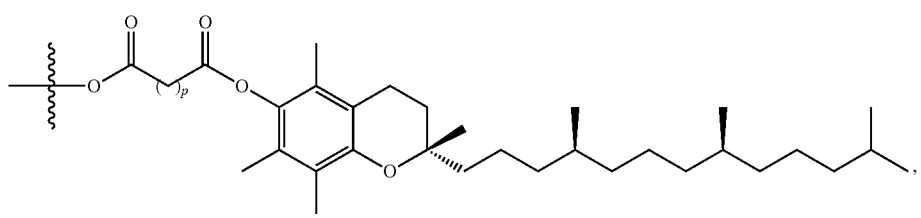,
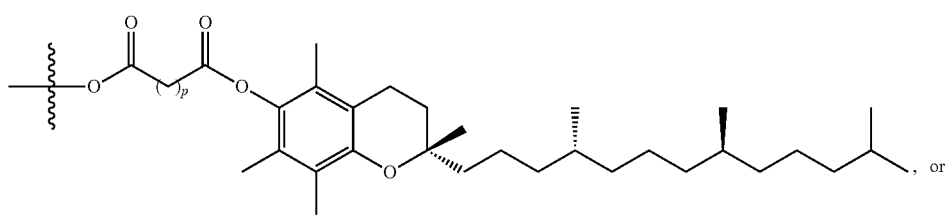, or
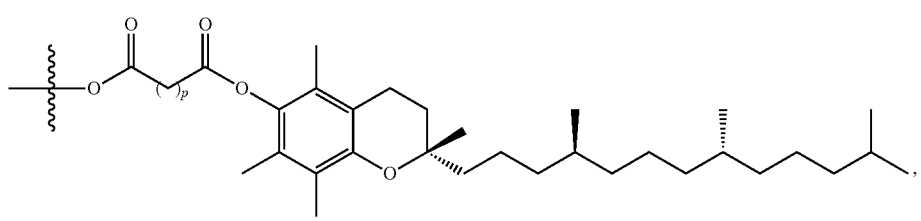,
and the other one of $X^1$ and $X^2$ is not.
H. The compound of any one of Paragraphs A-G, wherein one of $X^1$ and $X^2$ is
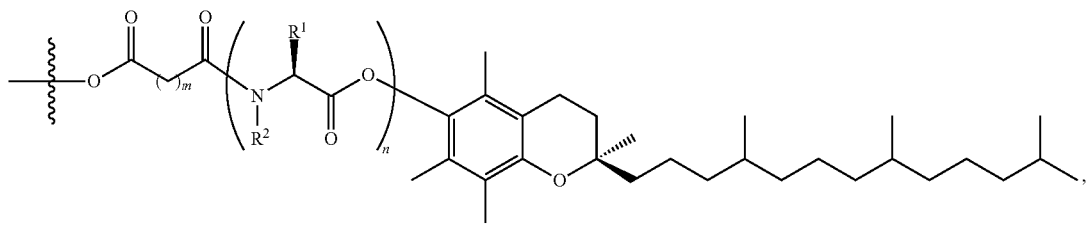,
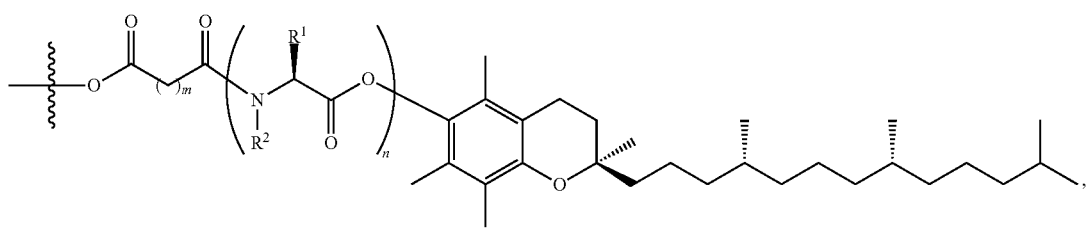, -continued
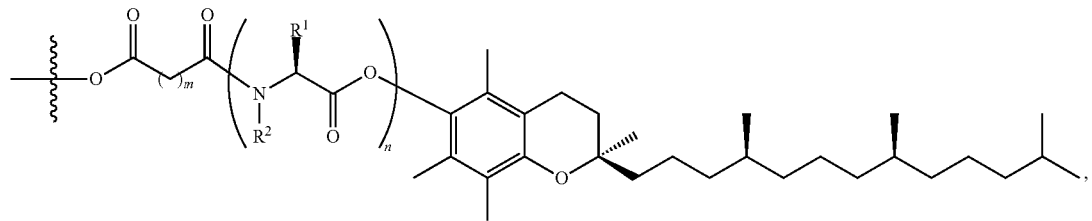
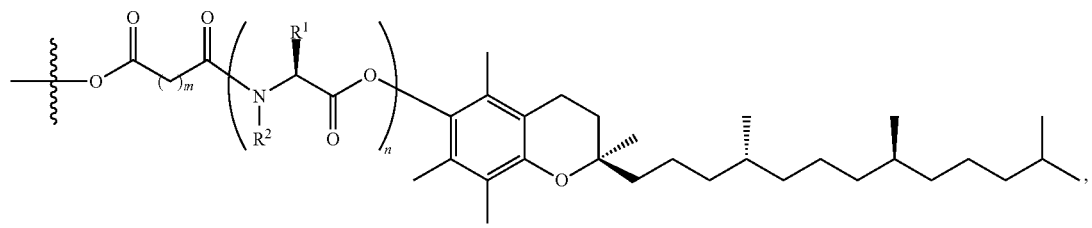
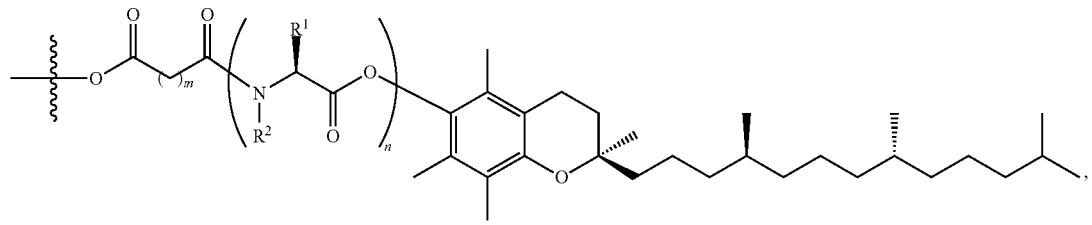
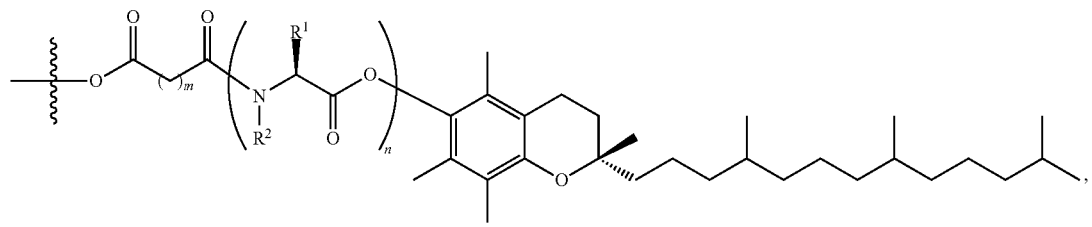
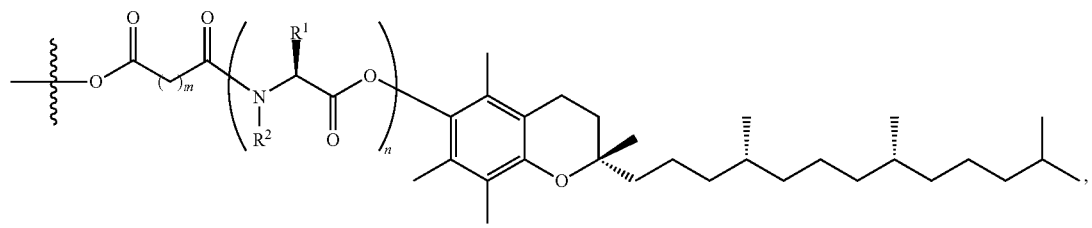
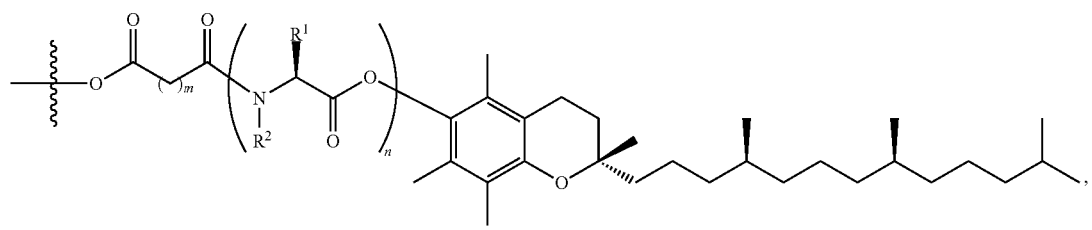
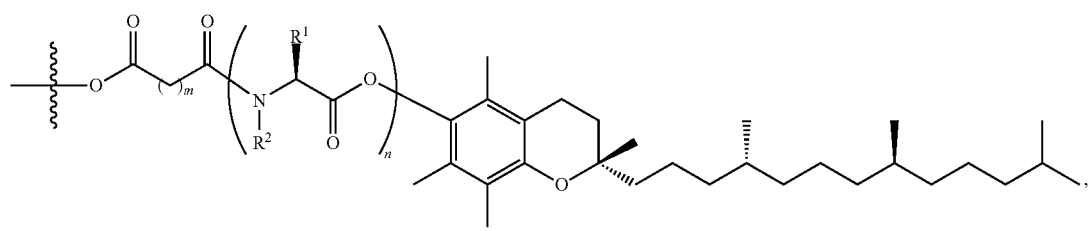

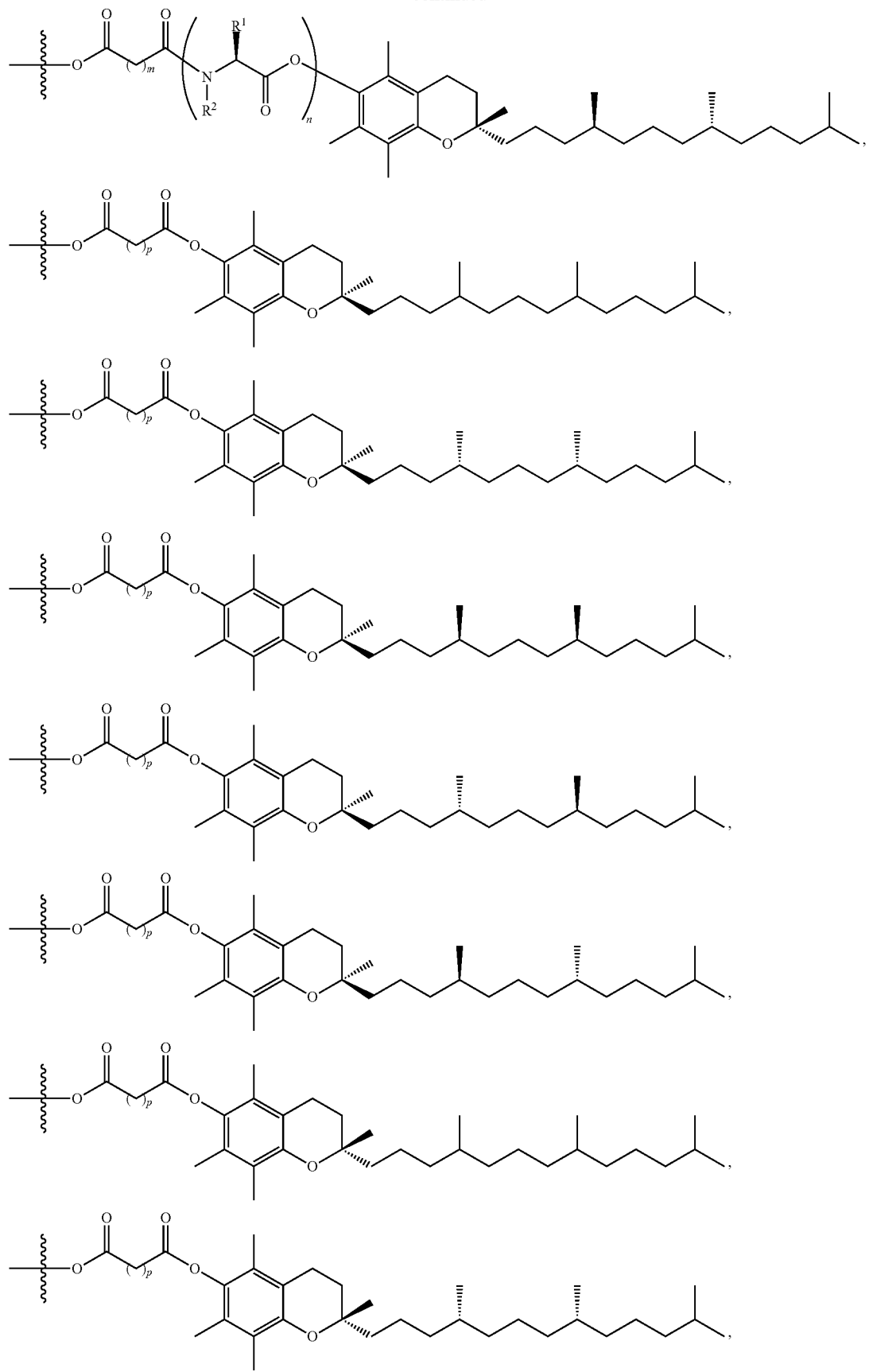

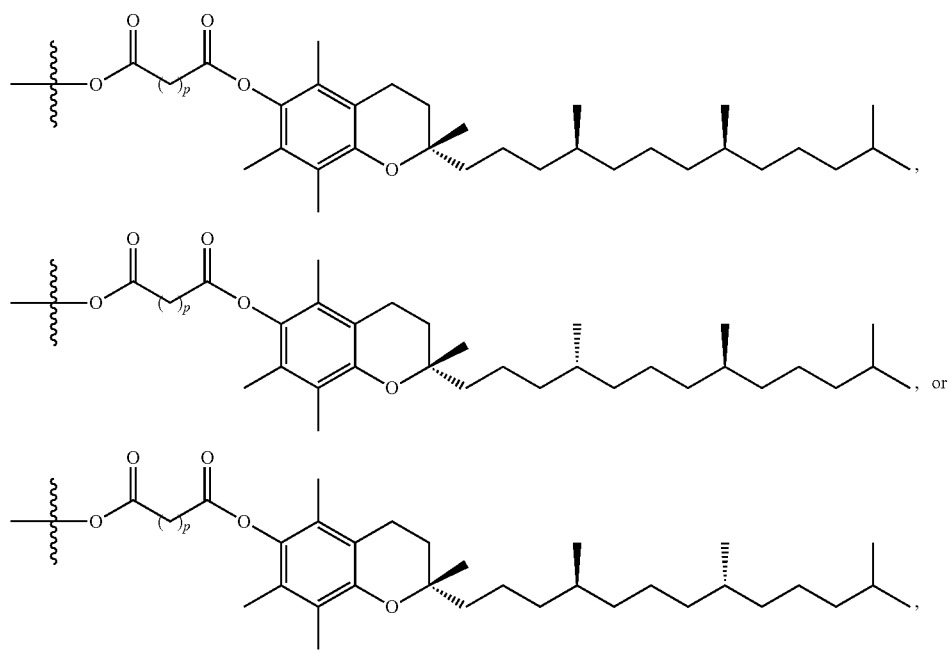
and the other one of $X^1$ and $X^2$ is not.
I. The compound of any one of Paragraphs A-H, wherein one of $X^1$ and $X^2$ is
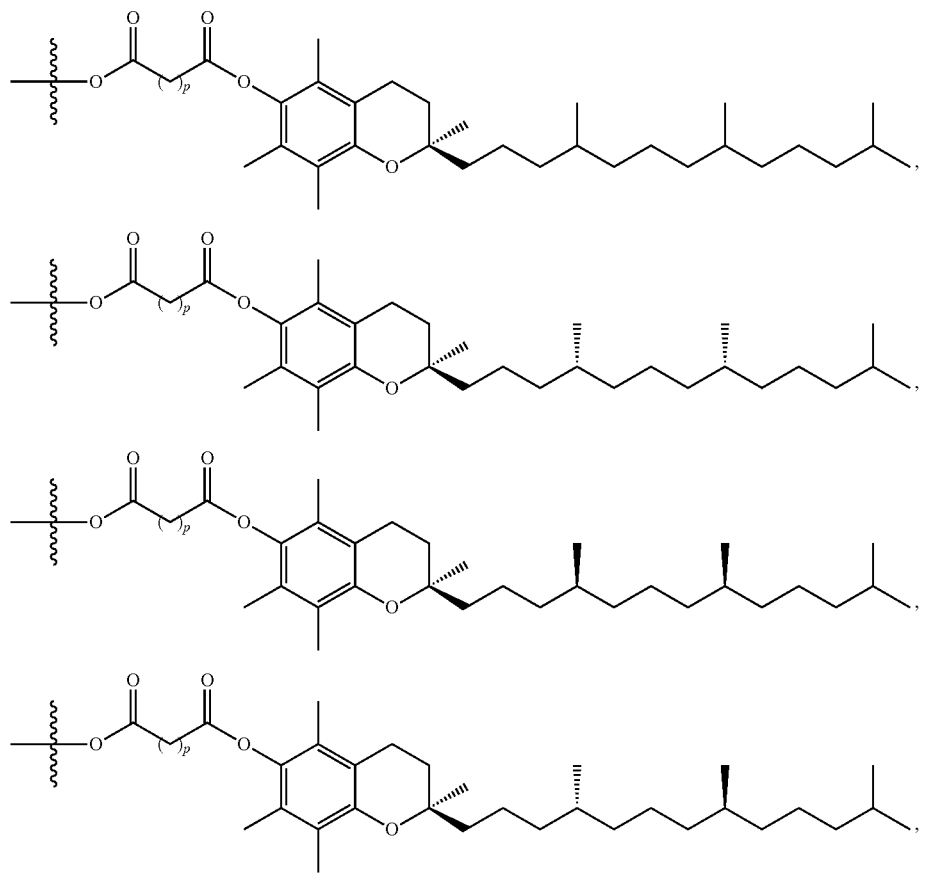

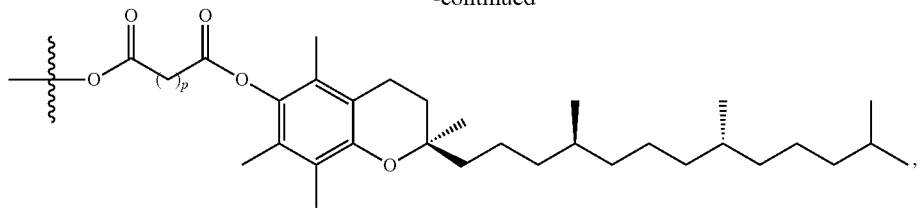
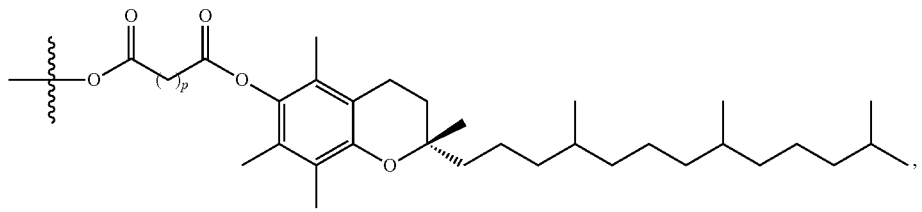
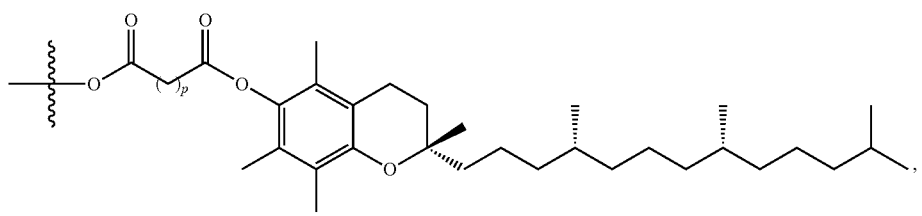
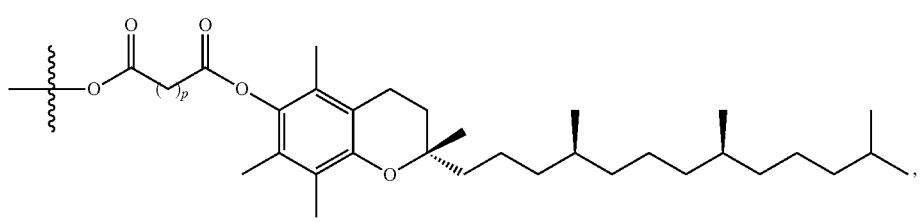
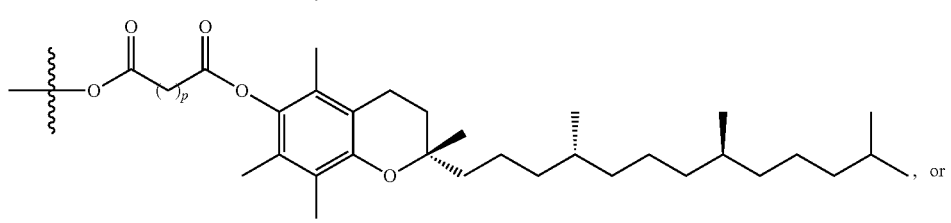, or
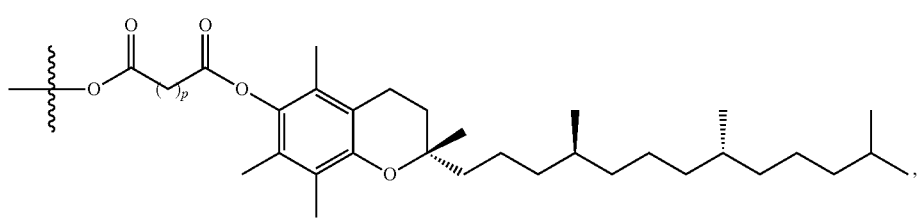
and the other one of $X^1$ and $X^2$ is not.
J. The compound of any one of Paragraphs A-I, wherein the compound is
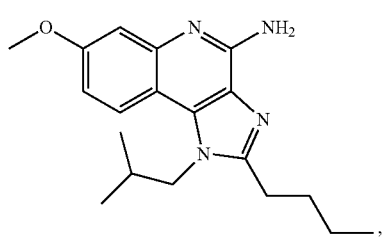 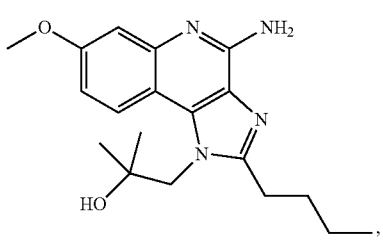 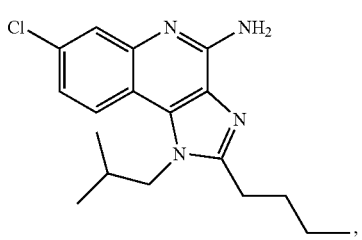

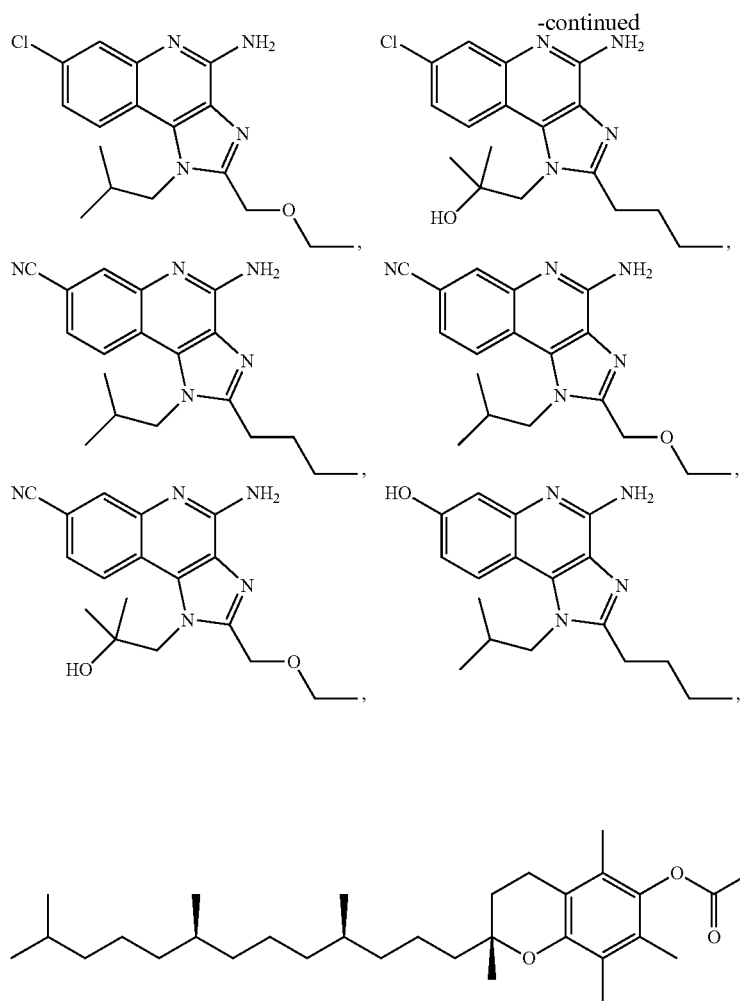
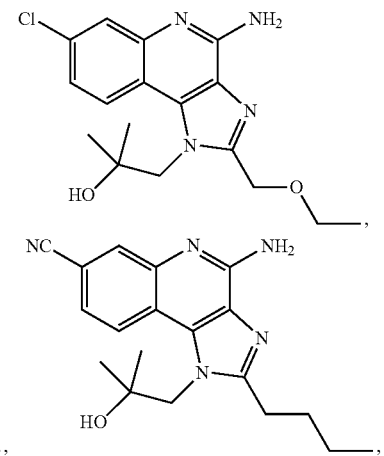
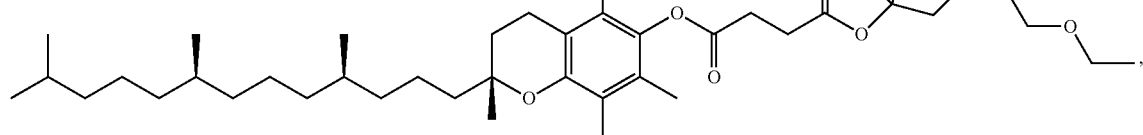

or a pharmaceutically acceptable salt thereof.

K. A composition comprising the compound of any one of Paragraphs A-J, a pharmaceutically acceptable carrier, and optionally a hyaluronan-tocopherol conjugate.

L. The composition of Paragraph K, wherein the composition comprises the compound, the pharmaceutically acceptable carrier, and the hyaluronan-tocopherol conjugate.

M. The composition of Paragraph L, wherein the composition comprises an emulsion of the compound and the hyaluronan-tocopherol conjugate.

N. The composition of any one of Paragraphs K-M, wherein the wherein hyaluronan of the hyaluronan-tocopherol conjugate is substituted on a molar basis with about 6% of tocopherol.

O. The composition of any one of Paragraphs K-N, wherein the hyaluronan-tocopherol conjugate is of Formula II, III, IV, V, or a mixture of any two or more thereof:

(II)

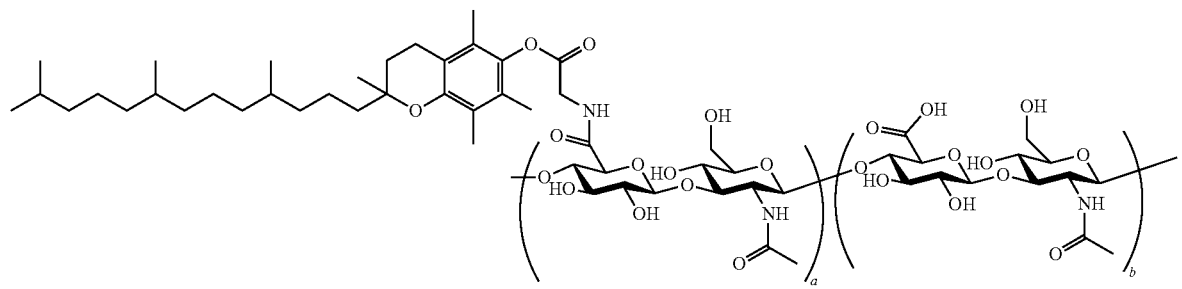

or a pharmaceutically acceptable salt thereof, (III)

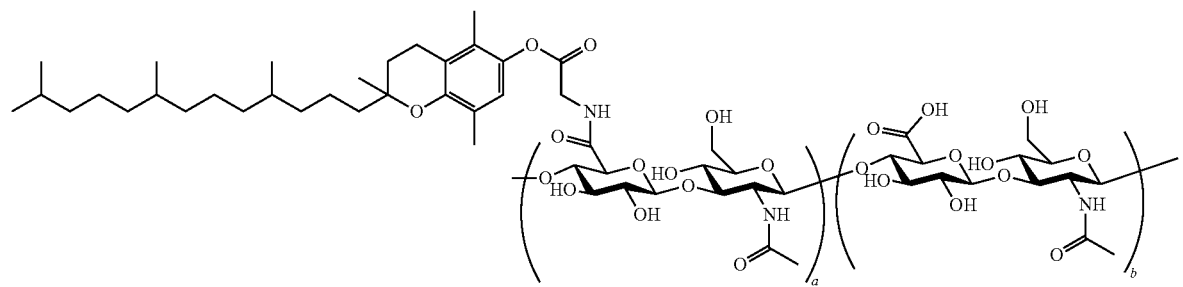

or a pharmaceutically acceptable salt thereof, (IV)

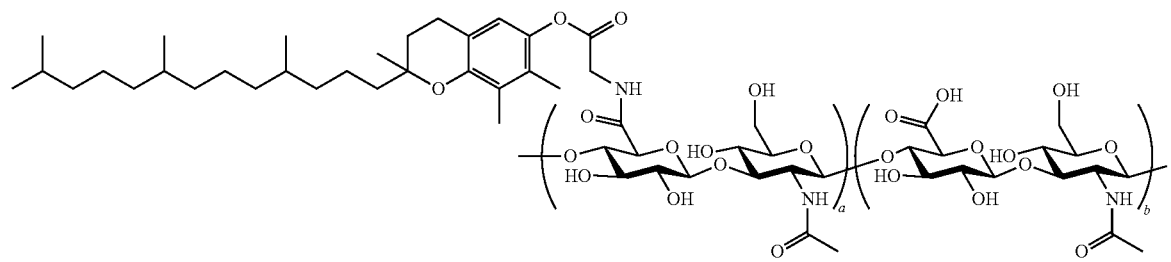

or a pharmaceutically acceptable salt thereof, (V)

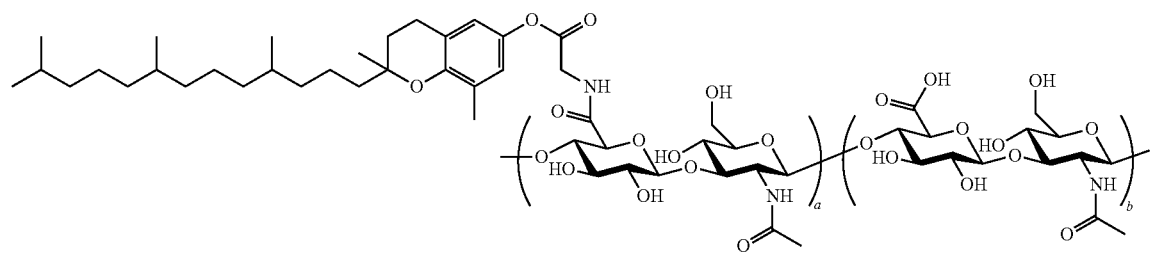

or a pharmaceutically acceptable salt thereof,
wherein a is independently at each occurrence from 1 to 800 and b is independently at each occurrence from 18 to 2540.

P. The composition of any one of Paragraphs K-O, wherein the hyaluronan-tocopherol conjugate is of Formula IIa (IIa)

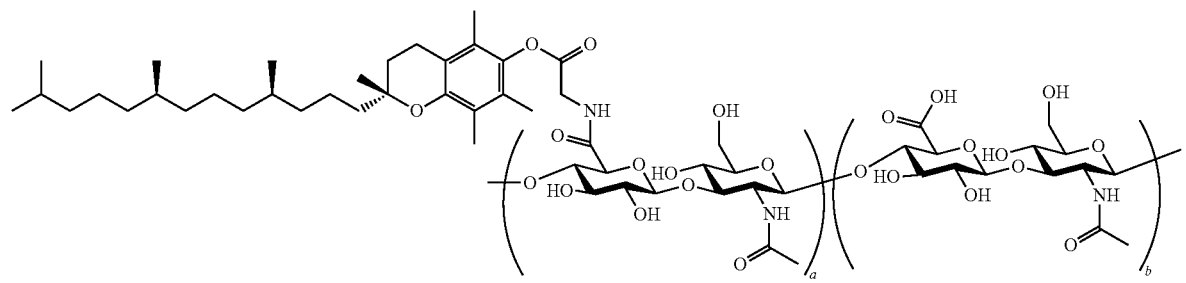

or a pharmaceutically acceptable salt thereof.

Q. A method of treating cancer, superficial basal cell carcinoma, actinic keratosis, cutaneous T-cell lymphoma, or melanoma in a subject, the method comprising administering to the subject an effective amount of a compound of any one of Paragraphs A-J or administering an effective amount of a composition of any one of Paragraphs K-P, wherein the effective amount is an amount effective to treat the cancer, superficial basal cell carcinoma, actinic keratosis, cutaneous T-cell lymphoma, or melanoma.

R. The method of Paragraph Q, wherein the administering comprises oral administration or topical administration.

S. A method of slowing or reversing growth of a tumor in a subject, the method comprising administering to the subject an effective amount of a compound of any one of Paragraphs A-J or administering an effective amount of a composition of any one of Paragraphs K-P, wherein the effective amount is an amount effective to slow or reverse growth of the tumor.

T. The method of Paragraph S, wherein the tumor is of a cancer selected from squamous cell carcinoma, soft tissue sarcoma, oral melanoma, acute lymphoblastic leukemia (ALL), acute myeloid leukemia (AML), adrenocortical carcinoma, AIDS-related cancers, Kaposi sarcoma (soft tissue sarcoma), AIDS-related lymphoma (lymphoma), anal cancer, appendix cancer, gastrointestinal carcinoid tumors, astrocytomas, atypical teratoid/rhabdoid tumor, basal cell carcinoma of the skin, bile duct cancer, bladder cancer, bone cancer (includes Ewing Sarcoma and Osteosarcoma and Malignant Fibrous Histiocytoma), brain tumors, breast cancer, bronchial tumors (lung cancer), Burkitt lymphoma, carcinoid tumor (gastrointestinal), carcinoma of unknown primary, cardiac (heart) tumors, childhood brain cancer, germ cell tumor, primary CNS lymphoma, cervical cancer, cholangiocarcinoma, chordoma, chronic lymphocytic leukemia (CLL), chronic myelogenous leukemia (CML), chronic myeloproliferative neoplasms, colorectal cancer, craniopharyngioma, cutaneous T-cell lymphoma, ductal carcinoma in situ (DCIS), embryonal tumors, medulloblastoma, endometrial cancer (uterine cancer), ependymoma, esophageal cancer, esthesioneuroblastoma (head and neck cancer), extracranial germ cell tumor, eye cancer, retinoblastoma, fallopian tube cancer, fibrous histiocytoma of bone, osteosarcoma, gallbladder cancer, gastric (stomach) cancer, gastrointestinal stromal tumors (GIST) (soft tissue sarcoma), germ cell tumors, childhood central nervous system germ cell tumors (brain cancer), childhood extracranial germ cell tumors, extragonadal germ cell tumors, ovarian germ cell tumors, testicular cancer, gestational trophoblastic disease, hairy cell leukemia, head and neck cancer, heart tumors, hepatocellular (liver) cancer, histiocytosis, Hodgkin lymphoma, intraocular melanoma, islet cell tumors, pancreatic neuroendocrine tumors, kidney (renal cell) cancer, Langerhans cell histiocytosis, laryngeal cancer (head and neck cancer), leukemia, lip and oral cavity cancer (head and neck cancer), liver cancer, lung cancer, lymphoma, male breast cancer, malignant fibrous histiocytoma of bone and osteosarcoma, melanoma, Merkel cell carcinoma (skin cancer), mesothelioma, metastatic cancer, metastatic squamous neck cancer with occult primary (head and neck cancer), midline tract carcinoma with nut gene changes, mouth cancer (head and neck cancer), multiple endocrine neoplasia syndromes, multiple myeloma/plasma cell neoplasms, mycosis fungoides (lymphoma), myelodysplastic syndromes, myelogenous leukemia, myeloid leukemia, myeloproliferative neoplasms, nasal cavity and paranasal sinus cancer (head and neck cancer), nasopharyngeal cancer (head and neck cancer), neuroblastoma, non-Hodgkin lymphoma, non-small cell lung cancer, oral cancer, osteosarcoma and malignant fibrous histiocytoma of bone, ovarian cancer, pancreatic cancer, pancreatic neuroendocrine tumors (islet cell tumors), papillomatosis (childhood laryngeal), paraganglioma, paranasal sinus and nasal cavity cancer (head and neck cancer), parathyroid cancer, penile cancer, pharyngeal cancer (head and neck cancer), pheochromocytoma, pituitary tumor, plasma cell neoplasm/multiple myeloma, pleuropulmonary blastoma (lung cancer), pregnancy and breast cancer, primary central nervous system (CNS) lymphoma, primary peritoneal cancer, prostate cancer, rectal cancer, recurrent cancer, renal cell (kidney) cancer, rhabdomyosarcoma, salivary gland cancer (head and neck cancer), sarcoma, childhood rhabdomyosarcoma, childhood vascular tumors, Ewing sarcoma (bone cancer), Kaposi sarcoma, osteosarcoma (bone cancer), Sézary syndrome (lymphoma), skin cancer, small cell lung cancer, small intestine cancer, squamous cell carcinoma of the skin, squamous neck cancer with occult primary, metastatic (head and neck cancer), stomach (gastric) cancer, T-cell lymphoma, throat cancer (head and neck cancer), oropharyngeal cancer, hypopharyngeal cancer, thymoma and thymic carcinoma, thyroid cancer, tracheobronchial tumors (lung cancer), transitional cell cancer of the renal pelvis and ureter (kidney (renal cell) cancer), urethral cancer, uterine cancer, uterine sarcoma, vaginal cancer, vascular tumors, vulvar cancer, and Wilms tumor and other childhood kidney tumors.

U. The method of Paragraph S or Paragraph T, wherein the administering further comprises administration of a chemotherapeutic agent selected from the group consisting of an alkylating agent; a nitrosourea; an antimetabolite; an anthracycline; a topoisomerase II inhibitor; a mitotic inhibitor; an anti-estrogen; a progestin; an aromatase inhibitor; an anti-androgen; an LHRH agonist; a corticosteroid hormone; a DNA alkylating agent; a taxane; a *vinca* alkaloid; a microtubule poison, and a combination of any two or more thereof.

V. The method of any one of Paragraphs S—U, wherein the administering further comprises administration of a chemotherapeutic agent selected from the group consisting of busulfan, cisplatin, carboplatin, oxaliplatin, an octahedral platinum (IV) compound, chlorambucil, cyclophosphamide, ifosfamide, dacarbazine (DTIC), mechlorethamine (nitrogen mustard), melphalan, temozolomide, carmustine (BCNU), lomustine (CCNU), 5-fluorouracil, capecitabine, 6-mercaptopurine, methotrexate, gemcitabine, cytarabine (ara-C), fludarabine, pemetrexed, daunorubicin, doxorubicin (Adriamycin), epirubicin, idarubicin, mitoxantrone, topotecan, irinotecan, etoposide (VP-16), teniposide, paclitaxel, docetaxel, vinblastine, vincristine, vinorelbine, prednisone, dexamethasone, L-asparaginase, dactinomycin, thalidomide, tretinoin, imatinib (Gleevec), gefitinib (Iressa), erlotinib (Tarceva), rituximab (Rituxan), bevacizumab (Avastin), ipilimumab, nivolumab (Opdivo), pembrolizumab (Ketruda), tamoxifen, fulvestrant, anastrozole, exemestane, letrozole, megestrol acetate, bicalutamide, flutamide, leuprolide, goserelin, and a combination of any two or more thereof.

W. The method of any one of Paragraphs S-V, wherein the administering comprises local administration of the compound to the tumor or local administration of the composition to the tumor.

X. The method of any one of Paragraphs S-W, wherein the administering comprises oral, rectal, nasal, vaginal, transdermal, intravenous, intramuscular, or inhalation administration.

Y. The method of any one of Paragraphs S-X, wherein the administering comprises injection of the compound into the tumor or proximal to the tumor.

Z. A method of vaccinating a subject, wherein the method comprises administering a vaccine for a disease and administering a vaccine adjuvant comprising a compound of any one of Paragraphs A-J or a composition of any one of Paragraphs K-P.

AA. The method of Paragraph Z, wherein the vaccine adjuvant is administered concurrently with the vaccine.

AB. The method of Paragraph Z, wherein the vaccine adjuvant is administered sequentially with the vaccine.

Other embodiments are set forth in the following claims, along with the full scope of equivalents to which such claims are entitled.

What is claimed is:

1. A composition comprising
(a) compound of Formula I

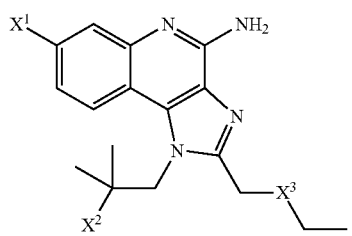

or a pharmaceutically acceptable salt thereof, wherein
$X^1$ is H, halo, hydroxy, amino, cyano, trifluoromethyl, thiol, alkylthio, sulfoxide, sulfone, nitro, pentafluorosulfanyl, carboxylate, amide, ester, $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, aryloyloxy,

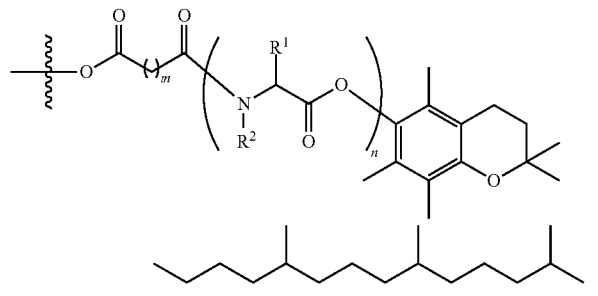

where $R^1$ and $R^2$ are each independently H, or

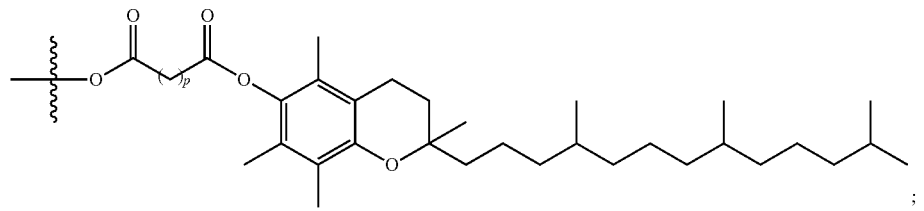

$X^2$ is H, hydroxyl,

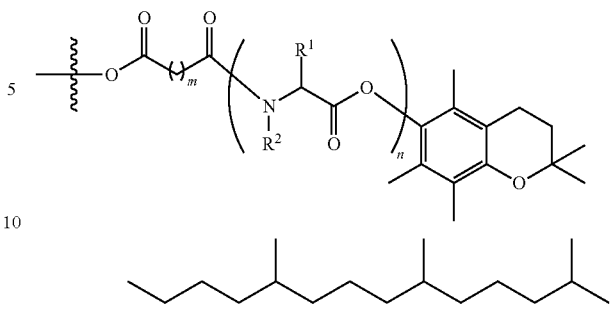

where $R^1$ and $R^2$ are each independently H, or

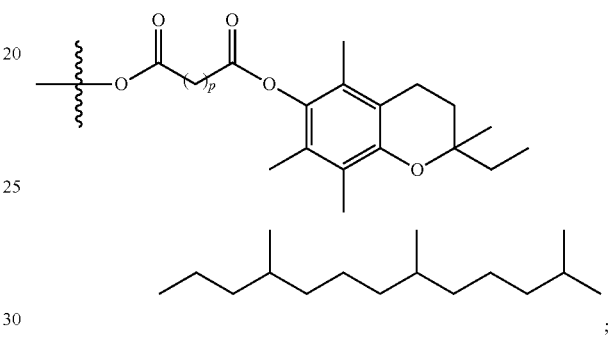

m is 1, 2, 3, 4, 5, 6, 7, or 8;
n is 1, 2, or 3;
p is 1, 2, 3, 4, 5, 6, 7, or 8; and
$X^3$ is $CH_2$ or O;
provided that at least one of $X^1$ and $X^2$ is not

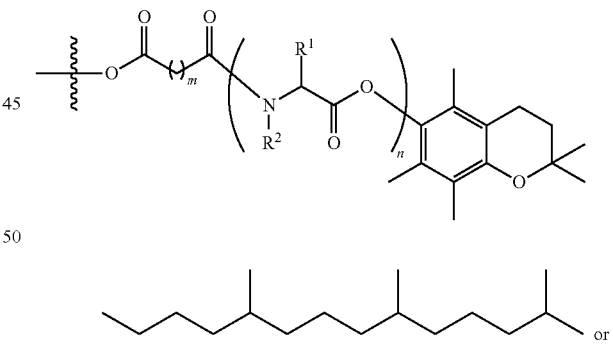

or

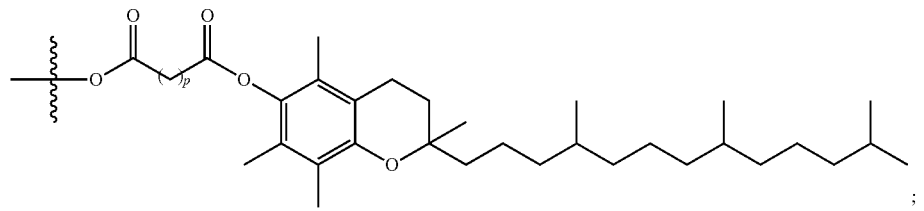

;

-continued

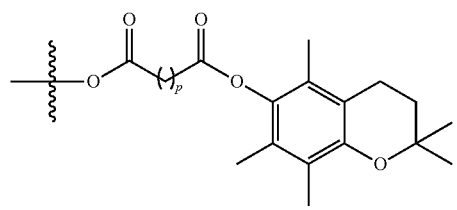

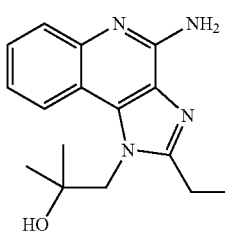

and wherein the compound of Formula I is not (b) a pharmaceutically acceptable carrier; and
(c) a hyaluronan-tocopherol conjugate of Formula II, III, IV, V, or a mixture of any two or more thereof:

(II)

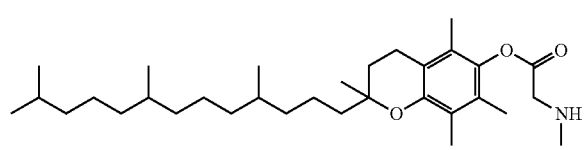

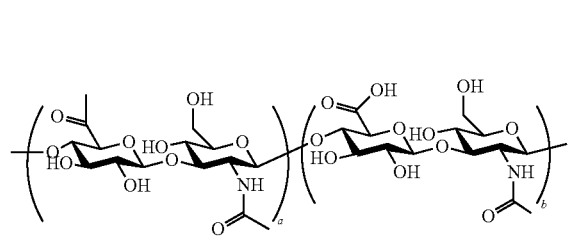

or a pharmaceutically acceptable salt thereof, (III)

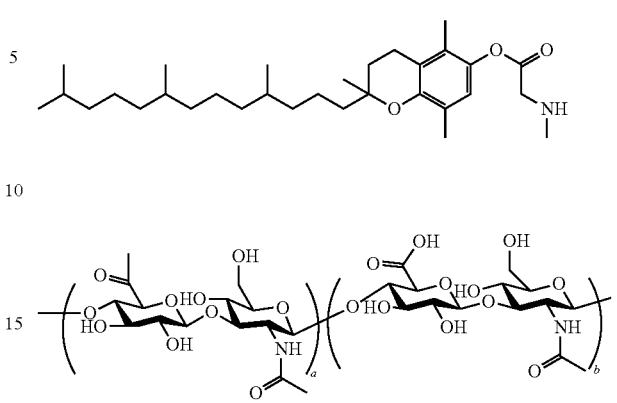

or a pharmaceutically acceptable salt thereof, (IV)

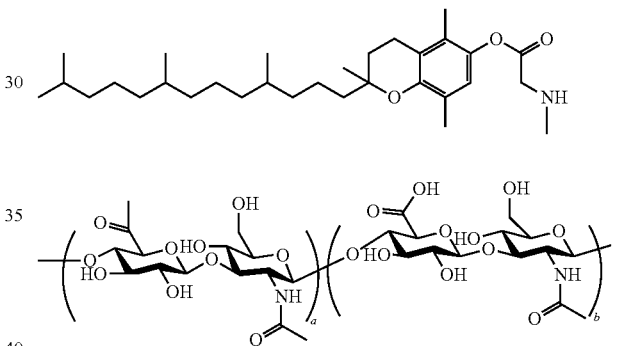

or a pharmaceutically acceptable salt thereof, (V)

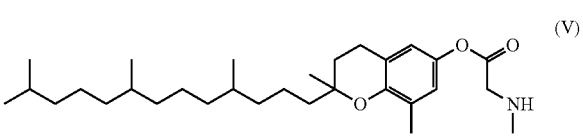

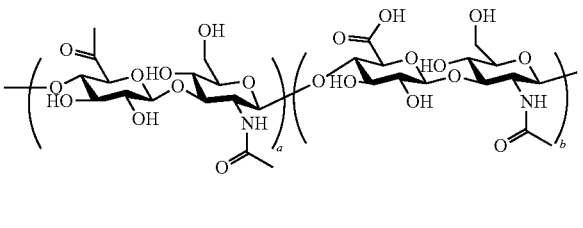

or a pharmaceutically acceptable salt thereof,
wherein a is independently at each occurrence from 1 to 800 and b is independently at each occurrence from 18 to 2540.

2. The composition of claim 1, wherein the hyaluronan-tocopherol conjugate is of Formula IIa

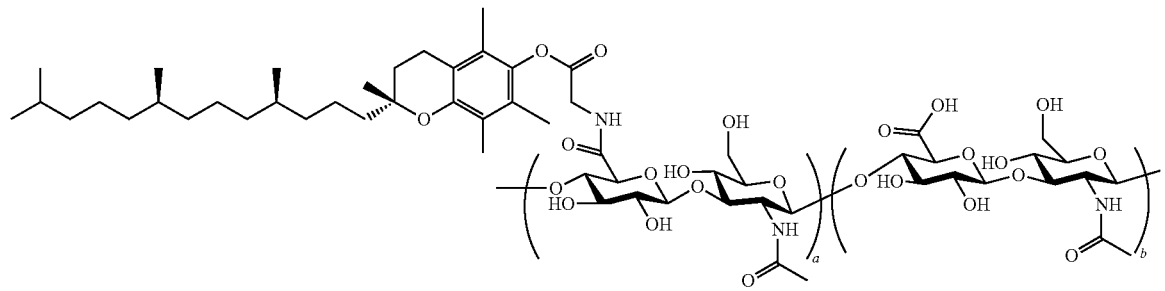

(IIa)

or a pharmaceutically acceptable salt thereof.

3. A method of treating superficial basal cell carcinoma, actinic keratosis, cutaneous T-cell lymphoma, or melanoma in a subject, the method comprising administering to the subject an effective amount of a composition of claim 1, wherein the effective amount is an amount effective to treat superficial basal cell carcinoma, actinic keratosis, cutaneous T-cell lymphoma, or melanoma.

4. A method of slowing or reversing growth of a tumor in a subject, the method comprising administering to the subject an effective amount of a composition of claim 1, wherein the effective amount is an amount effective to slow or reverse growth of the tumor.

5. The method of claim 4, wherein the administering further comprises administration of a chemotherapeutic agent selected from the group consisting of an alkylating agent; a nitrosourea; an antimetabolite; an anthracycline; a topoisomerase II inhibitor; a mitotic inhibitor; an anti-estrogen; a progestin; an aromatase inhibitor; an anti-androgen; an LHRH agonist; a corticosteroid hormone; a DNA alkylating agent; a taxane; a *vinca* alkaloid; a microtubule poison, and a combination of any two or more thereof.

6. A method of vaccinating a subject, wherein the method comprises administering a vaccine for a disease and administering a vaccine adjuvant comprising a composition of claim 1.

7. The composition of claim 1, wherein
$X^1$ is H, halo, hydroxy, amino, cyano, thiol, alkylthio, $C_1$-$C_6$ alkyl, $C_1$-$C_6$ alkoxy, aryloxy, $C_1$-$C_8$ alkanoyloxy, aryloyloxy,

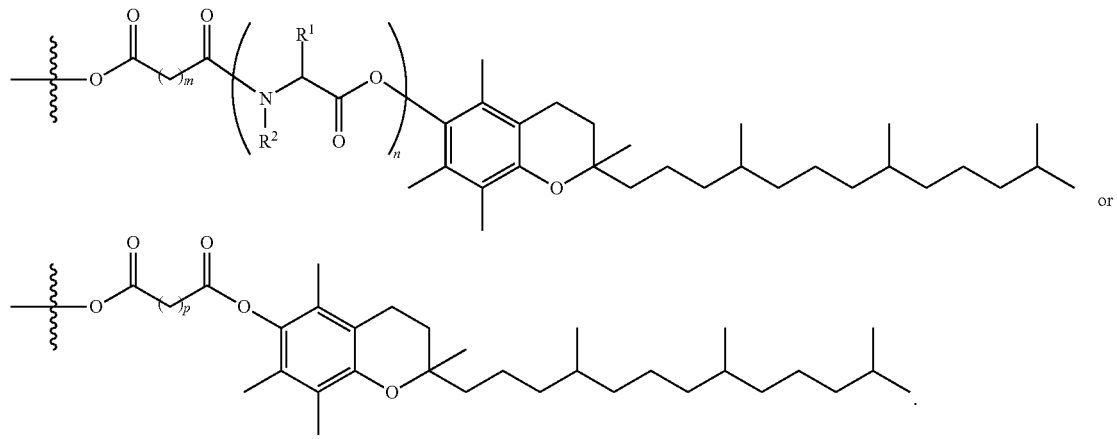

or

8. The composition of claim 1, wherein
$X^1$ is H, fluoro, chloro, hydroxy, cyano, $C_1$-$C_6$ alkyl, $C_1$-$C_6$ alkoxy,

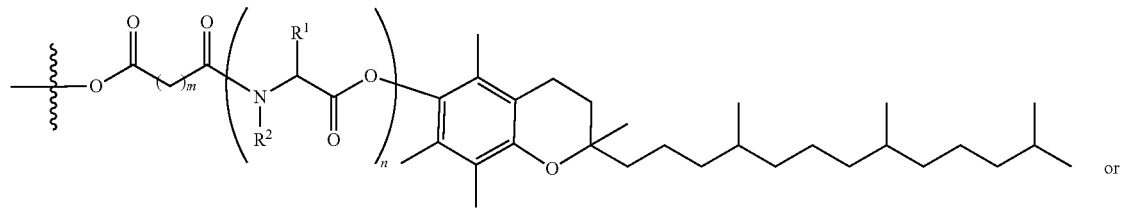

or

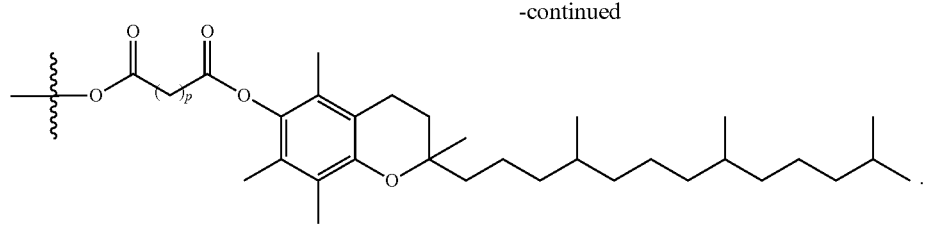

9. The composition of claim 1, wherein $X^1$ is H, halo, hydroxy, amino, cyano, thiol, alkylthio, $C_1$-$C_6$ alkyl, $C_1$-$C_6$ alkoxy, aryloxy, $C_1$-$C_8$ alkanoyloxy, or aryloyloxy.

10. The composition of claim 1, wherein $X^1$ is H, fluoro, chloro, hydroxy, cyano, $C_1$-$C_6$ alkyl, or $C_1$-$C_6$ alkoxy.

11. The composition of claim 1, wherein the compound is

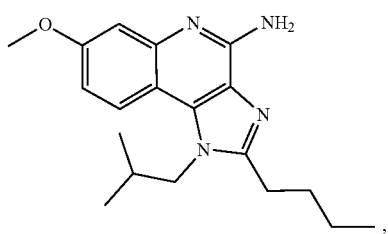

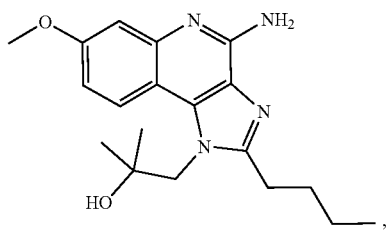

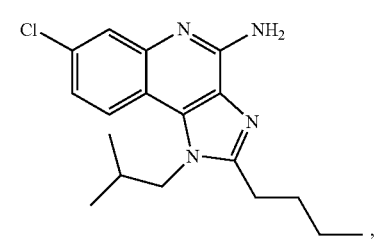

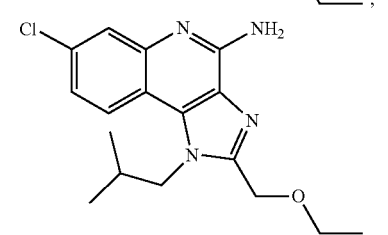

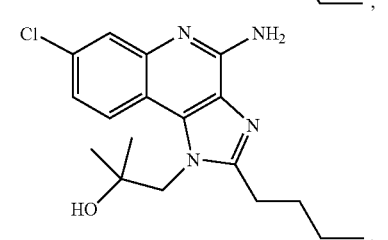

-continued

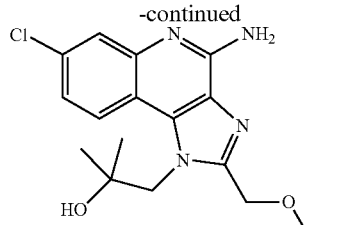

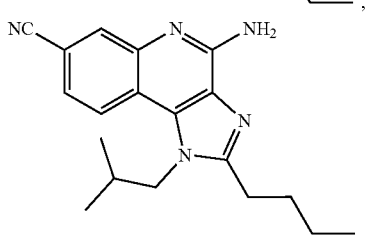

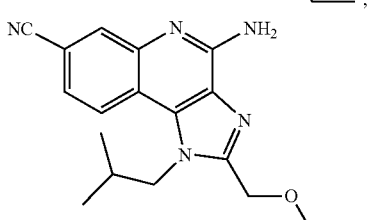

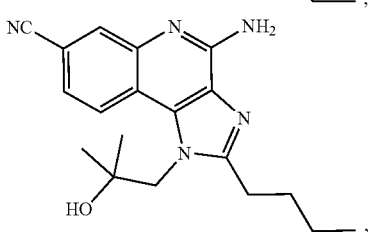

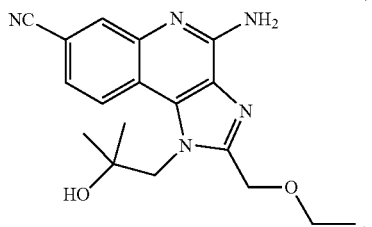

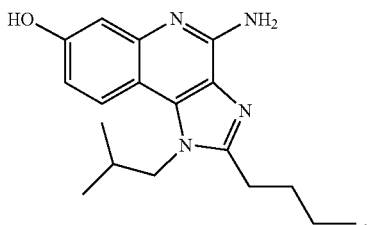

or a pharmaceutically acceptable salt thereof.

12. A compound of Formula I

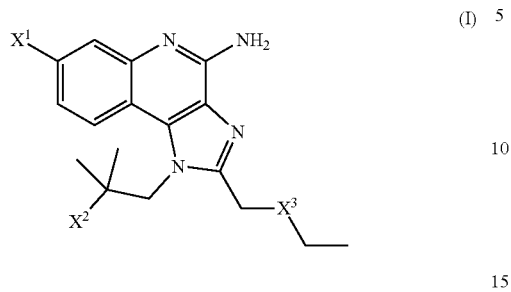

(I)

or a pharmaceutically acceptable salt thereof, wherein
X$^1$ is H, halo, hydroxy, amino, cyano, trifluoromethyl, thiol, alkylthio, sulfoxide, sulfone, nitro, pentafluorosulfanyl, carboxylate, amide, ester, $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, aryloyloxy,

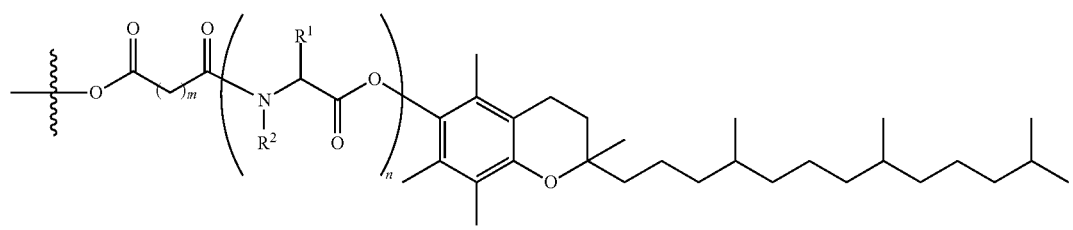

where R$^1$ and R$^2$ are each independently H, or

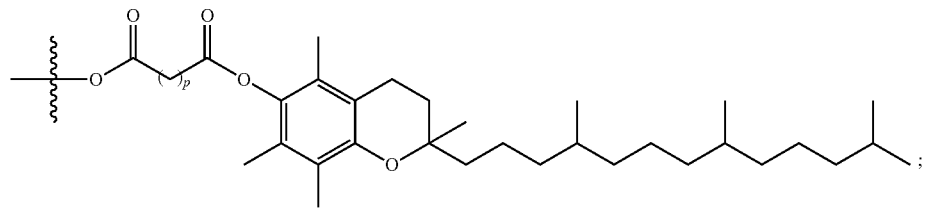

X$^2$ is H, hydroxyl,

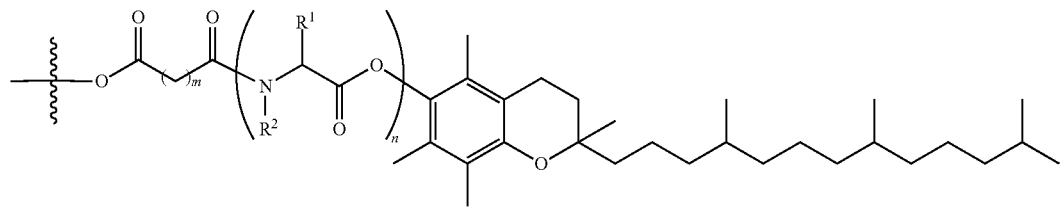

where R$^1$ and R$^2$ are each independently H, or

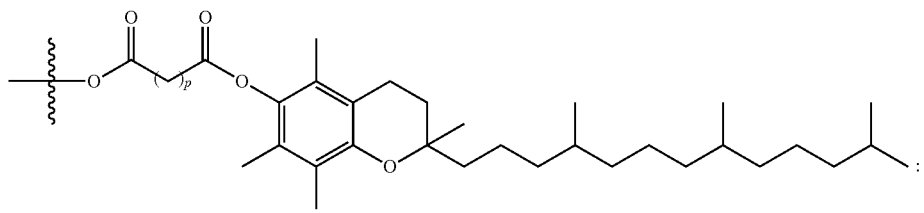
m is 1, 2, 3, 4, 5, 6, 7, or 8;
n is 1, 2, or 3;
p is 1, 2, 3, 4, 5, 6, 7, or 8; and
$X^3$ is $CH_2$ or O;
provided that at least one of $X^1$ and $X^2$ is
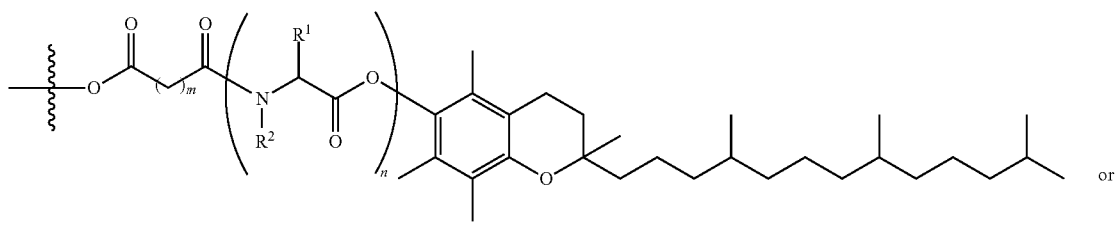
or
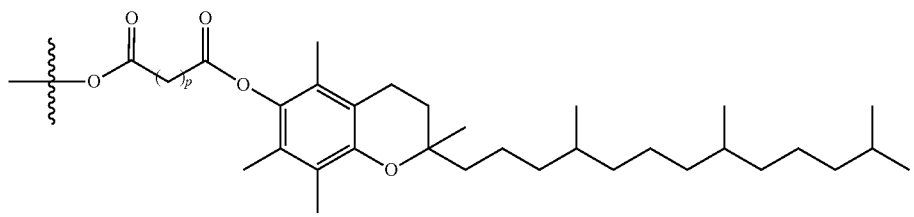
and the other one of $X^1$ and $X^2$ is not.
13. The compound of claim 12, wherein
$X^1$ is H, halo, hydroxy, amino, cyano, thiol, alkylthio, $C_1$-$C_6$ alkyl, $C_1$-$C_6$ alkoxy, aryloxy, $C_1$-$C_8$ alkanoyloxy, aryloyloxy,
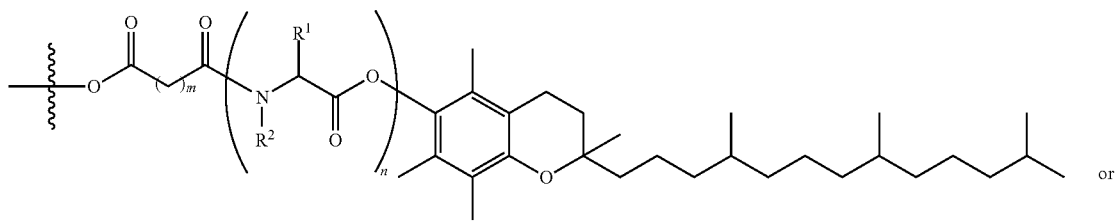
or
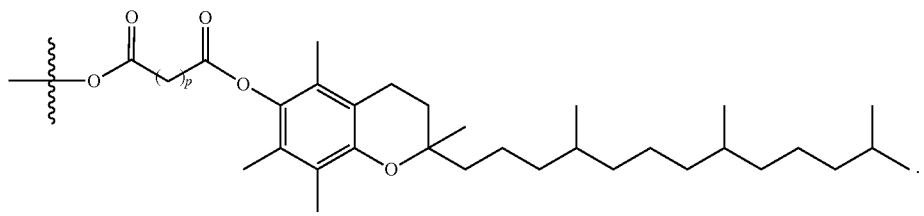
.

14. The compound of claim 12, wherein
$X^1$ is H, fluoro, chloro, hydroxy, cyano, $C_1$-$C_6$ alkyl, $C_1$-$C_6$ alkoxy,

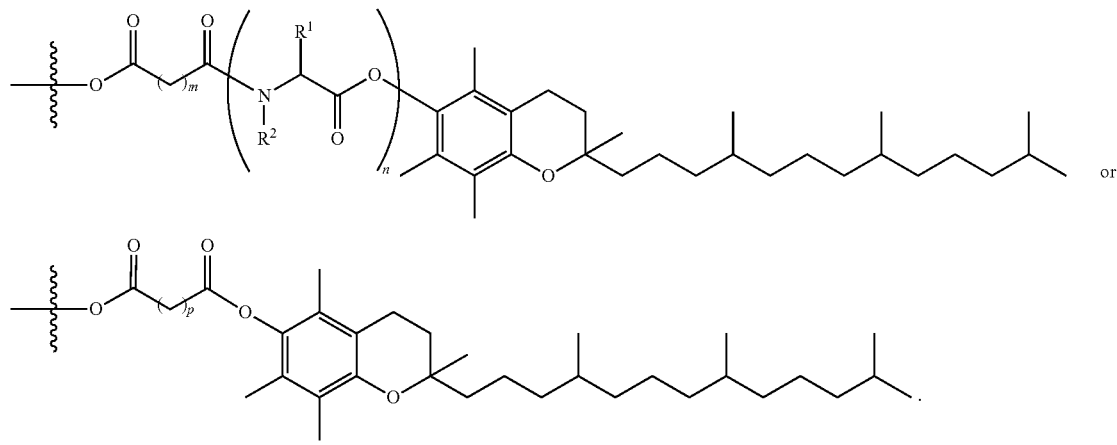

or

15. The compound of claim 12, wherein $X^1$ is H, halo, hydroxy, amino, cyano, thiol, alkylthio, $C_1$-$C_6$ alkyl, $C_1$-$C_6$ alkoxy, aryloxy, $C_1$-$C_8$ alkanoyloxy, or aryloyloxy.

16. The compound of claim 12, wherein $X^1$ is H, fluoro, chloro, hydroxy, cyano, $C_1$-$C_6$ alkyl, or $C_1$-$C_6$ alkoxy.

17. The compound of claim 12, wherein one of $X^1$ and $X^2$ is

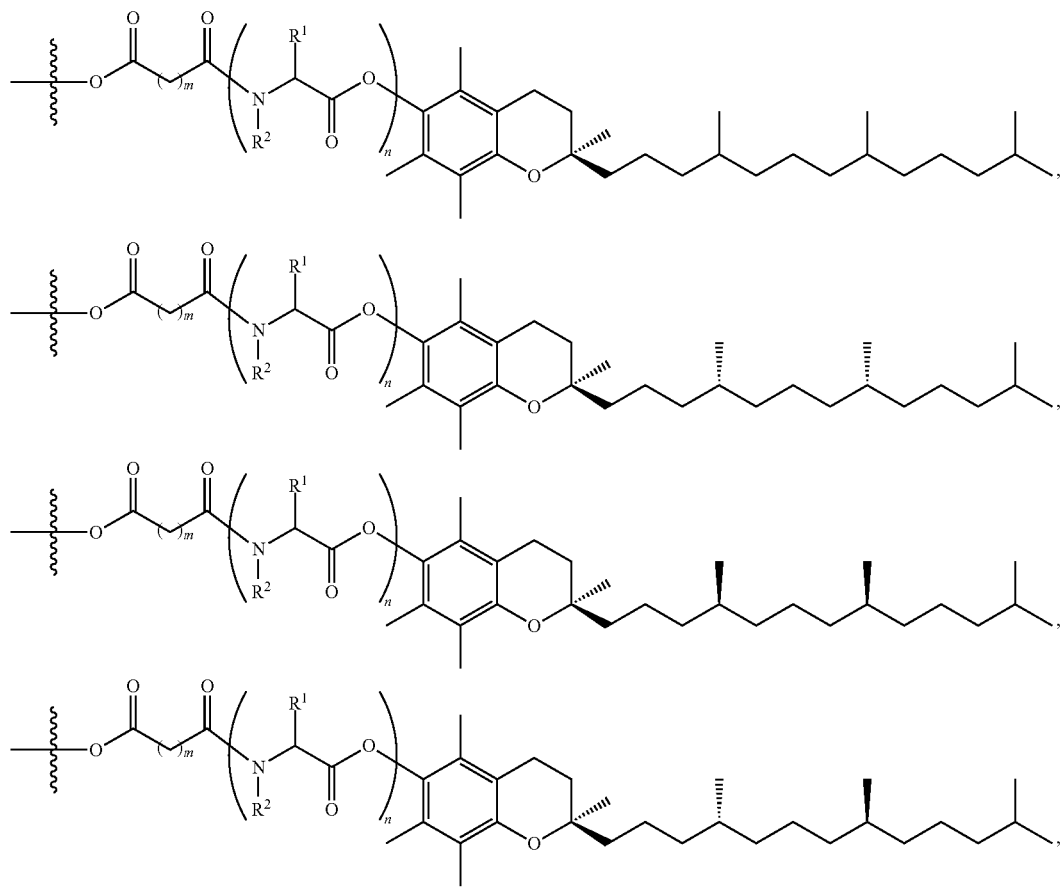

-continued
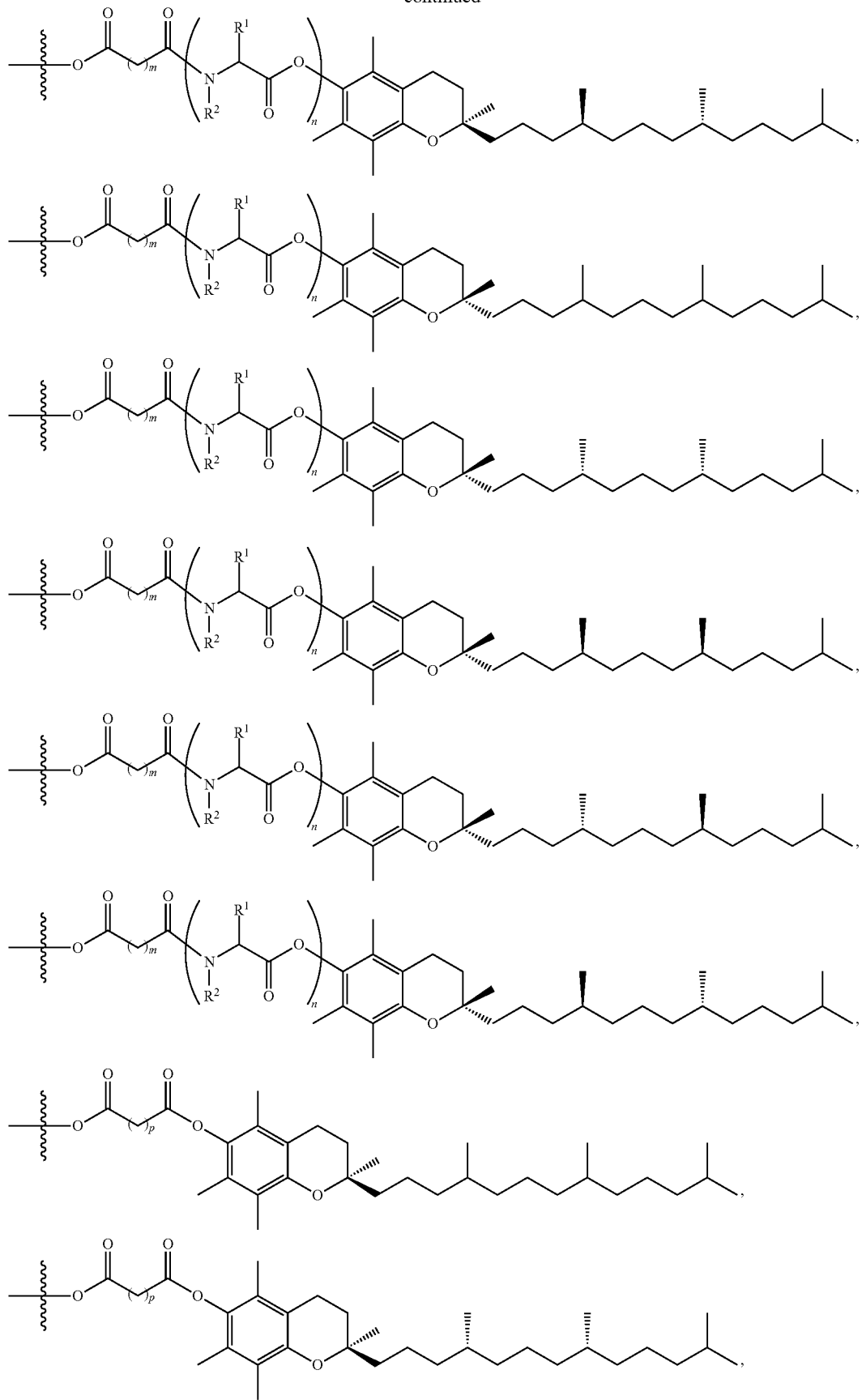

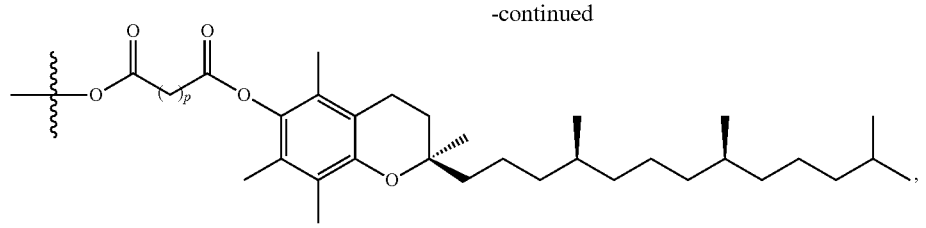
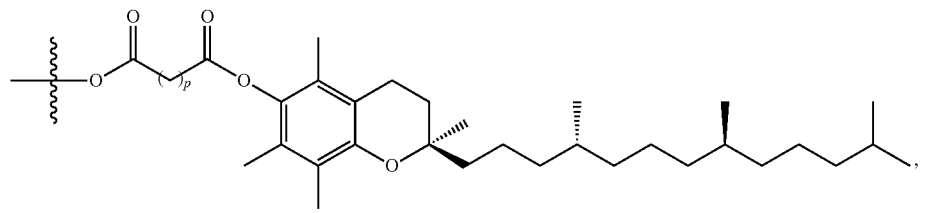
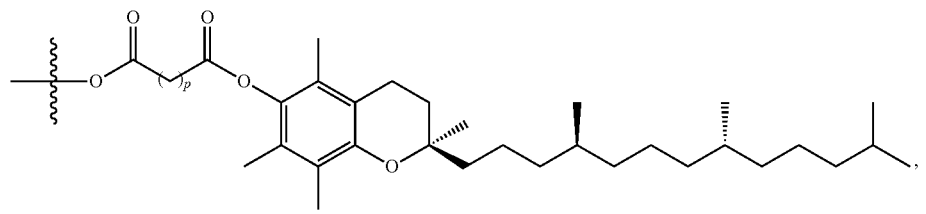
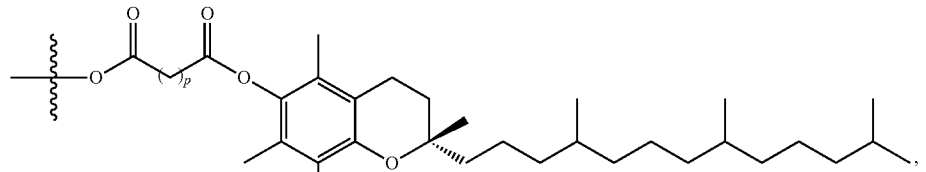
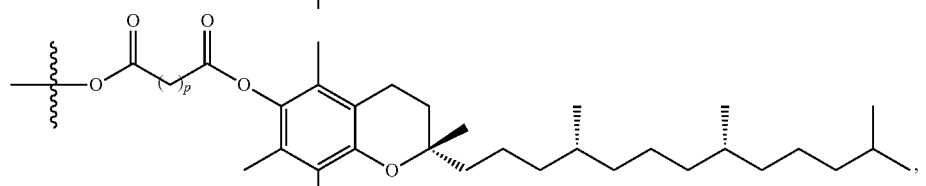
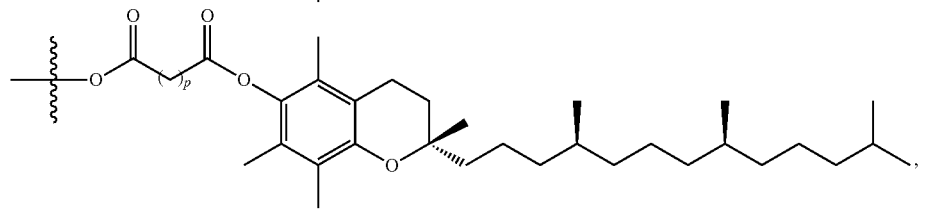
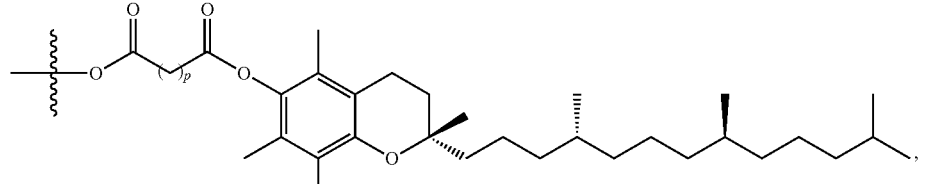, or
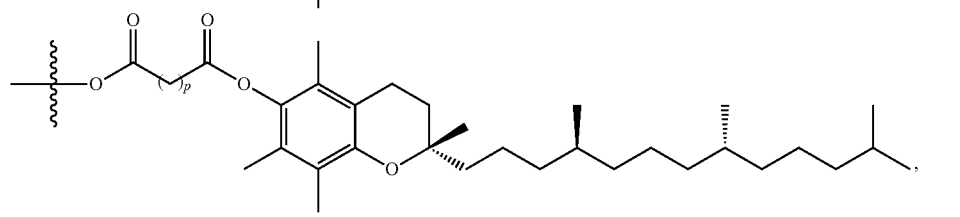
and the other one of $X^1$ and $X^2$ is not.

18. The compound of claim 12, wherein one of $X^1$ and $X^2$ is
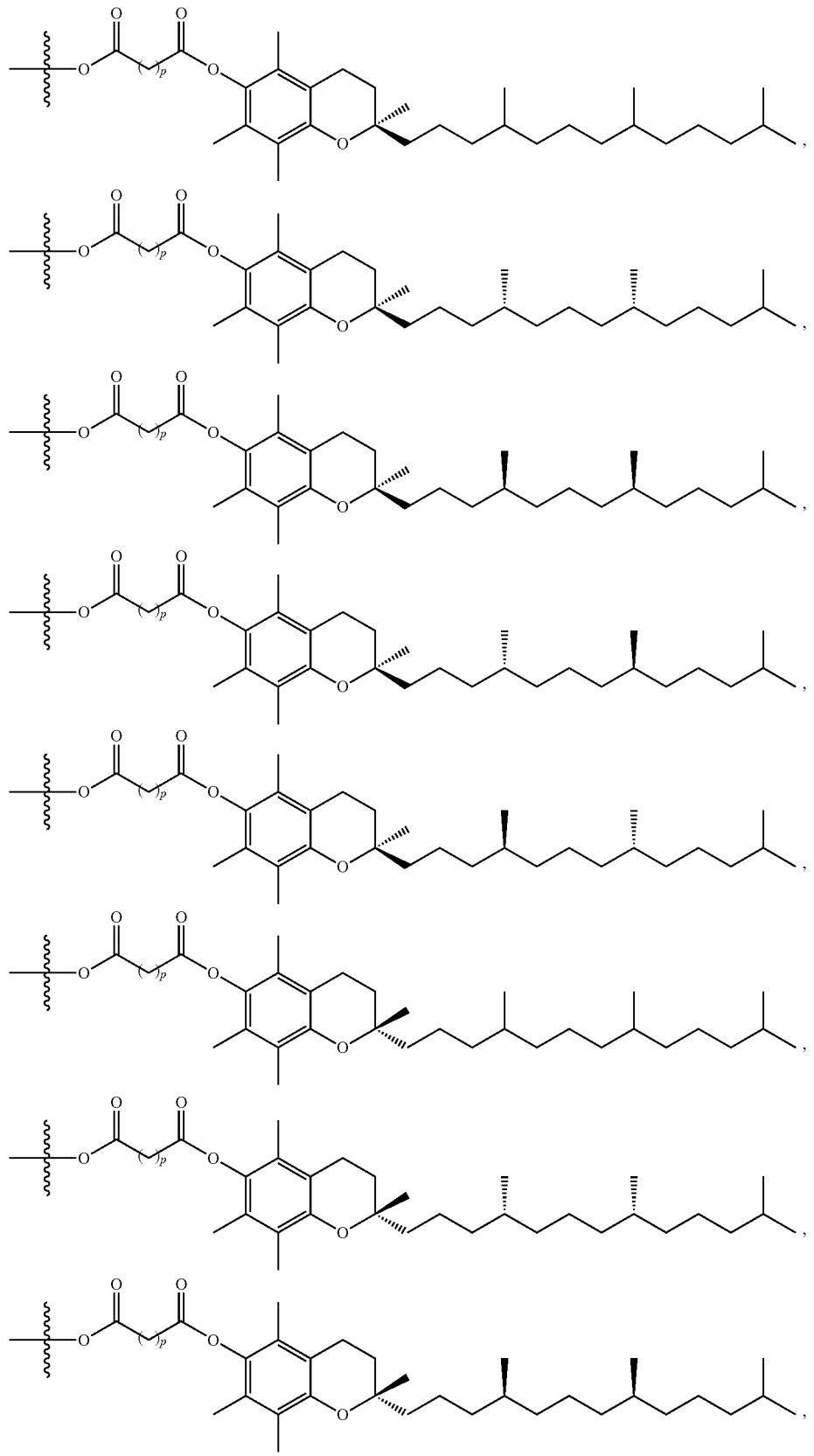

-continued

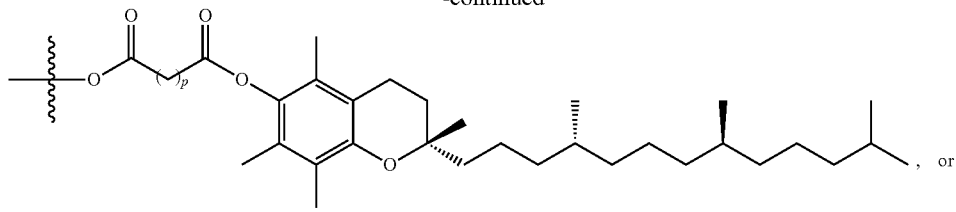, or

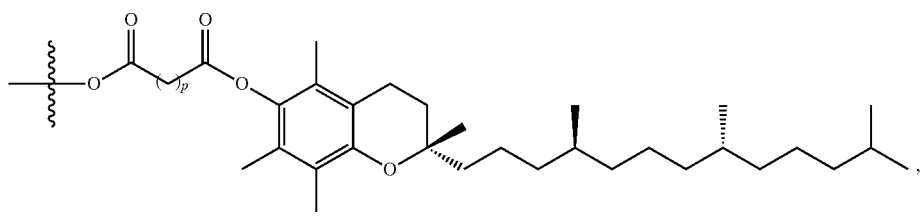, and the other one of $X^1$ and $X^2$ is not.

19. The compound of claim 12, wherein the compound is

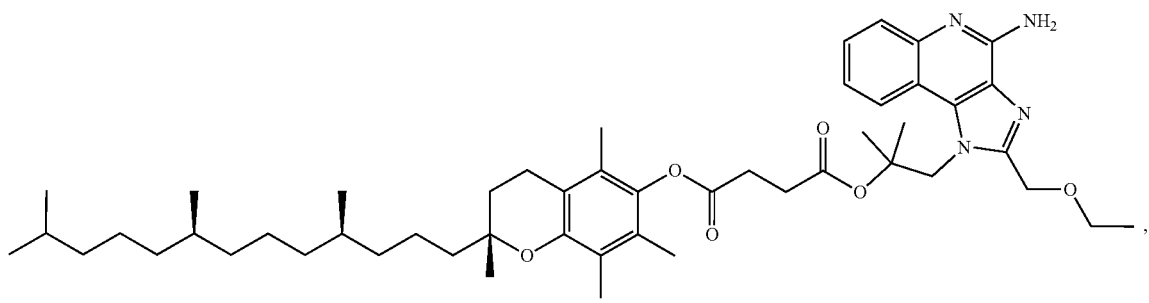 [SMILES: CCOCc1nc2c(N)nc3ccccc3c2n1CC(C)(C)OC(=O)CCC(=O)Oc1c(C)c(C)c2c(c1C)CC[C@@](C)(CCC[C@H](C)CCC[C@H](C)CCCC(C)C)O2]

or a pharmaceutically acceptable salt thereof.

20. A composition comprising the compound of claim 12, a pharmaceutically acceptable carrier, and optionally a hyaluronan-tocopherol conjugate.

21. The composition of claim 20, wherein the composition comprises the compound, the pharmaceutically acceptable carrier, and the hyaluronan-tocopherol conjugate.

22. The composition of claim 21, wherein the composition comprises an emulsion of the compound and the hyaluronan-tocopherol conjugate.

23. The composition of claim 21, wherein the wherein hyaluronan of the hyaluronan-tocopherol conjugate is substituted on a molar basis with about 6% of tocopherol.

24. The composition of claim 21, wherein the hyaluronan-tocopherol conjugate is of Formula II, III, IV, V, or a mixture of any two or more thereof:

(II)

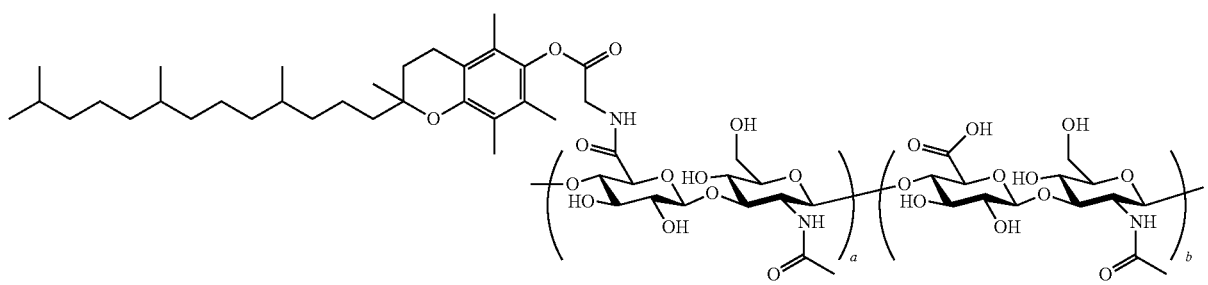

or a pharmaceutically acceptable salt thereof,

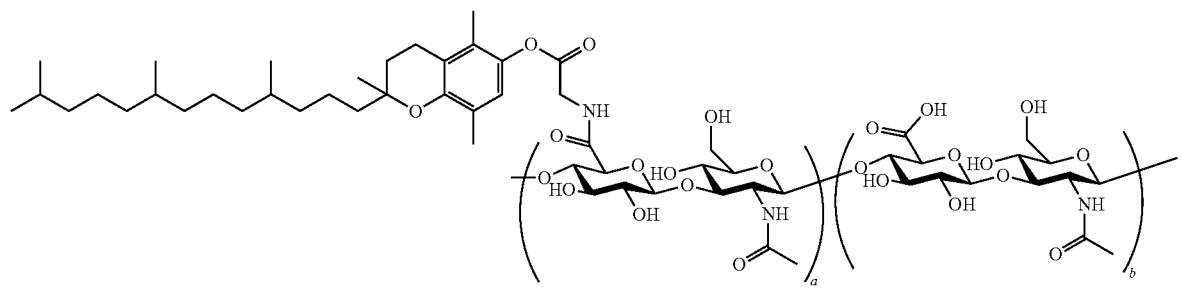

or a pharmaceutically acceptable salt thereof,

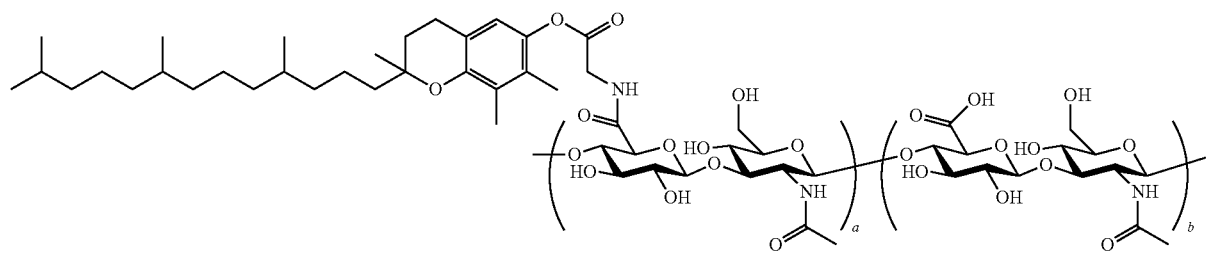

or a pharmaceutically acceptable salt thereof,

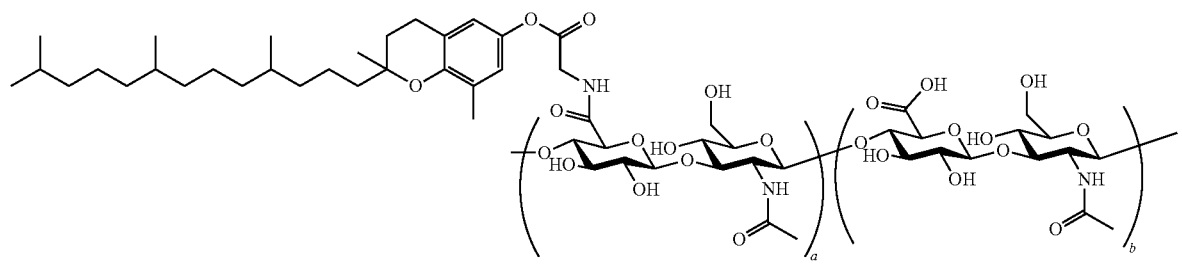

or a pharmaceutically acceptable salt thereof,
wherein a is independently at each occurrence from 1 to 800 and b is independently at each occurrence from 18 to 2540.

25. The composition of claim 21, wherein the hyaluronan-tocopherol conjugate is of Formula IIa

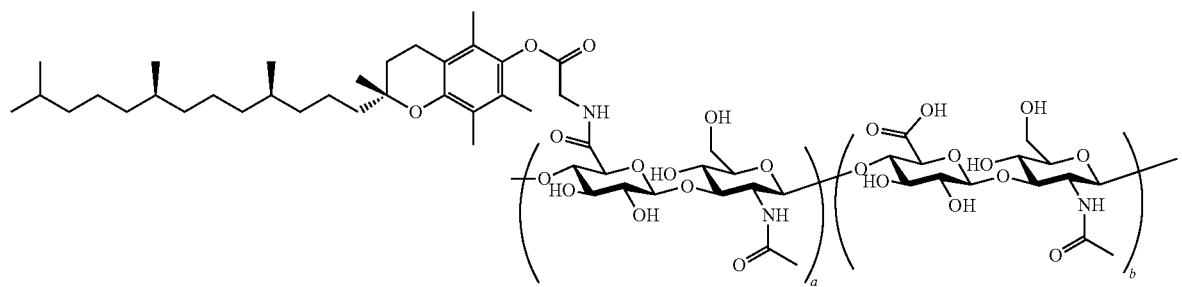

or a pharmaceutically acceptable salt thereof.

26. A method of treating superficial basal cell carcinoma, actinic keratosis, cutaneous T-cell lymphoma, or melanoma in a subject, the method comprising administering to the subject an effective amount of a compound of claim 12, wherein the effective amount is an amount effective to treat superficial basal cell carcinoma, actinic keratosis, cutaneous T-cell lymphoma, or melanoma.

27. A method of slowing or reversing growth of a tumor in a subject, the method comprising administering to the subject an effective amount of a compound of claim 12, wherein the effective amount is an amount effective to slow or reverse growth of the tumor.

28. The method of claim 27, wherein the administering further comprises administration of a chemotherapeutic agent selected from the group consisting of an alkylating agent; a nitrosourea; an antimetabolite; an anthracycline; a topoisomerase II inhibitor; a mitotic inhibitor; an anti-estrogen; a progestin; an aromatase inhibitor; an anti-androgen; an LHRH agonist; a corticosteroid hormone; a DNA alkylating agent; a taxane; a *vinca* alkaloid; a microtubule poison, and a combination of any two or more thereof.

29. A method of vaccinating a subject, wherein the method comprises administering a vaccine for a disease and administering a vaccine adjuvant comprising a compound of claim 12.

* * * * *